US007569217B2

(12) United States Patent
Tikoo

(10) Patent No.: US 7,569,217 B2
(45) Date of Patent: Aug. 4, 2009

(54) PORCINE ADENOVIRUS E1 AND E4 REGIONS

(75) Inventor: Suresh K. Tikoo, Saskatoon (CA)

(73) Assignee: University of Saskatchewan, Saskatoon (CA)

(*) Notice: Subject to any disclaimer, the term of this patent is extended or adjusted under 35 U.S.C. 154(b) by 107 days.

(21) Appl. No.: 10/199,550

(22) Filed: Jul. 19, 2002

(65) Prior Publication Data

US 2003/0099615 A1 May 29, 2003

Related U.S. Application Data

(63) Continuation-in-part of application No. 09/963,038, filed on Sep. 24, 2001, now abandoned.

(51) Int. Cl.
*C12N 15/861* (2006.01)
*C12N 15/34* (2006.01)
*C12N 15/11* (2006.01)
*C12N 15/87* (2006.01)
*C12N 15/90* (2006.01)
*C12N 15/00* (2006.01)
*A61K 48/00* (2006.01)

(52) U.S. Cl. .................... 424/93.2; 424/93.7; 424/93.6; 435/325; 435/455; 435/456; 435/320.1

(58) Field of Classification Search ................ 424/93.2; 435/455, 456, 320.1, 69.1, 91.4, 91.41, 91.42
See application file for complete search history.

(56) References Cited

U.S. PATENT DOCUMENTS

| | | | | |
|---|---|---|---|---|
| 5,882,877 | A | 3/1999 | Gregory et al. | |
| 6,080,569 | A | 6/2000 | Graham et al. | |
| 6,492,343 | B1 | 12/2002 | Reddy et al. | |
| 6,635,244 | B2 * | 10/2003 | Shen et al. | 424/93.2 |
| 2003/0104625 | A1 * | 6/2003 | Cheng et al. | 435/456 |
| 2003/0130187 | A1 | 7/2003 | Reddy et al. | |
| 2003/0143200 | A1 | 7/2003 | Tikoo | |

FOREIGN PATENT DOCUMENTS

| | | |
|---|---|---|
| AU | 714867 | 4/1995 |
| EP | 0 259 149 | 3/1988 |
| WO | WO-95/02697 A1 | 1/1995 |
| WO | WO-96/10642 A1 | 4/1996 |
| WO | WO-97/20036 A1 | 6/1997 |
| WO | WO 99/08706 | 2/1999 |
| WO | WO 99/53047 | 10/1999 |
| WO | WO 00/50076 | 8/2000 |
| WO | WO-03/040305 A2 | 5/2003 |
| WO | WO-03/040305 A3 | 5/2003 |

OTHER PUBLICATIONS

Reddy et al, Porcine adenovirus-3 as a helper-dependent expression vector, JGV, 1999, vol. 80, pp. 2909-2916.*

Telling et al, Absence of an Essential Regulatory influence of the Adenovirus E1B 19-Kilodalton Protein on Viral Growth and Early Gene Expression in Human Diploid WI38, HeLa and A549 Cells, JVI, 1994, vol. 68, No. 1, pp. 541-547.*

Zhang et al, Antigen presenting cells expressing Fas ligand down-modulate chronic inflammatory disease in Fas ligand-deficient mice, JCI, 2000, vol. 105, No. 6, pp. 813-821.*

Bruder et al, Expression of gp19K Increases the Persistence of transgene Expression from an Adenovirus Vector in the Mouse Lung and Liver, JVI, 1997, vol. 71, No. 10, pp. 7623-7628.*

GenBank Accession No. AF083132, L43077, U10433, L43363, (Jan. 3, 1999) "Porcine Adenovirus 3 Strain 6618, Complete Genome" located at http://www.ncbi.nlm.nih.gov/entrez/query.fcgi?CMD=search&DB=nucleotide on Jan. 29, 2002, 13 pages.

GenBank Accession No. MSU24432 (Dec. 12, 1996) "Mastadenovirus sus3 Penton Base Protein (L1) Gene, Complete cds" located at http://www.ncbi.nlm.nih.gov/entrez/query.fcgi?CMD=search&DB=nucleotide on Jan. 29, 2002, 2 pages.

GenBank Accession No. PAU33016 (Jan. 18, 1997) "Porcine Adenovirus 3 Proteinase (23K) Gene, Complete cds" located at http://www.ncbi.nlm.nih.gov/entrez/query.fcgi?CMD=search&DB=nucleotide on Jan. 29, 2002, 2 pages.

GenBank Accession No. PAU34592, (Jun. 11, 1996) "Porcine Adenovirus 3 Hexon Gene, Complete cds" located at http://www.ncbi.nlm.nih.gov/entrez/query.fcgi?CMD=search&DB=nucleotide on Jan. 29, 2002, 2 pages.

GenBank Accession No. PAU82628 (Aug. 5, 1999) "Porcine Adenovirus 3 100K Protein Gene, Complete cds" located at http://www.ncbi.nlm.nih.gov/entrez/query.fcgi?CMD=search&DB=nucleotide on Jan. 29, 2002, 2 pages.

Adam et al. (1994). "Vaccination of Pigs with Replication-Defective Adenovirus Vectored Vaccines: the Example of Pseudorabies," *Vet. Micro.* 42:205-215.

Ball et al. (1988). "Identification of Mouse Adenovirus Type 1 Early Region 1: DNA Sequence and A Conserved Transactivating Function," *Journal of Virology* 62(11):3947-3957.

Berk, A.J. and Sharp, P.A. (1977). "Sizing and Mapping of Early Adenovirus mRNAs by Gel Electrophoresis of S1 Endonuclease-Digested Hybrids," *Cell* 12:721-732.

Berk, A.J. (1986). "Adenovirus Promoters and E1A Transactivation," *Ann. Rev. Genet.* 20:45-79.

(Continued)

*Primary Examiner*—Maria Marvich
(74) *Attorney, Agent, or Firm*—Morrison & Foerster LLP

(57) ABSTRACT

The present invention relates to the characterization of the porcine adenovirus E1 and E4 regions. The complete nucleotide sequence of the genome of porcine adenovirus type 3 (PAV-3), providing the characterization of the PAV3 E1 region, is described herein. Methods for construction of infectious PAV genomes by homologous recombination in procaryotic cells are provided. Recombinant PAV viruses are obtained by transfection of mammalian cells with recombinant PAV genomes. The PAV-3 genome can be used as a vector for the expression of heterologous nucleotide sequences, for example, for the preparation and administration of subunit vaccines to swine or other mammals.

13 Claims, 40 Drawing Sheets

OTHER PUBLICATIONS

Bergelson, J.M. et al. (1997). "Isolation of a Common Receptor for Coxsackie B Viruses and Adenoviruses 2 and 5," *Science* 275:1320-1323.

Brennan, S. and Savage, R. (1990). "Embryonic Transcriptional Activation of a *Xenopus* Cytoskeletal Actin Gene Does Not Require A Serum Response Element," *Roux's Arch. Dev. Biol.* 199:89-96.

Chartier et al. (Jul. 1996). "Efficient Generation of Recombinant Adenovirus Vectors by Homologous Recombination in *Escherichia coli*," *J. Virol.* 70(7):4805-4810.

Chiocca et al. (1996). "The Complete DNA Sequence and Genomic Organization of the Avian Adenovirus CELO," *J. Virol.* 70(5):2939-2949.

Cullen, B.R. (1987). "Use of Eukaryotic Expression Technology in the Functional Analysis of Cloned Genes," *In Methods in Enzymology* vol. 152. Academic Press Inc. pp. 684-704.

Darbyshire, J.H. (1966). "Oncongenicity of Bovine Adenovirus Type 3 in Hamsters," *Nature* 211:102.

Derbyshire et al. (1975). "Serological and Pathogenicity Studies with Some Unclassified Porcine Adenoviruses," *J. Comp. Path.* 85:437-443.

Derbyshire, J.B. (1992). "Adenovirus," Chapter 11 *in Diseases of Swine*. Leman et al. eds. 7th Ed. Ames, IA: Iowa State University Press, pp. 225-227.

Eck, S.L. and Wilson, J.M. (1996). "Gene-Based Therapy," Chapter 5 *in Goodman & Gilman's The Pharmacological Basis of Therapeutics*. 9th Ed., McGraw-Hill, pp. 77-101.

Fallaux et al. (1996). "Characterization of 911: A New Helper Cell Line for the Titration and Propagation of Early Region 1-Deleted Adenoviral Vectors," *Human Gene Therapy* 7: 215-222.

Fallaux et al. (1998). "New Helper Cells and Matched Early Region 1-Deleted Adenovirus Vectors Prevent Generation of Replication-Competent Adenoviruses," *Human Gene Therapy* 9:1909-1917.

Gerard, R.D. and Meidell, R.S. (1993). "Adenovirus-Mediated Gene Transfer," *TCM* 3(5):171-177.

Gorman, C.M. et al. (1982). "Recombinant Genomes Which Express Chloramphenicol Acetyltransferase in Mammalian Cells," *Molecular and Cellular Biology* 2(9):1044-1051.

Graham et al. (1977). "Characteristics of a Human Cell Line Transformed by DNA from Human Adenovirus Type 5," *J. Gen. Virol.* 36:59-72.

Graham, F.L. and Prevec, L. (1991). "Manipulation of Adenovirus Vectors," Chapter 11 *in Methods in Molecular Biology*, vol. 7: *Gene Transfer and Expression Protocols*. E.J. Murray ed., The Humana Press Inc.: Clifton, NJ., pp. 109-128.

Grunhaus, A. and Horwitz, M.S. (1992). "Adenoviruses as Cloning Vectors," *Seminars in Virology* 3:237-252.

Hammond et al. (2000). "Vaccination with a Single Dose of a Recombinant Porcine Adenovirus Expressing the Classical Swine Fever Virus gp55 (E2) Gene Protects Pigs Against Classical Swine Fever," *Vaccine* 18:1040-1050.

Hanahan, D. (1983). "Studies on Transformation of *Escherichia coli* with Plasmids," *J. Mol. Biol.* 166:557-580.

Hehir et al. (1996). "Molecular Characterization of Replication-Competent Variants of Adenovirus Vectors and Genome Modifications To Prevent Their Occurrence," *J. Virol.* 70(12):8459-8467.

Hirahara et al. (1989). "Isolation of Porcine Adenovirus from the Respiratory Tract of Pigs in Japan," *Jpn. J. Vet. Sci.* 52(2):407-409.

Hirt, B. (1967). "Selective Extraction of Polyoma DNA from Infected Mouse Cell Cultures," *J. Mol. Biol.* 26:365-369.

Hu, M. and Hsu, H. (1997). "Adenovirus E1B 19K Protein is Required for Efficient DNA Replication in U937 Cells," *Virology* 227:295-304.

Imler et al. (1995). "*Trans*-Complementation of E1-Deleted Adenovirus: A New Vector to Reduce the Possibility of Codissemination of Wild-Type and Recombinant Adenoviruses," *Human Gene Therapy* 6:711-721.

Imler et al. (1996). "Novel Complementation Cell Lines Derived From Human Lung Carcinoma A549 Cells Support the Growth of E1-Deleted Adenovirus Vectors," *Gene Therapy*. 3:75-84.

Jones, N. and Shenk, T. (1979). "Isolation of Adenovirus Type 5 Host Range Deletion Mutants Defective for Transformation of Rat Embryo Cells," *Cell* 17(3):683-689.

Kadoi, K. (1997). "Beneficial Use of Inactivated Porcine Adenovirus Vaccine and Antibody Response of Young Pigs," *New Microbiol.* 20:89-91.

Kleiboeker et al. (1993). "Genomic Cloning and Restriction Site Mapping of a Porcine Adenovirusisolate: Demonstration of Genomic Stability in Porcine Adenovirus," *Arch. Virol.* 133:357-368.

Kleiboeker, S.B. (1994). "Sequence Analysis of Putative E3, p. VIII, and Fiber Genomic Regions of a Porcine Adenovirus," *Virus Research* 31:17-25.

Kleiboeker, S.B. (1995). "Identification and Sequence Analysis of the E1 Genomic Region of a Porcine Adenovirus," *Virus Research* 36:259-268.

Kleiboeker, S.B. (1995). "Sequence Analysis of the Fiber Genomic Region of a Porcine Adenovirus Predicts a Novel Fiber Protein," *Virus Research* 39:299-309.

Klonjowski et al. (1997). "A Recombinant E1-Deleted Canine Adenoviral Vector Capable of Transduction and Expression of a Transgene in Human-Derived Cells and In Vivo," *Human Gene Therapy* 8:2103-2115.

Kunkel et al. (1987). "Rapid and Efficient Site-Specific Mutagenesis Without Phenotypic Selection," *Methods in Enzymology* 154:367-382.

Ma, Y. and Mathews, M.B. (1996). "Structure, Function, and Evolution of Adenovirus-Associated RNA: A Phylogenetic Approach," *J. Virol.* 70(8):5083-5099.

Mastrangeli et al. (1996). "'Sero-Switch' Adenovirus-Mediated In Vivo Gene Transfer: Circumvention of Anti-Adenovirus Humoral Immune Defenses Against Repeat Adenovirus Vector Administration by Changing the Adenovirus Serotype," *Hum. Gene Ther.* 7:79-87.

McCoy et al. (1996). "Genomic Location and Nucleotide Sequence of a Porcine Adenovirus Penton Base Gene," *Archives of Virology* 141:1367-1375.

McCoy et al. (1996). "Nucleotide and Amino Acid Sequence Analysis of the Porcine Adenovirus 23K Protein," *DNA Sequence—The Journal of Sequencing and Mapping* 6:251-254.

McCoy et al. (1997). "Nucleotide and Amino Acid Sequence Analysis of the 100k Protein of a Serotype 3 Porcine Adenovirus," *DNA Sequence—The Journal of Sequencing and Mapping* 8(1-2):59-61.

Michou et al. (1999). "Mutational Analysis of the Avian Adenovirus CELO, Which Provides a Basis for Gene Delivery Vectors," *J. Virol.* 73(2):1399-1410.

Moffatt, S. et al. (2000). "Circumvention of Vector-Specific Neutralizing Antibody Response by Alternating Use of Human and Non-Human Adenoviruses: Implications in Gene Therapy," *Virology* 272:159-167.

Morrison et al. (1997). "Complete DNA Sequence of Canine Adenovirus Type 1," *Journal of General Virology* 78:873-878.

Park et al. (1998). "Sequence Analysis of the Early Region 1B (E1B) of Porcine Adenovirus Type 3," *RDA J. Veterinary Sci.* 40(1):19-25 (Abstract p. 19).

Reddy et al. (1993). "Restriction Endonuclease Analysis and Molecular Cloning of Porcine Adenovirus Type 3," *Intervirology* 36:161-168.

Reddy et al. (1995). "Comparison of the Inverted Terminal Repetition Sequence from Five Porcine Adenovirus Serotypes," *Virology* 212:237-239.

Reddy et al. (1995). "Molecular Cloning and Physical Mapping of Porcine Adenovirus Types 1 and 2," *Archives of Virology* 140:195-200.

Reddy et al. (1995). "Sequence Analysis of Putative p. VIII, E3 and Fibre Regions of Porcine Adenovirus Type 3," *Virus Research* 36:97-106.

Reddy et al. (1996). "Porcine Adenoviruses Types 1, 2 and 3 Have Short and Simple Early E-3 Regions," *Virus Research* 43:99-109.

Reddy et al. (1997). "Characterization of the Early Region 4 of Porcine Adenovirus Type 3," *Virus Genes* 15(1):87-90.

Reddy et al. (1998). "Nucleotide Sequence and Transcription Map of Porcine Adenovirus Type-3," *Virol.* 251:414-426.

Reddy et al. (1998). "Nucleotide Sequence, Genome Organization, and Transcription Map of Bovine Adenovirus Type 3," *Journal of Virology* 72(2):1394-1402.
Reddy et al. (1998). "Sequence and Transcription Map Analysis of Early Region-1 of Porcine Adenovirus Type-3," *Virus Res.* 58:97-106.
Reddy et al. (1999). "Development of Porcine Adenovirus-3 as an Expression Vector," *J. Gen. Virol.* 80:563-570.
Reddy et al. (1999). "Porcine Adenovirus-3 as a Helper-Dependent Expression Vector," *J. Gen. Virol.* 80:2909-2916.
Reddy et al. (1999). "Replication-Defective Bovine Adenovirus Type 3 as an Expression Vector," *J. Virol.* 73(11):9137-9144.
Rubenwolf et al. (1997). "Structural Analysis of the Adenovirus Type 5 E1B 55-Kilodalton-E4orf6 Protein Complex," *J. Virol.* 71(2):1115-1123.
Russell, W.C. (2000). "Update on Adenovirus and its Vectors," *Journal of General Virology* 81:2573-2604.
Saif, L.J. and Jackwood, D.J. (1990). "Enteric Virus Vaccines: Theoretical Considerations, Current Status, and Future Approaches," Chapter 14 *in Viral Diarrheas of Man and Animals*. Siaf, L.J. and K.W. Theil, eds. CRC Press, Inc.: Boca Raton, FL. pp. 313-329.
Shaw, W.V. (1975). "Chloramphenicol Acetyltransferase from Chloramphenicol-Resistant Bacteria," Chapter 57 *Meth. in Enzymology*. Nash, J.H. ed. Academic Press, vol. 43, pp. 737-755.
Stevenson, S.C. et al. (1995). "Human Adenovirus Serotypes 3 and 5 Bind to Two Different Cellular Receptors via the Fiber Head Domain," *Journal of Virology* 69(5):2850-2857.
Tan, P.K. et al. (2001). "Defining CAR as a Cellular Receptor for the Avian Adenovirus CELO Using a Genetic Analysis of the Two Viral Fibre Proteins," *Journal of General Virology* 82:1465-1472.
Tikoo, S.K. et al. (1993). "Analysis of Bovine Herpesvirus 1 Glycoprotein giV Truncations and Deletions Expressed by Recombinant Vaccinia Viruses," *J. Virol.* 67(4):2103-2109.
Tomko, R.P. et al. (1997). "HCAR and MCAR: The Human and Mouse Cellular Receptors For Subgroup C Adenoviruses and Group B Coxsackieviruses," *Proc. Natl. Acad. Sci. USA* 94:3352-3356.
Tuboly, T. et al. (1993). "Potential Viral Vectors for the Stimulation of Mucosal Antibody Response Against Enteric Viral Antigens In Pigs," *Research in Veterinary Science* 54:345-350.
Verma, I.M. and Somia, N. (1997). "Gene Therapy-Promises, Problems, and Prospects," *Nature* 389:239-242.
Vrati et al. (1996). "Unique Genome Arrangement of an Ovine Adenovirus: Identification of New Proteins and Proteinase Cleavage Sites," *Virology* 220:186-199.
White et al. (1992). "The 19 Kilodalton Adenovirus E1B Transforming Protein Inhibits Programmed Cell Death and Prevents Cytolysis by Tumor Necrosis Factor α," *Mol. Cell. Biol.* 12(6):2570-2580.
White, E. and Stillman, B. (1987). "Expression of Adenovirus E1B Mutant Phenotypes is Dependent on the Host Cell and on Synthesis of E1A Proteins," *J. Virol.* 61(2):426-435.
Whyte et al., (1988). "Two Regions of the Adenovirus Early Region 1A Proteins are Required for Transformation," *J. Virol.* 62(1):257-265.
Xiang et al. (1996). "A Replication-Defective Human Adenovirus Recombinant Serves as a Highly Efficacious Vaccine Carrier," *Virology* 219:220-227.
Xu, Z.Z. and Both, G.W. (1998). "Altered Tropism of an Ovine Adenovirus Carrying the Fiber Protein Cell Binding Domain of Human Adenovirus Type 5," *Virology* 248:156-163.
Ying et al. (1998). "Mouse Adenovirus Type 1 Early Region 1A is Dispensible for Growth in Cultured Fibroblasts," *J. Virol.* 72(8):6325-6331.
Zheng et al. (1994). "The E1 Sequence of Bovine Adenovirus Type 3 and Complementation of Human Adenovirus Type 5 E1A Function in Bovine Cells," *Virus Research* 31:163-186.
Zhou, Y. and Tikoo, S.K. (2001). "Analysis of Early Region 1 of Porcine Adenovirus Type 3," *Virology* 291:68-76.
Zhou, Y. et al. (2001) "Bovine Adenovirus Type 3 E1B$^{small}$ Protein is Essential for Growth in Bovine Fibroblast Cells," *Virology* 288:264-274.
Zoller, M.J. and Smith, M. (1982). "Oligonucleotide-Directed Mutagenesis Using M13-Derived Vectors: An Efficient and General Procedure for the Production of Point Mutations in any Fragment of DNA," *Nucleac Acids Research* 10(20):6487-6500.
Bett, A. J. et al. (Sep. 1994). "An Efficient and Flexible System for Construction of Adenovirus Vectors With Insertions or Deletions in Early Regions 1 and 3," *Proc. Natl. Acad. Sci. USA* 91:8802-8806.
Callebaut, P. et al. (1992). "Development of a Recombinant Vector Virus for Vaccination Against Viral Diarrhoea and Respiratory Disease in Pigs," *Med. Fac. Landbouww. Univ. Gent.* 54(4b):2077-2084.
Callebaut, P. et al. (1994). "Construction of a Recombinant Adenovirus for the Expression of the Glycoprotein S. Antigen of Porcine Respiratory Coronavirus," *Coronaviruses*, pp. 469-470.
Fields, B.N. et al., eds. (1996). "Vaccine" Chapter 68 *In Fields Virology*, Lippincott Williams & Wilkins: Philadelphia, PA, pp. 2164-2166.
Gorziglia, M. et al. (Jul. 1992). "Expression of the OSU Rotavirus Outer Capsid Protein VP4 by an Adenovirus Recombinant," *Journal of Virology* 66(7):4407-4412.
Graham, F. L. et al. (1995). "Methods of Construction of Adenovirus Vectors," *Molecular Biotechnology* 3:207-220.
Kleiboeker, S. B. et al. (1993). "Genomic Cloning and Restriction Site Mapping of a Porcine Adenovirus Isolate: Demonstration of Genomic Stability in Porcine Adenovirus," *Arch. Virol.* 133:357-368.
König, M. et al. (Oct. 1995). "Classical Swine Fever Virus: Independent Induction of Protective Immunity by Two Structural Glycoproteins," *Journal of Virology* 69(10):6479-6486.
Mittal, S. K. et al. (1995). "Development of a Bovine Adenovirus Type 3-Based Expression Vector," *Journal of General Virology* 76:93-102.
Torres, J. M. et al. (1995). "Induction of Antibodies Protecting Against Transmissible Gastroenteritis Coronavirus (TGEV) by Recombinant Adenovirus Expressing TGEV Spike Protein," *Virology* 213:503-516.
Torres, J. M. et al. (Jun. 1996). "Tropism of Human Adenovirus Type 5-Based Vectors in Swine and Their Ability to Protect Against Transmissible Gastroenteritis Coronavirus," *Journal of Virology* 70(6):3770-3780.
Tuboly, T. et al. (1995). "Restriction Endonuclease Analysis and Physical Mapping of the Genome of Porcine Adenovirus Type 5," *Virus Research* 37:49-54.
Xu, Z. Z. et al. (1997). "Construction of Ovine Adenovirus Recombinants by Gene Insertion or Deletion of Related Terminal Region Sequences," *Virology* 230:62-71.
Nagy, M. et al. (2001). "The Complete Nucleotide Sequence of Porcine Adenovirus Serotype 5," *Journal of General Virology* 82:525-529.
Tuboly, T. et al. (2000). "Characterization of Early Region 4 of Porcine Adenovirus Serotype 5," *Virus Genes* 20(3):217-219.
Tuboly, T. et al. (2000). "Sequence Analysis and Deletion of Porcine Adenovirus Serotype 5 E3 Region," *Virus Research* 68:109-117.
Paillard, F. (Nov. 20, 1997). "Advantages of Non-Human Adenoviruses Versus Human Adenoviruses," *Human Gene Therapy* 8:2007-2010.
Li, X. et al. (Sep. 1, 2004). "Analysis of Early Region 4 of Porcine Adenovirus Type 3" *Virus Research* 104(2):181-190.
Zakhartchouk, A. et al. (Sep. 2003). "A Recombinant E1-deleted Porcine Adenovirus-3 as an Expression Vector," *Virology* 313(2):377-386.

* cited by examiner

FIGURE 1-1

CATCATCAATAATATACCGCACACTTTTATTGCCCCTTTTGTGGCGTGGTGATTGGCGGAGAGGGT
TGGGGGCGGCGGGCGGTGATTGGTGGAGAGGGGTGTGACGTAGCGTGGGAACGTGACGTCGCGTGG
GAAAATGACGTGTGATGACGTCCCGTGGGAACGGGTCAAAGTCCAAGGGGAAGGGGTGGAGCCCTG
GGGCGGTCCTCCGCGGGGCGGGGCCGAGCGGCGGAAATTCCCGCACAGGTGGAGAGTACCGCGGGA
TTTTGTGCCCTCTGGACCGGACCTTCGCCCTCCGGTGTGGCACTTCCGCACCACACGTCCGCGGCC
CGGTATTCCCCACCTGACGACGGTGACACCACTCACCTGAGCGGGGTGTCCTTCGCGCTGAGAGGT
CCGCGGCGGCCGCCCGAGATGACGTGTGTGGGTGTATTTTTTCCCCTCAGTGTATATAGTCCGCGC
AGCGCCCGAGAGTCACTACTCTTGAGTCCGAAGGGAGTAGAGTTTTCTCTCAGCGGAACAGACCCT
CGACATGGCGAACAGACTTCACCTGGACTGGGACGGAAACCCCGAGGTGGTGCCGGTGCTGGAATG
GGACCCGGTGGATCTGCGCGACCCCTCTCCGGGGGATGAGGGCTTCTGTGAGCCGTGCTGGAGAG
TCTGGTCGATGGACTGCCGGACGAGTGGCTGGACAGTGTGGACGAGGTGGAGGTGATTGTGACTGA
GGGGGGTGAGTCAGAGGACAGTGGTGGGAGTGCCGCTGGTGACTCAGGTGGCTCTCAGGGGGTCTT
TGAGATGGACCCCCCAGAAGAGGGGGACAGTAATGAGGAGGATATCAGCGCGGTGGCTGCGGAGGT
GCTGTCTGAACTGGCTGATGTGGTGTTTGAGGACCCACTTGCGCCACCCTCTCCGTTTGTGTTGGA
CTGCCCCGAGGTACCTGGTGTGAACTGCCGCTCTTGTGATTACCATCGCTTTCACTCCAAGGACCC
CAATCTGAAGTGCAGTCTGTGCTACATGAGGATGCATGCCTTTGCTGTCTATGGTGAGTGTTTTTG
GACATTTGTGGGATTATGTGGAAAAAAAGGAAAAAGTGCTTGTAAGAAATCTCATGTGCTATTTCC
CATTTTTTGTCTTTTTAGAAGCTGTTTCTCCAGCACCTCACAGGTCGGGTTCCCCGGGACTTGGAG
ACCTGCCAGGACGCAAGAGGAAGTACTGCTATGACTCATGCAGCGAACAACCTTTGGACCTGTCTA
TGAAGCGCCCCCGCGATTAATCATTAACCTCAATAAACAGCATGTGATGATGACTGATTGTCTGTG
TCTCTGCCTATATATACCCTTGTGGTTTGCAGGGAAGGGATGTGGTGACTGAGCTATTCCTCAGCA
TCATCATCGCTCTGCTTTTTTCTACTGCAGGCTATTTCTTGCTAGCTCGCTGTCCCTTTTCTTTTT
CTGTGGGCATGGACTATCAACTTCTGGCCAAGCTTACTAACGTGAACTACCTTAGGAAGGTGATAG
TACAGGGGTCTCAGAACTGCCCTTGGTGGAAAAAGATTTTTTCGGACAGGTTTATCAAGGTAGTAG
CAGAGGCCAGGAGGCAGTACGGGCAAGAGTTGATTGAGATTTTTGTGGAGGGTGAGAGGGGCTTTG
GTCCTGAGTTCCTGCGGGAAGGGGGACTGTACGAAGAGGCCGTTCTGAAAGAGTTGGATTTCAGCA
CCTTGGACGCACCGTAGCTAGTGTGGCTCTGGTCTGCTTCATTTTTGAGAAGCTTCAGAAGCACA
GCGGGTGGACTGACGAGGGTATTTTAAGTCTTCTGGTGCCGCCACTATGTTCCCTGCTGGAGGCGC
GAATGATGGCGGAGCAGGTGCGGCAGGGGCTGTGCATCATCAGGATGCCGAGCGCGGAGCGGGAGA
TGCTGTTGCCCAGTGGGTCATCCGGCAGTGGCAGCGGGGCCGGGATGCGGGACCAGGTGGTGCCCA
AGCGCCCGCGGGAGCAGGAAGAGGAGGAGGAGGACGAGGATGGGATGGAAGCGAGCGGGCGCAGGC
TCGAAGGGCCGGATCTGGTTTAGATCGCCGCCGGCCCGGGGGAGCGGGTGGAGAGGGGAGCGGGGA
GGAGGCGGGGGGGTCTTCCATGGTTAGCTATCAGCAGGTGCTTTCTGAGTATCTGGAGAGTCCTCT
GGAGATGCATGAGCGCTACAGCTTTGAGCAGATTAGGCCCTATATGCTTCAGCCGGGGGATGATCT
GGGGGAGATGATAGCCCAGCACGCCAAGGTGGAGTTGCAGCCGGGCACGGTGTACGAGCTGAGGCG
CCCGATCACCATCCGCAGCATGTGTTACATCATCGGGAACGGGGCCAAGATCAAGATTCGGGGGAA
TTACACGGAGTACATCAACATAGAGCCGCGTAACCACATGTGTTCCATTGCGGGCATGTGGTCGGT
GACTATCACGGATGTGGTTTTTGATCGGGAGCTACCGGCCCGGGGTGGTCTGATTTTAGCCAACAC
GCACTTCATCCTGCACGGCTGCAACTTCCTGGGCTTTCTGGGCTCGGTAATAACGGCGAACGCCGG
GGGGGTGGTGCGGGGATGCTACTTTTTCGCCTGCTACAAGGCGCTGGACCACCGGGGGCGGCTGTG
GCTGACGGTGAACGAGAACACGTTTGAAAAGTGTGTGTACGCGGTGGTCTCTGCGGGGCGTTGCAG
GATCAAGTACAACTCCTCCCTGTCCACCTTCTGCTTCTTGCACATGAGCTATACGGGCAAGATAGT
GGGGAACAGCATCATGAGCCCTTACACGTTCAGCGACGACCCCTACGTGGACCTGGTGTGCTGCCA
GAGCGGGATGGTGATGCCCCTGAGCACGGTGCACATCGCTCCCTCGTCTCGCCTGCCCTACCCTGA
GTTCCGCAAGAATGTGCTCCTCCGCAGCACCATGTTTGTGGGCGGCCGCCTGGGCAGCTTCAGCCC
CAGCCGCTGCTCCTACAGCTACAGCTCCCTGGTGGTGGACGAGCAGTCCTACCGGGGTCTGAGTGT
GACCTGCTGCTTCGATCAGACCTGTGAGATGTACAAGCTGCTGCAGTGTACGGAGGCGGACGAGAT
GGAGACGGATACCTCTCAGCAGTACGCCTGCCTGTGCGGGGACAATCACCCCTGGCCGCAGGTGCG
GCAGATGAAAGTGACAGACGCGCTGCGGGCCCCCCGGTCCCTGGTGAGCTGCAACTGGGGGGAGTT
CAGCGATGACGATGACTGAGGATGAGTCACCCCCTCCCCTCCTCTTGCAGGTACGTGGCCCCGCCC
AGTGGGATGGGCTTTGGATGGGGGAGGGGTGTTCCCTATAAAGGGGGATGGGGGTGGAGGCATGC
AGCCCCACGGGGAAGCTTGTGTGGAGGATGTCTTCCGAGGGTGAGATCCGGACCTGCTTCATTTCA

FIGURE 1-2

GCTCGTCTTCCCAGCTGGGCCGGCGTGCGTCAGGGAGTGGCCGGGACGAATGTGAACGGCGGAGTG
GTGGGCGCCCCTGCCCAGAGCGGGGTGCTGGCCTACTCCCGCTTCGTTCAGCAGCAACAGCAGCAG
CCGGGGACGGCGGCGACGGGGTCTGTGTTCCGGGCGGTGTTTCCATCGGTGGATCTGAGCGCGGAG
GTGGGCATGATGCGGCAGGCGCTGGCGGAGCTGCGGCAGCAGCTGCAGGAGCTGCGGGAGGTGGTG
GAGATACAGCTGCGGGCCACGGCCTCGGAGGCGGCCGAGGAGGAAGAGGAGGAGGAGATTGTGGTG
GACGAGGAGGTGGCGCCCGGCGCTGGAGCGAACACCATGGAAGAGGAGGAGGATGAGATGGTCCTG
ACGATGACTGTGGTGGGGGACCCTGAGCCTGCTGGAGTGGAAGCCCAGCCGCCACCACCACCCACC
CCGGAGAGCGACCCTGCGGTGCCTGCTACTACCACTACCCCGAAGCGGCTCAGCTACGGCGCGAGC
AAGAGGAGCGGTCCATGCGCGGAGGACAACTGACGCGGACTGTGGGGGGAAGAAGGGGGAGGAGGA
AAGAAGACCATGGAGACGGGTGTTTGTCTTTTTCCAGCCCAACTTTATTGAGAATAATAATAAAGC
TTATGGATGTTTGGAACGATAATAGCGTGTCCAGCGTTCTCTGTCTTGCAGGGTCTTGTGTATCTT
CTCGAGGCACCGGTAGACCTGGTGTTGGACGTTGAAATACATGGGCATGACTCCCTCGGCGGGGTG
CAGGTAAAGCCACTGGAGGGCTGGGTGCGGGGGCAGGTGCAGTAGATGATCCAGTCATAGGCGTT
CTGGTTGCGGTGGTGGTTGAAAATGTCCTTGAGGAGCAGGCTGATGGCGGTGGGCAGACCCTTGGT
GTAGGCATTGATGAACCGGTTGACCTGGGCGGGCTGCATGAGGGGGGACATGATGTGGTACTTGGC
CTGGATCTTGAGGTTGGAGATGTTGCCGCTCTGGTCGCGGCGGGGGTTCATGTTGTGGAGGACGAC
GAGGACGGCGTAGCCGGTGCAGCGGGGGAAGCGGGCGTGCAGCTTGGAGGGGAAGGCGTGGAAGAA
CTTGGCGACCCCCTTGTGTCCGCCGAGGTCCTCCATGCACTCGTCGAGGACGATGGCGATGGGTCC
GCGGGCGGCGGCGCGGGCGAAGACGTTGCGTGAGTCAGTGACATCATAGTTGTGCTCCTGCATGAG
GTCCTGGTAGCTCATGCGGACAAAGTCTGGCATGAGGGTGGCGGTCTGGGGGATTAGGGTGTGGTC
CGGACCGCTGCGGTAGTTGCCCTCGCAGATCTGGGTCTCCCAGGCGACTACCTCCTGCGGGGGGAT
CATGTCCACCTGCGGGGTGATGAAGAAAACAGTCTCCGGCGGGGGGGAGAGGAGTTGGGAGGAGAT
GAGGTTGCGGAGCAGCTGGGACTTGCCGGAGCCGGTGGGACCGTAGATGACAGCGATGACTGGCTG
GACCTGGTAGTTGAGGGAGCGGCAGGTGCCAGCCGGGGTGAGGAAGGGCATGCAGGCGTTGAGGGT
GTCGCGCAGGTTGCGGTTCTCTTGGACGAGGTCCTGCAGGAGGTGTCGGCCTCCCAGGGAGAGGAG
GTGGGAGAGGGAGGCGAAGGCCTTGAGGGGCTTGAGGCCCTCGGCGTAGGGCATGTCCTGCAGGGC
CTGGTGGAGCACGCGCATGCGCTCCCAGAGCTCGGTTACATGTCCCACGGTATCGTCCTCCAGCAG
GTCTGGTTGTTTCTCGGGTTGGGGTTGCTGCGTGAGTACGGAACGAGGCGGTGGGCGTCGAGCGGG
TGGAGGGTCCGGTCCTTCCAGGGCCGGAGGGCCCGCGTGAGGGTGGTCTCGGTGACGGTGAAGGGG
GCGGTCTGGGGCTGCTCGGTGGCCAGGGTCCTCTTGAGGCTGAGGCGGCTGGTGCTGAAGGTGGCG
CTTCCGAGCTGCGCGTCGTTCAGGTAGCACTGGCGGAGGAGGTCATAGGAGAGGTGTTGGGTGGCA
TGGCCCTTGGCGCGGAGCTTGCCGGGGCCGCGGTGCCCGCAAGCATCGCAAACGGTGTCGCGCAGG
GCGTAGAGCTTGGGGGCGAGCAGGACCGTCTCGGAGCTGTGGGCGTCGCTGCGGCAGCGCTCGCAC
TGGGTCTCGCACTCGACCAGCCAGGTGAGCTGGGGGTTCTGGGGATCGAAGACGAGGGGGCCCCCG
TTCCGCTTGAGGCGGTGTTTACCTTTGGTCTCCATGAGCTCGCGTCCGGCGCGGGTGAGGAAGAGG
CTGTCGGTGTCCCCGTAGACGGAGCGCAGGGGCCGGTCGGCGATGGGGGTGCCGCGGTCGTCGGCG
TAGAGGATGAGGGCCCACTCGGAGATGAAGGCACGCGCCCAGGCGAGGACGAAGCTGGCGACCTGC
GAGGGGTAGCGGTCGTTGGGCACTAATGGCGAGGCCTGCTCGAGCGTGTGGAGACAGAGGTCCTCG
TCGTCCGCGTCCAGGAAGTGGATTGGTCGCCAGTGGTAGTCCACGTGACCGGCTTGCGGGTCGGGG
GGTATAAAAGGCGCGGGCCGGGGTGCGTGGCCGTCAGTTGCTTCGCAGGCCTCGTCACCGGAGTCC
GCGTCTCCGGCGTCTCGCGCTGCGGCTGCATCTGTGGTCCCGGAGTCTTCAGGTGGGTACGCTACG
ACAAAGTCCGGGGTGACCTCAGCGCTGAGGTTGTCTGTTTCTATGAAGGCGGAGGAGCGGACGGAG
AGGTCGCCGCGGGCGATGGCTTCGGTGGTGCGGGCGTCCATCTGGCTGGCGAAGACCACCTTCTTA
TTGTCGAGGCGTGTGGCGAAACTGCCGTAGAGGGCGTTGGAGAGAAGCTTGGCGATGCTGCGGAGC
GTTTGGTTTCTGTCCCGGTCGGCCTTTTCCTTGGCAGCGATGTTGAGCTGCACGTAGTCTCGGGCG
AGGCAGCGCCACTCGGGGAAGATGCTGTTGCGCTCGTCCGGCAGGAGGCGCACGGCCCAGCCACGG
TTGTGGAGGGTGACCACGTCCACGGAGGTGGCTACCTCGCCGCGGAGGGGCTCGTTGGTCCAGCAG
AGGCGGCCGCCCTTGCGGGAGCAGTAGGGGGGCAGGACGTCCAGCTGGTCCTCGTCGGGGGGGTCG
GCGTCGATGGTGAAGAGGGCGGGCAGGAGGTCGGGGTCGAAGTAGCTGAGGGGCTCGGGGCCGTCG
AGGCGGTCCTGCCAGCGGCGGGCGGCCAGGGCGCGGTCGAAGGGGTTGAGGGGTTGGCCGGCGGGG
AAGGGGTGGGTGAGGGCGCTGGCATACATGCCGCAGATGTCATAGACGTAGAGGGGCTCCCGCAGG
AGGCCGATGAAGTTGGGGTAGCAGCGGCCGCCGCGCAGGCTCTTCGCGGACGTAGTCATACAGCTC
GTGGGAGGGCGCGAGGAGGTTCGGCCGAGGTGCGGCGCCTGGGGCCGGCTGGCGCGGTAGAGGAGC
TGCTTGAAGATGGCGTGGGAGTTGGAGCTGATGGTGGGCCTCTGGAAGACATTGAAGGCGGCGTGG
GGAAGGCCGGCCTGCGTGTGGACGAAGGCGCGGTAGGACTCTTGCAGCTTGCGGACCAGACGGGCG
GTGACGACGACGTCCTGGGCGCAGTAGCGCAGGGTGGCCTGGACGATGTCGTAAGCGTCCCCCTGG

FIGURE 1-3

CTCTCCTTCTTCCACAGGTCCTTGTTGAGGAGGTACTCCTGATCGCTGTCCCAGTACTTGGCGTGT
GGGAAGCCGTCCTGATCGCGTAAGTAGTCCCCCGTGCGGTAGAACTCGTTCACGGCATCGTAGGGG
CAGTGTCCCTTGTCCACGGCCAGCTCGTAGGCCGCGGCGGCCTTGCGGAGGCTGGTGTGCGTGAGG
GCGAAGGTGTCCCGGACCATGAACTTGACGTACTGGTGCTGGGGGTCCTCGGGGGCCATGACGCCC
TCCTCCCAGTCCGCGTAGTCGCGGCGCGGGCGGAAGGCGGGGTTGGGCAGGTTGAAGCTGATGTCA
TTGAAGAGGATGCGGCCGTTGCGCGGCATGAAGGTGCGGGTGACCAGGAAGGAGGGGGGCACCTCG
CGGCGGTGGGCGAGCACCTGCGCGGCCAGGACGATCTCATCGAAGCCCGAGATGTTGTGGCCCACG
ATGTAGACCTCCAGGAAGAGGGGCGGCCCGCGCAGGCGGCGGCGCCGCAGCTGGGCATAGGCCAGG
GGGTCCTCGGGGTCGTCCGGCAGGCCGGGGCCCCGCTCCTGCGCCAGCTCGGCGAGGTCTGGGTTG
TGGGCCAGCAGGTGCTGCCAGAGGGTGTCGGTGAGGCGGGCCTGCAGGGCGTGCCGCAGGGCCTTG
AAGGCGCGGCCGATGGCGCGCTTCTGCGGGCAGAGCATGTAGAAGGTGTGGGCTCGGGTCTCCAGC
GCTGCAGGCGGGCTCTGGACGGCCACCACCTGCAGCGCGGCGTCCAGCAGCTCCTCGTCCCCCGAG
AGGTGGAAGACCAGCAGGAAGGGCACGAGCTGCTTTCCGAAGCGGCCGTGCCAGGTGTAGGTCTCC
AGGTCATAGGTGAGGAAGAGGCGGCGGGTGCCCTCGGGGGAGCCGATGGGGCGGAAGGCGATGGTC
TGCCACCAGTCGGCCGTCTGGCGCTGAACGTGGTGGAAGTAGAAGTCCCGGCGGCGCACGGAGCAG
GTGTGGGCGGTCTGGAAGATGCGGCCGCAGTGCTCGCACTTCTGGGCCTCCTGGATGCTCTTGATG
AGGTGGCAGCGGCCCTGGGTGAAGAGCAGGCGGAGGGGGAAGGGGAGGCGGGGCGGCGGGCCCTCG
GGCGGGGGGTCCCAGCGCACGTGGTGCAGGTGGTGTTGCTGGCGGGTGACCACCTGGACGAAGGTG
GGCCCGGCGGCGCGGGCCAGCTCCACCGCGGTCTGGGGGGTAGCCTGCAGGAGGTCGGGGGGCGGG
CGCAGGAGGTGCAGCTGGAAGAGGTTGGCCAGGGCGCTGTCCCAGTGGCGGTGGTAGGTGATGCTC
CAGCTCTCCCCGTCCTGGGTGGTGCCCTGGAGGCGGAGGGTGGCGCGGCGCTCGAGCAGGAGCCCC
CGCGTGCCGGCCTCCGCGGCCTCGGCGGCGGCGGCCGGTCTCAGGCGGGCAGCTGGGCCAGGGGCA
CGGGCGCGTTGAGCTCGGGCAGCGGGAGGTGGTCGCGGCGCAGACGCGAGGCGTGGGCGATGACGC
GGCGGTTGATGTTCTGGATCTGCGGGTTCCCGGAGAAGACCACGGGCCCGGTGACTCGGAACCTGA
AAGAGAGTTCCACGGAATCAATGTCGGCATCGTGGGTGGCCACCTGGCGCAGGATCTCGGACACGT
CCCCGCTGTTTTCGCGGTAGGCGATGTCCTGCATGAACTGCTCGAGCTCGTCCTCGTCCAGGTCCC
CGTGGCCGGCGCGCTCCACGGTGGCGGCCAGGTCGACGGTGATGCGGTTCATGATGGCCACCAGGG
CGTTCTCTCCGTTCTCGTTCCACACGCGACTGTAGACCAGCTGGCCGTCGGCGTCCCGCGCGCGCA
TGACTACCTGGGCCAGGTTGAGCGCCACCAGGCGGTTGAAGGGCGCCTGCAGGCGCAGGGCGTGGT
GCAGGTAGTTGAGGGTGGTGGCGATGTGCTCGCAGAGGAAGAAGTTTATGACCCAGCGGCGCAGGG
TCAGCTCGTTGATGTCGCCCAGGTCCTCGAGGCGCTGCATGACCCGGTAGAACTCGGGGGCGAAGC
GAAAAAACTCGTGCTGGCGGGCCGAGACCGTGAGCTCCTCTTCCAGGGCGGCGATGGCCTCGGCCA
CCGCCTGCCGCACCTCCTCCTCTAAGGAGGGCGGGGGCGTGCTGGGTCCGGCCACCGCCGCCTCTT
CTTCCTCTTCTCCCTCCAGGGGTGGCATCTCCTCGTCTTCTTCTTCTGCTGCTGCTGCCTCCGCGG
GGACGGGGGGCGCAGGCCGGGGACGGCGCCGGCGCAAGGGCAGCCGGTCCACGAAGCGCTCGATGA
CCTCGCCCCGCATGCGGCGCATGGTCTCGGTGACGGCGCGGCCGCCCTCCCGGGGCCGCAGCTCGA
AGGCGCCCCCGCGCAGCGCGGTGCCGCTGCAGAGGGGCAGGCTGAGCGCACTGATGATGCAGCGTG
TCAACTCTCTCGTAGGTACCTCCTGCTGTTGCAGCGCTTCGGCAAACTCGCGCACCTGCTCTTCGG
ACCCGGCGAAGCGTTCGACGAAGGCGTCTAGCCAGCAACAGTCGCAAGGTAAGTTGAGCGCGGTGT
GCGTCGGGAGCCGGAGGTGCCGGCTGACGAGGAAGTGAAAGTAGGCCGTCTTGAGCTGCCGGATGG
CGCGCAGGAGGGTGAGGTCTTTGCGGCCGGCGCGCTGCAGGCGGATGCGGTCGGCCATGCCCCAGG
CCTCCTGCTGGCAGCGGCCGATGTCCTTGAGCTGCTCCTGCAGCAGATGTGCCACGGGCACGTCCC
GGTCGGCGTCCAGGTGGGTGCGACCGTAGCCCCGCAGGGGGCGCAGCAGCGCCAGGTCGGCCACCA
CGCGCTCGGCCAGGATGGCCTGCTGCATGCGCTGCAGGGAGTCTGAGAAGTCATCCAGGTCCAGGA
ACCGGTGGTAGGCGCCCGTGTTGATGGTGTAGGAGCAGTTGCCCAGCACGGACCAGTTGACCACCT
GGTAGTGGGGCTGGATGACCTCGGTGTAGCGCAGTCGACTGTAGGCGCGCGTGTCAAAGATGTAAT
CGTTGCAGAGGCGCAGCAGGTGCTGGTAGCCCACGAGCAGGTGGGGCGGAGGGTAGAGGTAGAGGG
GCCAGTGTTCCGTGGCCGGTTGGCGGGGGGAGAGGTTCATGAGCATGAGGCGGTGGTAGCGGTAGA
TGAAGCGGGACATCCAGGCGATGCCGACGGCGGAGACGGAGGCGCGGGTCCACTGGTGGGCGCGGT
TCCAAATGTTGCGCACCGGGCGGAAGAGCTCCACGGTGTAAATGGATTGCCCCGTGAGGCGGGCGC
AGTCGAGGGCGCTCTGTCAAAAAGAACCGGGTGTGGTTGGTTGGTGTGTGGTAGCGATCTATCTTT
CTTTGTGATCTTGGTAGTGAAGCCTGCCAGGCTCCAGCAGGGGGCGTCCGCCGTCTTTCCTTCCTT
CCCTATCTGGAGGTGTGTCTCTGTTCTCTTTTTTATTTCATGTAGCCATGCATCCCGTTCTGCGGC
AGATGAAGCCGCCGGCCGGCGCCCTGGGCGCGGAGGGGGCGACGCGCTCTCGGTCGCCCTCGCCGT
CGCTGACGCGGCCGCGCGAGGAGGGGGAGGGCCTGGCGCGGCTGTCGGGCGCGGCGGCCCCCGAGC
GGCACCCACGGGTGCAGCTCAAGCGAGAGGCCATGGAGGCCTATGTGCCGAGGCAGAATGCGTTCC

FIGURE 1-4

GCGAGCGACCGGGGGAGGAGGGGGAGGAGATGAGGGACCTGCGGTTCCGCGCGGGGCGGGAGATGC
AGCTGGACCGGGAGCGAGTGCTCCAGCCCGAGGACTTTGAGGGGCGCGTGGAGGAGGCGGGGGAG
TGAGCGCGGCGCGGGCCCACATGAGCGCGGCCAGCCTGGCCCAGGCCTACGAGCAGACGGTACGCG
AGGAGGTCAACTTCCAAAAGACCTTCAACAACAACGTGCGCACCCTGGTGAGCCGGGACGAGGTGA
CCATGGGACTGATGCACCTGTGGGACTTTGTGGAGGCCTTCCTGCAGCACCCCCGGTCCCGCGCGC
TGACCGCGCAGCTGCTGCTGATCGCGCAGCACTGCCGGGACGAGGGCATGGTGAAGGAGGCGCTGC
TGAGCCTGGGCGCGCCCGAGAGCCGCTGGCTGGTGGACCTGGTGAACCTGCTCCAGACCATTGTGG
TGCAGGAGCGGTCCATGAGCCTGAGCGAGAAGGTGGCGGCCATCAACTACTCGGTGGCGACCCTGG
CCAAGCACTACGCGCGCAAGATCTCCACCTTCTACATGCGCGCGGTGGTGAAGCTGCTGGTGCTGG
CCGACAACCTGGGCATGTACCGCAACAAGCGGCTGGAGCGCGTGGTCAGCACCTCGCGGCGGCGCG
AGCTCAATGACAAGGAAGCTCATGTTTGGCCTCCGCCGGGCGCTGGCCGGGGAGGGCGAGGAGGAC
CTGGAGGAGGAGGAGGACCTGGAGGAGGCGGAGGAGGAGGAGCTGGAAAGAGGAGGAGTTCGGTCC
CCGGGGACCGCGGCGCGTGAGGTGGCAGTCCCCGCTGACTGCGAGCGATGAGGGTGATGTGTACTG
ATGGCAACCATCCCCCTTTTTAACAACAACAGCAGCATGGCGGCGAGCTCTGAAGCTGGGGCGGCG
GCGGCGGGGGTGAGCGCGGCCTCCCTGGCGCCCGAGCGGGCGACGCGGATGCAGGCGCTGCCCTCC
CTGGACGAGCCTTGGGAGCAGGCTCTGCGGCGCATCATGGCGCTGACGGCCGACGGGTCTCGGCGC
TTCGCGAGCCAGCCCCTGGCCAACCGCATCGGGGCCATCCTGGAGGCGGTGGTGCCTCCGCGCACG
AACCCGACGCACGAGAAGGTGCTGACCGTGGTGAACGCGCTGCTGGAGACCTCGGCCATCCGCCCG
GACGAGGCCGGCATGGTGTACGATGCGCTGCTGGAGCGGGTCTCCCGCTACAACAGCGGCAACGTG
CAGACCAACCTGGACCGGCTGTCCCAGGACGTGCGGCAGGTGATCGCCCAGCGCGAGCGCTCGAGC
GCCAACAACCTGGGCAGCCTGGCCGCGCTGAATGCCTTCATCGCCTCGCTGCCCGCAACGGTGGAG
CGGGGCCAGGAGAGCTACCTGGGGTTCCTCAGCGCGCTGCGGCTGCTGGTGAGCGAGGTGCCGCAG
ACGGAGGTGTTCCGCTCGGGGCCGCACACCTTCCTGCAGGCGGCGCGGAACGGTTCCAAGACGGTG
AACCTCAACCAGGCCATGGAGAACCTGCGGCCCCTGTGGGGGCTGCAGGCCCCCGCTGGGGAGCGC
GGGCACGTGTCCTCCCTGCTGACGCCCAACACCCGGCTGCTGCTGCTCCTGGTGGCTCCCTTCGCG
GAGGAGATGAACGTCAGCCGGAGCTCCTACATTGGGCACCTGCTGACACTCTACCGCGAGACGCTG
GCCAACTTGCATGTGGACGAGCGCACGTACCAGGAGATCACCAGCGTCAGCCGGGCGTTGGGCGAC
GAGGACGACGCGGCGCGGCTGCAGGCCACCCTCAACTTCTTCCTGACCAACCGGCAGCGGCGGCTG
CCGGCGGCGTATGCCCTGACCGCCGAGGAGGAGCGCATCCTGCGCTACGTGCAGCAGGCCGTGAGC
CTGTACCTGATGCAGGACGGGGCGACGGCCACGGGCGCCCTGGACGAGGCCAGCCGCAACCTGGAG
CCCAGCTTCTACGCGGCGCACCGGGACTTCATCAACCGCCTGATGGACTACTTCCATCGCGCGGCC
GCGGTGGCGCCCAACTACTTTATGAATGCCGTCCTGAACCCCCGCTGGCTGCCCTCGGAGGGCTTC
TTCACCGGCGTGTATGACTTCCCGGAGCAGGACGAGGGGGAGGAGCGGCCCTGGGACGCCTTTGAC
AGCGACGAGGAGGGCCGCCTCATGCTGCGGTCCGCAGCCTCCTCAGAGCCCTCCTCCTCCTTCACC
CCCCTGCCCCTGACCGAGGAGCCGCCCTCGCGGCCCTCCACCCCGGCCCTCTCGCGCGTCCCGTCC
CGGGCATCCTCCCTGCTCTCTCTGGCCTCTCTGGGAAAGCGGGAGGGAGGGGACTCGCTCGCCTAC
TCGCCGGCCACGCCCACCTATGGCTCTCGCTGGGGCTCGCGCCGCTCCAGCCTGGCCAGCGGCGCC
GACAGCCTGGAGTGGGACGCGCTGCTGGCCCCTCCCAAGGATGTGAACGAGCACCCAGGCGCCGCC
GCCGGCCGCCGCCGCCGCGCCTCCCGCTCCTCCCTGGAGGAGGACATCGACGCCATCAGCAGCCGG
CTGTTCACCTGGCGCACGCGCGCCCAGGAGATGGGCCTGCCCGTGGCCAGCTTCTCCCGCCGCCAC
CAGCCGCGCCCCGGGGCCCTCGAAGACGACGAGGAGGAGGAAGACTGGCGCCAGGACCGGTTCTTT
CGCTTCGAAGCGCCCGAGGAAAACCCCTTCCGCCACATCGCCCCCAAGGGGCTGTAATGCAAAAAA
GCAAAATAAAAAACCCCTCCCGGTCCAACTCACCACGGCCATGGTTGTCCTTGTGTGCCCGTCAGA
TGAGGAGGATGATGCCAGCAGCGCCGCCGCAGGGAGCGTCGCCTCCGCCGTCCTACGAGAGTGTGG
TGGGGTCTTCGCTCACGGAGCCTCTTTATGTGCCGCCGCGGTACCTGGGCCCCACCGAGGGGCGGA
ACAGCATCCGTTATTCACAGCTCCCGCCGCTCTACGATACCACAAAGATCTATCTGATCGATAACA
AGTCGGCGGATATCGCCAGTCTGAACTACCAAAACAACCACAGTGACTTTCTCACCAGCGTGGTGC
AGAACAGCGACTTCACGCCCATGGAGGCGAGCACGCAGACCATCAACCTGGATGAGCGCTCGCGCT
GGGGCGGGGAGTTTAAGAGCATTCTGACCACCAACATCCCCAACGTGACCCAGTACATGTTCAGCA
ACAGCTTCCGGGTGCGCCTGATGAGCGCGCGCGATAAAGAGACAAATGCCCCCACCTACGAGTGGT
TCACCCTGACCCTGCCCGAGGGCAACTTCTCGGACATCGCGGTCATCGACCTGATGAACAACGCGA
TCGTGGAGAACTACCTGGCGGTGGGGCGGCAGCAGGGGGTCAAGGAGGAGGACATCGGGGTGAAGA
TCGACACGCGCAACTTCCGCCTGGGCTATGACCCGGAGACCAAGCTGGTCATGCCCGGCAGCTACA
CCAACATGGCCTTTCACCCCGACGTGGTGCTGGCACCGGGCTGCGCCATCGACTTCACCTTCTCCC
GCCTAAACAACCTGCTGGGCATCCGCAAGCGCTACCCCTACCAGGAGGGCTTCATGCTGACCTACG
AGGACCTGGCGGGGGGCAACATCCCCGCGCTGCTGGACCTCACCACCTATGATCAGGAGAACTCCA

FIGURE 1-5

GCACCATCAAGCCCCTGAAGCAGGACAGCAAGGGTCGCAGCTACCACGTGGGCGAGGACCCCGAGG
CGGGGGACACCTTCACCTACTACCGCAGCTGGTACCTGGCCTACAACTACGGGGACCCGGCCACGG
GCACCGCCTCCCAGACGCTGCTGGTCTCCCCGGACGTAACCTGCGGAGTGGAGCAGGTCTACTGGA
GCCTGCCGGACCTGATGCAGGACCCGGTGACCTTCCGGCCCAGCCAGACGCCGAGCAACTACCCGG
TGGTAGCCACGGAGCTACTGCCGCTGCGCTCCCGGGCCTTCTACAACACCCAGGCCGTGTACTCCC
AGCTCCTGCAGCAGGCCACCAACAACACCCTGGTCTTTAACCGCTTCCCGGAGAACCAGATCCTCC
TGCGCCCGCCAGAGTCCACCATCACCTCCATCAGCGAGAACGTGCCCTCGCTGACGGACCACGGCA
CGCTGCCGCTGCGTAACAGCATCCCCGGGGTGCAGCGGGTAACCGTCACCGACGCGCGGCGCCGCG
TGTGTCCCTATGTGTACAAGAGTCTCGGGGTGGTGACCCCGAGGGTGCTCAGCAGCCGAACCTTCT
AACCGACAGCCCTACCCGTCACAGGGGAGACAGAGAAAAGACAGCCAGCCCCGCCATGGCCATCCT
CGTCTCGCCCAGCAACAACTTTGGCTGGGGACTGGGCCTGCGCTCCATGTACGGGGGCGCCCGCCG
CCTGTCCCCGGATCACCCCGTGATCGTCCGACGCCACTACCGGGCCAACTGGGCCAGTCTGAAGGG
ACGCGTGGCCCCCAGCACCATAGCGACAACGGATGACCCTGTGGCCGACGTGGTCAACGCGATCGC
CGGCGCCACCCGCCGCCGGCGCCGCCATCGTCGACGTCGGAGGGCCGCGCGTCTCCTCCGTGGC
CGTCACCGGGGACCCGGTGGCCGATGTGGTCAACGCGGTGGAGGCGGTAGCCCGGCGCCGCCGCGC
GCGGCGCCGTTCTTCGCGCATGCAGACCACGGGGGACCCCGTGGCGGATGTGGTGGCGGCGGTGGA
AGCGGTGGCGCGCCGGAGGCGGAGCACCCGGCGGCGGCGCAGGCGCTCCGCGCCGGCCATCCTGGG
GGTGCGCCGCAGCCGCCGCCTCCGCAAACGCACCTCGTCCTGAGATTTTTGTGTTTTGTTTTTTCT
GCCTCCCGTGGGTGAACAAGTCCATCCATCCATCCAACATCCGTGGCTGCTGTGTCTTTGTCTTTT
CTTTGCGTTGCGCCCCAGTTGAGCCGGCACCGACGCGCTCGGCCATGGCCATCTCGCGCCGCGTGA
AAAAGGAGCTGCTGCAGGCGTTGGCGCCCGAGGTGTACGGGGCGCCTAAGAAGGAGGAGAAGGACG
TCAAAGAGGAGTCCAAAGCTGACCTTAAACCGCTGAAGAAGCGGCGCAAGGCCAAGCGGGGGTTGA
GCGACAGCGACGAGGTGCTGGTGCTGGGCACGCGCCCCAGGCGCCGCTGGACGGGGCGGCGCGTGC
GCGCCCACCTACCGCCCGGTGCCAGCCTCGCCTACGTCCCGGGTCTTCGGAGGTCGAGCGCCACCA
AGCGCTCTGCGGACGAGTTGTATGCGGACACGGACATCCTGCAGCAGGCGTCCCAGCGCCTGAACG
AATTTGCTTATGGCAAGAGAGCCCGGCGGCAGCGGCGGGCCCGCCCCTCGCCGACCCCCGCGTCCC
GCGGCCGGACCACCAAGCGCTCTTATGACGAGGTCGTGGCAGACAGTGACATCCTGCAGCAACTTG
GATCCGGGGACCGCTCCAATGAGTTCTCCTATGGCAAGCGGTCGCTGCTGGGGGAGTCAGGAGACA
CCGTCCCGGCTGTGGCCGTCCCGCTGGAGGAAGGCAGGAACCACACAGCCAGCCTGCAGCCGCTCA
CCGAGCCCATGCCCCTGGTGTCCCCTCGCACGGCCGTCAAGCGCCGGGCGCCCGCCGACGAGCCCA
CCGCCTCACTGGTCCCCACCGTGCAGGTCCTGGCCCCCAAGCGTCGTCTGCAGGAGGTGGTGGTGG
AGCCGCCCGCTCCAGCACCCACGCCGCCCCTAGCCCCGCGGCGGTCCAGCCGGCGCATCATTCTGG
CTCCGCGCCGGGCGGGCCGGCCCCAGGCCGTCGTGGCGCCGCAGCTCAGCGCGGCCGCGGCGCTGG
AGCGGGCGGCGGCCGCCGTGCCCCTGCCACCGGACACGGAGGACGACCTGGTGGAGATGGCAGAGG
CTGTCGCCGCGCCCGAGGTGCTGCCCAGCCTCCCCGTCTCCATCATGCCGCCCACCGCCACGGAGG
TGGCCCTGCCCGTACAGACCCCACTGCCGCCCGTGGCGGTGGCCAAGAGCTCCCTGACCCCCGGCC
TCCGCGCGCTGATGGGCACCGAGCGGGTGCCGGTTCCAGTCCTGGAGGCGCCCCTGGTGGCCATGC
CCGTGCTCCGGGCCACCACCGCCCGTGCCGAGCCCCCGCGCCGCGTGCCCCGCAGGGCCGTGCGGG
ACATCCCGGCCAGGCAGCCCCGCACGGTATCCCTGCCCGTGCTCACGGAGCCCGGCCCGGCCACCG
CGGTCGCCTCCGTGCGCGCGGCAGCCCAAGTCCTGCAGGCGCCCCCCGCCCGACCGGCCACCGTCT
CCGTGGGGGTGGGCACCGAGCCGGTGGTGCAGTCCATCACGGTCAAGCGGTCAAAGCGCCTGACCA
AGCACCATCGGGGTGCAGACCATCGACGTCACCGTGCCCACCGTCCGCACTGTCAGCGTGGGCACC
AACACGCCCCGGCTGAGGAGCGCCTCGGTGGGCGTCCAGACCGCTCCCGAGACCCGCTCCCAGGGG
GTGCAGGTGGCTTTCCAACCAGCGTGCTAGCCCACCGCACACCCAGGCAGGTGCGGCTGACGGCGG
TGGTGCCCCCCACCCCGCGCGCCCCGGTGGTTCCGGTGGCCCGGCGCCCGCGGCGGTTCCGGTGCC
TCCCCCAGCCCCTCCAGCCCCGCGCGCGCCGCGTGCGCCTCGCGCCCCCAGAGCGCCTCGGCGTCG
CCGCCGTACCCCGGTGGCGGTGGCAGCGCCGCCCGCCCGCAGCGGCGGTCCCCCGCCCTCGGCTGC
CGAGGCGGCCCATCGTGCTGCCCGGGGTGCGCTATCATCCCAGTCAGGCCATGGCTCCCACCGCCC
AACGCGTCATCTGGCGTTGATTTATTTTTGGAGACCTGACTGTGTTGTGTTCCTTAAATTTTTTAT
CCTCCTCCTCCTCTGCTGAAGCCAGACGATGCTGACCTACCGGTTGCGGCTGCCCGTGCGGATGCG
GAGACCGAGACTCCGCGGTGGGTTCCGCGTGGCGCCTCGGCGCAGCGGCGGCAGGCGGCGGTACCG
CCGGGGGCCGATGAGGGGTGGCATCCTGCCGGCGCTGGTGCCCATCATCGCGGCATCCATCTGGGC
CATCCCCGGCATCGCCTCGGTGGCGATGAGTGCTAGACAACGCAATTAACGGCGCTGCTGTGTATG
TGTGTCTTCCATGTGCCTTCCTTCCTTCGTTCCCAACGGAACAGCAGCACCGTCTCCATGGAGGAC
CTAAGCTTTTCCGCGTTGGCTCCACGCTTTGGCACGCGGCCGGTCATGGGCACTTGGAGCGAAATC
GGCACGAGTCAGATGAACGGCGGCGCGCTCAGCTGGAGCAATATCTGGAGCGGGCTGAAGAGCTTT

FIGURE 1-6

GGTAGTTCTCTGGCCTCCACGGCCAACAAGGCCTGGAACAGCGGGACGGTGACGAGCGTGCGCAAC
AAGTTGAAGGATGCCGACGTGCAGGGGAAGATAGGTGAGGTCATTGCCTCCGGGGTCCACGGTGCC
CTGGACGTGGCCAACCAGGCCGTCTCCCACGCCGTGGACCGCCGGTGCAACAGCAGCAGCTGCGGC
AGCAGCAGCTCCTCCGCCAGCAGCAGCAACAGATGGGCCTCGTGGAACCCTCCTATGAGATGGAGA
CAGACGAGCTGCCTCCTCCCCCCGAGGACCTCTTGCCTCCTCCTCCTCCTCCGCCGCCTGCCTCGG
CCACTCCCGCGCGCCAATCCCGCGGGACGTCCCGCCAAGCGCCCGCCGCCGCCCAGGAGATCATCA
TCCGCTCCGACGAGCCCCCTCCCTATGAAGAGCTGTATCCCGACAAGGCCGGGATCCCCGCCACCT
TGGAGCTGCGTCCCGAGACCAAACTGCCCGCCGTGGCCCACAATAAGATGCGCCCCCCGCCGCCGC
TCACCACCACCACCTCCTCCGCTGCCGCCGCCGCCCCCGCCCCGGCCCCCGCGGCTCCTGTGCGTC
GGCGTCCGGCCGCGGCTCCGGCCGCGGCTCCGGCGAGTTCCAAAGGCCCCCCAGGTGGGGGTCCGC
GCGCGCGGGTGGCAAAACAAACTCAACACCATTGTGGGACTGGGTGTCCGCACATGCAAGCGCCGT
CGTTGTTACTGAGAGAGACAGCATGGAGAAACAACAATGTCTGGATTCAAATAAAGACACGCCTAT
TCTTCCACGGTGCTCCGCGCTGTGTTATTTTCAACGGGCTGTTTCCTTTTGCATCTCTGTGCCATC
GCGCCACGGGGAATTCCGCAGGATGGCGACGCCGTCGATGATGCCGCAGTGGTCCTATATGCACAT
CTCCGGGCAGGACGCGTCCGAGTACCTGTCTCCCGGGCTGGTGCAGTTCTCCCAGGCGACGGAGAC
CTACTTTAACCTGAACAACAAGTTTAGGAACCCCACCGTCGCGCCCACCCACGATGTGACGACGGA
GCGCTCGCAGCGGCTGCAGCTGCGCTTCGTCCCCGTGGACAAGGAGGACACTCAGTACACATACAA
GACCCGCTTCCAGCTGGCGGTGGGCGACAACCGCGTGTTGGACATGGCGAGCACCTTCTTTGACAT
CCGGGGAACGCTGGACCGGGGACCCTCCTTCAAACCGTACTCGGGCACCGCGTACAACATCATGGC
TCCCAAGAGCGCTCCCAACAACTGTCAATATCTAGACCCTAAAGGTGAAACTGAGGCTGGCAAAGT
TAATACCATTGCTCAAGCAAGTTTTGTGGGTCCTATTGATGAAACCACGGGAGACATTAAAATTAC
AGAAGAAGAAGACGAAGAGACCACCATCGATCCTTTGTATGAGCCCCAACCCCAGCTTGGTCCAAG
CTCGTGGTCAGACAATATACCTTCTGCGACTAGCGGAGCTGGAAGAGTTCTCAAACAGACCACACC
GCGTCAACCTTGTTACGGTTCTTATGCCTCTCCGACAAATATTCACGGTGGGCAAACGAAGGATGA
CAAGGTTACACCATTGTACTTTACAAACAATCCCGCCACCGAAGCCGAAGCACTCGAAGAAAATGG
ATTAAAGCCAAATGTCACCCTATACTCAGAGGATGTTGACCTAAAAGCACCAGATACTCATCTGGT
CTATGCTGTGAATCAAACCCAGGAATTCGCTCAATATGGACTTGGACAACAGGCCGCTCCAAACAG
GGCCAATTACATCGGCTTCAGGGACAACTTTATCGGGCTGTTGTACTACAACAGCAATGGCAACCA
GGGCATGCTAGCCGGTCAGGCCTCTCAGCTCAACGCGGTGGTCGACCTGCAGGACAGGAATCACCG
AACTAGCTACCAGCTCTTCCTCGATAGCCTCTATGACAGGTCGAGGTACTTTAGCCTGTGGAACCA
GGCCATCGATTCTTATGACAAGGATGTGCGTGTGCTGGAAAACAATGGCGTGGAGGACGAGATGCC
CAACTTTTGCTTTCCCATCGGCGCCATCGAGACCAACATGACATTTACACAGCTCAAAAAGAGTGA
GAATGGTGGCTCAAGAGCCACAACCTGGACAAAGGAGAATGGGGATGATGGCGGAAACGGAGCGGA
GCACTACCTGGGCATCGGCAACCTCAACGCCATGGAGATCAATCTCACGGCCAACCTCTGGCGCAG
CTTCCTCTACAGCAACGTGGCGCTGTACCTGCCTGACAAGTACAAGTTTTCCCCGCCCAACGTCCC
CATCGACCCCAACACGCACTCCTATGACTACATCAACAAGCGCCTGCCCCTCAACAACCTCATTGA
TACCTTTGTCAACATCGGGGCGCGCTGGTCCCCGGATGTCATGGACAACGTCAACCCCTTCAACCA
CCACCGCAACTACGGCCTGCGCTACCGCTCCCAGCTCCTGGGCAACGGCCGCTACTGCAAGTTCCA
CATCCAGGTGCCGCAAAAGTTCTTTGCCCTCAAGAGCCTGCTGCTCCTGCCGGGGGCGACCTACAC
CTACGAGTGGTCCTTCCGCAAGGACGTCAACATGATCCTCCAGTCCACGCTGGGCAACGACCTCCG
CGCGGACGGGGCCAAAATCAACATCGAGAGCGTCAACCTCTACGCCAGCTTCTTTCCCATGGCCCA
CAACACCGCCTCCACCCTGGAGGCCATGCTGCGCAACGACACCAACAACCAAACCTTTATTGACTT
CCTCTCCTCCGCCAACATGCTCTACCCCATCCCGGCCAACGTCACCAACCTGCCCATCTCCATTCC
CAGCCGCAACTGGGCCGCCTTCCGCGGCTGGAGCTTCACGCGGCTGAAGCACAACGAGACCCCCGC
CCTGGGCTCGCCCTTCGACCCCTACTTTACCTACTCGGGCTCCATCCCCTACCTGGACGGGACCTT
CTACCTGGGCCACACCTTCCGCCGCATCAGCATCCAGTTCGACTCCTCCGTGGCCTGGCCGGGCAA
TGACCGCCTGCTCACTCCCAACGAGTTCGAGGTCAAGCGCACCGTGGACGGGGAGGGCTACACGGT
GGCCCAGACCAACATGACCAAAGACTGGTTCCTGGTGCAGATGCTCGCCCACTACAACATCGGCTA
CCAGGGATACCACCTGCCAGAGGGCTACCGCGACCGCACCTACTCCTTCCTGCGCAACTTTGAGCC
CATGTGCCGCCAGGTGCCCGACTACGCCAACCACAAAGATGAGTACCTGGAGGTGCCCACCACCAA
CCAGTTCAACAGCAGCGGCTTTGTATCCGCGGCCTTCACCGCCGGCATGCGCGAGGGGCACCCATA
CCCCGCCAACTGGCCCTACCCGCTCATCGGCGAAGACGCCGTGCAGACCGTGACCCAGCGCAAGTT
CCTCTGCGACCGCACGCTCTGGCGCATCCCCTTCTCCTCCAACTTCATGTCCATGGGCACCCTCAC
CGACCTGGGCCAGAACCTCCTCTACGCCAACTCGGCCCACGCCCTCGACATGACCTTCGAGGTCGA
CGCCATGGATGAACCCACCCTCTTGTATGTTCTGTTCGAGGTCTTTGACGTCTGCGGCGTGCACCA
GCCGCACCGAGGCGTCATCGAGGCCGTCTACCTGCGCACGCCCTTCTCCGCCGGGAACGCCACCAC

FIGURE 1-7

CTAAGGCGGAGCCGCGCAGGCATGGGCAGCACCGAGGACGAGCTCCGAGCCATGGCGCGCGACCTC
CAGCTGCCCCGCTTCCTGGGCACCTTTGACAAGTCCTTCCCGGGCTTCTTGCAAGAGTCCCAGCGC
TGCTGCGCCATCGTCAACACGGCCGCCCGCCACACCGGAGGCCGCCACTGGCTGGCCGTCGCCTGG
GAGCCCGCCTCGCGCACCTTCTACTTCTTTGACCCCTTCGGCTTCTCCGACCGGGAGCTCGCCCAG
GTCTATGACTTTGAGTACCAGCGCCTGCTGCGCAAGAGCGCCATCCAGAGCACCCCGGACCGCTGC
CTCACGCTCGTCAAGAGCACCCAGAGCGTGCAGGGACCGCACAGCGCCGCCTGCGGACTCTTCTGC
CTCCTCTTCCTCGCCGCCTTTGCCCGCTACCCCGACAGCCCCATGGCCTACAATCCCGTCATGGAC
CTGGTGGAGGGCGTGGACAACGAGCGGCTCTTCGACGCCGACGTCCAGCCCATCTTCCGCGCCAAC
CAGGAGGCCTGCTACGCGTTCCTCGCTCGCCACTCCGCCTACTTCCGCGCCCACCGCCACGCCATC
ATGGAACAGACACACCTGCACAAAGCGCTCGATATGCAATAAAGGCTTTTTATTGTAAGTCAAAAA
GGCCTCTTTTATCCTCCGTCGCCTGGGGGTGTATGTAGATGGGGGACTAGGTGAACCCGGACCCG
CCGTCGGCTCCCCTCCATCCCCTCTTCTCTCAAAACAGGCTCTCATCGTCGTCCTCCGTTCCCACG
GGGAAGATGGTGTTCTGCACCTGGAACTGGGGCCCCCACTTGAACTCGGGCACCGTCAGTGGAGGC
CGCGTCTGCATCAGGGCGGCCCACATCTGTTTGGTCAGCTGCAGGGCCAGCATCACATCGGGGGCG
CTGATCTTGAAATCACAATTCTTCTGGGGGTTGCCGCGCGACCCGCGGTACACCGGGTTGTAGCAC
TGGAACACCAGCACCGCGGGGTGGGTCACGCTGGCCAGAATCTTGGGGTCTTCCACCAGCTGGGGG
TTCAGCGCCGCCGACCCGCTCAGCGCGAAGGGGGTGATCTTGCAGGTCTGCCGGCCCAGCAGGGGC
ACCTGGCGGCAGCCCCAGCCGCAGTCGCACACCAGCGGCATCAGCAGGTGCGTCTCCGCGTTGCCC
ATCCGGGGGTAGCAGGCCTTCTGGAAAGCCTTGAGCTGCTCGAAGGCCTGCTGCGCCTTGGAGCCC
TCCGAGTAGAAGAGGCCGCAGGACCGCGCCGAGAAGGTGTTGGGGGCCGACCCCACGTCGTGGCTG
CAACACATGGCCCCGTCGTTGCGCAGCTGCACCACGTTGCGGCCCCAGCGGTTGGTGGTGATCTTG
GCGCGCTCGGGGGTCTCGCGCAGGGCGCGCTGCCCGTTCTCGCTGTTGAGATCCATCTCCACCAGC
TGCTCCTTGTTGATCATGGGCAGCCCGTGCAGGCAGTGCAGCCCCTCCGAGCCGCTGCGGTGCTGC
CAGATCACGCACCCGCAGGGGTTCCACTCGGGCGTCTTCAGACCCGCCGCCTTCACCACAAAGTCC
AGCAGGAAGCGGGCCATCACTGTCAGCAGGCTCTTTTGCGTGCTGAAGGTCAGCTGGCAGCTGATC
TTGCGCTCGTTCAGCCAGGCTTGGGCCCCGCGCCGGAAGCACTCCAGGGTGCTGCCGTCCGGCAGC
AGCGTCAGGCCCTTGACATCCACCTTCAGGGGGACCAGCATCTGCACAGCCAGATCCATGGCCCGC
TGCCACTTCTGCTCCTGAGCATCCAGCTGCAGCAGCGGCCGGGCCACCGCCGGGCTCGGGGTCACC
GGGCGCGGGGGGCGGGCCCCCTCCTCTTCCTCCCCATCTTCGCCCTTCCTCCTCGCGGGCCGCGCC
GTCGCCGCTGCCGTCTCTTCAGCCTCGTCCTCCTCCTCCTCGCTGACCAGGGGCTTGGCACGCGCG
CGCTTCCGCCGCTCCTGCACGGGCGGAGAGGCCGCGCGCTTGCGGCCTCCCCCGCGCCGGCTGGGG
GTCGCGACAGGAGCGTCGTCCACAATCAGCACCCCCTCTTCCCCGCTGTCATAGTCAGACACGTCC
GAATAGCGGCGACTCATTTTGCTTCCCCTAGATGGAAGACCAGCACAGCGCAGCCAGTGAGCTGGG
GTCCTCCGCGGCCCCGACCCTTCCGCCGCCACCACCGCCGCCACCTCCGCCCACGTCACCGCCACC
TTCACTGCAGCAGCGGCAGCAGGAGCCCACCGAAACCGATGACGCGGAGGACACCTGCTCCTCGTC
CTCCTCGTCCTCCGCCTCCAGCGAGTGCTTCGTCTCGCCGCTGGAAGACACGAGCTCCGAGGACTC
GGCGGACACGGTGCTCCCCTCCGAGCCCCGCCGGGACGAGGAGGAGCAGGAGGAGGACTCGCCCGA
CCGCTACATGGACGCGGACGTGCTGCAGCGCCACCTGCTGCGCCAGAGTACCATCCTGCGCCAGGT
CCTGCAGGAGGCCGCCCCCGGCGCAGCCGCGGAGGCCGCCGAGGCGCCCTCGGTGGCGGAGCTCAG
CCGCCGCCTGGAAGCGGCCCTCTTCTCCCCCGCCACGCCGCCGCGGCGCCAGGAGAACGGAACCTG
CGCCCCGGACCCCCGCCTCAACTTCTACCCGGTCTTCATGCTGCCCGAGGCCCTGGCCACCTACCT
CGTCTTCTTCCACAACCAAAAGATCCCCGTCAGCTGCCGCGCCAACCGCCCACGAGCCGACGCGCA
CTGGCGGCTGCCCAGTGGACCCCCTTACCTGACTATCCAACCACCGACGAGGTTTACAAGATCTT
TGAGGGCCTGGGGGACGAGGAGCCGGCCTGCGCCAACCAGGACCTGAAAGAGCGCGACAGCGTGTT
AGTCGAGCTCAAGCTGGACAACCCCCGCCTGGCGGTGGTCAAGCAGTGCATCGCCGTCACCCACTT
CGCCTACCCGGCCCTGGCGCTGCCACCCAAGGTCATGAGCACGCTCATGCAGACCCTGCTGGTGCG
CCGCGCGAGCCCACTCCCCGACGAGGGCGAGACGCCCCTCGAGGACCTCCTGGTGGTCAGCGACGA
GCAGCTGGCCCGCTGGATGCACACCTCGGACCCCAAGGTCCTGGAGGAGCGGCGCAAGACCGTCAC
CGCCGCCTGCATGGTCACGGTGCAGCTCCACTGCATGCACACCTTCCTCACCTCCCGCGAGATGGT
GCGCCGCCTCGGAGAGTGCCTCCACTACATGTTCCGCCAGGGCTACGTCAAGCTAGCTAGCAAGAT
CGCCAATATGGAACTCTCTAACCTGGTCTCCTACTTGGGCATGCTGCACGAAAACAGGCTCGGTCA
GCACGTGCTCCACCACACCCTCAAGCATGAGGCGAGACGCGACTACGTCCGGGACACCATTTACCT
ATACCTGGTCTATACCTGGCAGACCGCCATGGGGGTCTGGCAGCAGTGCCTCGAGGACCGAAACCT
GCGCGCCCTGGAAACGTCTCTGGCTCGCGCTCGCCAGAGCCTGTGGACGGGCTTTGATGAGCGCAC
TATCGCGCAGGACCTCGCCGCGTTCCTTTTCCCCACCAAGCTCGTAGAGACCCTGCAGCGCTCGCT
CCCCGACTTTGCCAGCCAGAGCATGATGCATGCCTTCCGCTCCTTCGTCCTCGAGCGCTCCGGCAT

FIGURE 1-8

CCTGCCCGCCGTCTGCAACGCGCTCCCCTCTGACTTTGTGCCCACCGTCTACCGCGAGTGCCCGCC
GCCCCTCTGGGCTCACTGCTACCTCCTGCGCCTCGCCAACTTCCTCATGTACCACTGCGACCTCGC
CGAGGACACCTCCGGCGAGGGCCTCTTTGAGTGCTACTGCCGCTGCAACCTCTGCGCACCGCACCG
CTGCCTCGCCACCAACACCGCCCTCCTCAACGAGGTGCAAGCCATCAACACCTTTGAGCTCCAGCG
GCCCCCCAAGCCCGACGGCACCCTGCCACCGCCCTTCAAGCTGACCCCCGGTCTCTGGACCTCCGC
CTTCCTCCGCCACTTTGTCTCCGAGGACTACCACTCGGACCGCATCCTCTTCTACGAGGACGTGTC
CCGCCCCCCCAGGGTGGAGCCCTCCGCCTGCGTCATCACGCACTCGGCCATTCTCGCGCAATTGCA
TGACATCAAAAAGGCCAGGGAAGAGTTTTTGCTGACCAAAGGCCACGGCGTCTACCTAGACCCCCA
CACCGGAGAGGAGCTCAACACCGCCGCCCCGTCCACCGCCCACCATGCCGCCCCTCCGGAGGAAGC
CCATCCGCAGCAGCACCAGCACCAGCAGCAGCCGAGCCACCGCCGCCGCCACCACCGCTCCAGCTA
CGCAGACCGTGTCCGAAGCGAGCTCCACGCCTACGGCGGTGCGACCGGTTCCTCCCGCGACCCTGT
CTCTGGCGGATGCTCTGCCAGAGGAACCCACTCCCGCGATGCTGCTCGAAGAAGAGGCTCTCAGCA
GCGAGACCAGCGGCAGCTCCGAAGGCAGTTTGCTCAGTACCCTCGAGGAACTGGAGGAGGAGGAGG
AACCGGTCACACCGACGAGGCCATCCAAGCCCTCCTACACCAACAGCAGCAGCAGCAAGAGCATCA
GCCAGCGCAGGAACTCCGTCGTCCCCAGCGAGGCTCGTAGATGGAATCAGACATCCATCCACCGGA
GTAGCCAGCCAGGTAGGACACCTCCGCCCTCGGCCCGCCGACGCTCCTGGCGCCGCTACCGCCACG
ACATCCTCTCGGCCCTGGAGTACTGCGCCGGAGACGGAGCCTGCGTGCGCCGGTACCTACTCTACC
ACCACAACATCAACATCCCTTCCAAGATCATCCGTTACTACAAATCCTCTTCCCGTTCCAGCGATC
TCCAGGAAGGCCGCAGCAGCGGCGGCAGCAGAACCAGCCCACGTCAGCCAGCTGAGAGCTAAGATC
TTCCCCACGCTGTACGCCATCTTCCAGCAGAGCCGCGGCGGCCAGGACGCCCTCAAAATCAGGAAC
CGCACCCTGCGCTCCCTCACCAAGAGCTGTCTGTATCACCGCGAGGAGGCCAAGCTGGAACGCACG
CTCTCGGACGCAGAAGCTCTCTTCGAGAAGTACTGCGCTCGGCAGCGGCAGACCCGCCGGTATTTA
AGGAGCGGACCCTGCGTGCGGACACACCATGAGCAAACAAATCCCCACCCCGTACATGTGGTCTTA
TCAGCCACAATCTGGGCGTGCCGCCGGTGCCTCCGTCGATTACTCCACCCGCATGAATTGGCTCAG
TGCCGGGCCTTCCATGATTGGCCAGGTCAATGACATCCGACACACCAGGAACCAGATTCTCATTCG
CCAGGCCCTTATCACCGAGACGCCACGCCCCGTCCAAAATCCCCCGTCCTGGCCCGCCAGCCTGTT
GCCTCAGATGACGCAACCGCCCACCCACCTGCACCTGCCGCGTAACGAAATTTTGGAAGGCAGACT
GACTGACGCCGGCATGCAATTAGCCGGGGGCGGAGCCCTCGCACCCAGAGACTTATATGCCCTGAC
CCTCCGCGGCAGAGGCATCCAGCTCAACGAGGACCTACCCCTCTCGGCGAGCACTCTCCGGCCGGA
CGGCATCTTCCAGCTCGGAGGCGGAGGCCGCTCCTCCTTCAACCCCACCGACGCCTACCTGACGCT
GCAGAACTCCAGCTCCCTTCCCCGCAGCGGCGGCATCGGCAGCGAGCAATTTGTCCGCGAGTTCGT
GCCCACGGTCTACATCAACCCCTTCTCCGGACCGCCCGGGACCTACCCCGACCAGTTCATCGCCAA
CTACAACATCCTAACGGACTCTGTAGCAGGCTATGACTGACGGTCCCCAGGGTCAGCAGCGGCTGC
GGGAGCTCCTCGACCAGCACCGCCGCCAGTGCCCTAACCGCTGCTGCTTCGCCAGGGAAGGGATTC
ACCCGGAGTACTTTTGCATCACCCGCGAGCACTTTGAGGCCGAGTGCATCCCCGACTCTCTGCAAG
AAGGCCACGGTCTGCGCTTCAGCCTCCCCACGCGCTACAGCGACCGCCGCCACCGCGATGGAGACC
GCACCATCCTCACTTCGTACTACTGCGGCCCTGCTTCTTTCAAAGTTCGCTGTCTCTGCGGCCATC
CTGCTCCTCACCCTCTTCTTCTCGACCTTCTGTGTGAGCTGTACAACCGCTCGTAGCGTCAGCCCC
TACACCTCCCCTCGCGTCCAATTTCTGTCCGACATAGAACCAGACTCTGACTCTTACTCGGGCTCT
GGCTCTGGGGACGATGAAGATTATGAATATGAGCTGGCTACCAACACACCGAACGAAGACATTCTA
GGCAGCATAGTCATCAACAACCAGATCGGGCCCAAGACCCTGGCCCTGGGATACTTTTATGCCGCC
ATGCAGTTTGTCTTCTTTGCCATCATCATCATCGTCCTCATCCTCTACTACCGCCGCTACGTGCTG
GCCACCGCCCTCATCGTGCAGCGCCAGATGTGGTCCTCCGAGGCCGTCCTGCGGAAAACCTTCTCG
GCCACCGTTGTGGTTACTCCCCCAAAACAAGTCACCCCCTGCAACTGCTCCTGCCGCTTCGAGGAG
ATGGTGTTCTACTACACCACCTCCGTCTTCATGCCCTGGTGGGCCTCATCCTCCTGCTCACCGCCA
TGGTCCGCCTGGCCAACTGGATAGTGGATCAGATGCCCAGCAGGAACCGCGCCCCGCCGCTGCCAC
CGCCCCTCACCTATGTGGGACCCTGCGCCGAGGACCACATCTACGATGAGCCAACCGTAGGGCAAT
ACGTACAGATGAAGTAGCTCCCCCTCTTTCCCATTCCCCCATTTTTCTCTATTCAATAAAGTTGCT
TACCTGAGTTCATCCACACTCGGTCTGCCAGTGCAGTCTATCCATGCGCCGTTTTCCATACTCACA
TAGCGCAGCCGCGCACGCCTCGCCAGGTGACGAAACTGTCGAAATGTAACATTTCGCGCTTCTGTC
AGCAGCACCCCGTTATAGACCAGTTCCACCATGGGACCGAAGAAGCAGAAGCGCGAGCTACCCGAG
GACTTCGATCCAGTCTACCCCTATGACGTCCCGCAGCTGCAGATCAATCCACCCTTCGTCAGCGGG
GACGGATTCAACCAATCCGTGGACGGGGTGCTGTCCCTGCACATCGCACCGCCCCTCGTTTTGAC
AACACCAGGGCCCTCACCCTGGCCTTCGGGGGAGGTCTACAGCTCTCGGGCAAGCAGCTCGTCGTT
GCCACCGAGGGCTCGGGGCTAACCACCAACCCGGATGGCAAGCTGGTTCTCAAAGTCAAGTCCCCC
ATCACCCTGACCGCCGAGGGCATCTCCCTGTCCCTGGGTCCCGGTCTTTCTAACTCAGAGACCGGC

FIGURE 1-9

CTCAGTCTGCAAGTCACAGCTCCCCTGCAGTTCCAGGGCAACGCCCTCACTCTTCCCCTCGCCGCC
GGTCTCCAAAACACCGATGGTGGAATGGGTGTCAAACTGGGGAGCGGTCTCACCACGGACAACAGT
CAGGCGGTGACCGTTCAGGTGGGAAATGGACTTCAGCTGAACGGCGAAGGACAACTCACCGTCCCC
GCCACGGCCCCTTTAGTCTCAGGGAGCGCAGGCATCTCTTTCAACTACTCCAGCAATGACTTCGTC
TTAGACAATGACAGTCTCAGTTTGAGGCCAAAGGCCATCTCTGTCACCCCTCCGCTGCAGTCCACA
GAGGACACAATCTCCCTGAATTATTCTAACGACTTTTCTGTGGACAATGGCGCCCTCACCTTGGCT
CCAACTTTCAAACCCTACACGCTGTGGACTGGCGCCTCACCCACAGCAAATGTCATTCTAACAAAC
ACCACCACTCCCAACGGCACCTTTTTCCTATGCCTGACACGTGTGGGTGGGTTAGTTTTGGGTTCC
TTTGCCCTGAAATCATCCATCGACCTTACTAGTATGACCAAAAAGGTCAATTTTATTTTTGATGGG
GCAGGTCGGCTTCAGTCAGACTCCACTTATAAAGGGAGATTTGGATTTAGATCCAACGACAGCGTA
ATTGAACCCACAGCCGCAGGACTCAGTCCAGCCTGGTTAATGCCAAGCACCTTTATTTATCCACGC
AACACCTCCGGTTCTTCCCTAACATCATTTGTATACATTAATCAGACATATGTGCATGTGGACATC
AAGGTAAACACACTCTCTACAAACGGATATAGCCTAGAATTTAACTTTCAAAACATGAGCTTCTCC
GCCCCCTTCTCCACCTCCTACGGGACCTTCTGCTACGTGCCCCGAAGGACAACTCACCGTCCCCGC
CACGGCCCCTTTAGTCTCAGGGAGCGCAGGCATCTCTTTCAACTACTCCAGCAATGACTTCGTCTT
AGACAATGACAGTCTCAGTTTGAGGCCAAAGGCCATCTCTGTCACCCCTCCGCTGCAGTCCACAGA
GGACACAATCTCCCTGAATTATTCTAACGACTTTTCTGTGGACAATGGCGCCCTCACCTTGGCTCC
AACTTTCAAACCCTACACGCTGTGGACTGGCGCCTCACCCACAGCAAATGTCATTCTAACAAACAC
CACCACTCCCAACGGCACCTTTTTCCTATGCCTGACACGTGTGGGTGGGTTAGTTTTGGGTTCCTT
TGCCCTGAAATCATCCATCGACCTTACTAGTATGACCAAAAAGGTCAATTTTATTTTTGATGGGGC
AGGTCGGCTTCAGTCAGACTCCACTTATAAAGGGAGATTTGGATTTAGATCCAACGACAGCGTAAT
TGAACCCACAGCCGCAGGACTCAGTCCAGCCTGGTTAATGCCAAGCACCTTTATTTATCCACGCAA
CACCTCCGGTTCTTCCCTAACATCATTTGTATACATTAATCAGACATATGTGCATGTGGACATCAA
GGTAAACACACTCTCTACAAACGGATATAGCCTAGAATTTAACTTTCAAAACATGAGCTTCTCCGC
CCCCTTCTCCACCTCCTACGGGACCTTCTGCTACGTGCCCCAGAGTGCCTAGAGAACCCTGGCCGT
CAGCCGGCCTCCCCCTTCCCAGGCCACCCGGTACACCACCCGCTCCATGTTTCTGTATGTGTTCTC
CTCCCGCCGCTTGTGCAGCACCACCTCCCGCTGCTCGAGCTGAGGATCCGTGATGGACACAAAGCC
AGGAAGACACATCCTCAGCTCCGTGGGGGCGTCCAACAACTGTTTATGTAAAGGAAAATAAAGACT
CAGAGAAAATCCAAGTTCATATGATTTTTCTTTTATTGATTGGGGGAATTGATTCAGGTGGGGTGT
GCATAATCACAAAAATCACATCAGCAGGTACACACCTGAGACATCAGACAGGGGTAAGGACAGCGC
CTCAGCTTCTGGAACAGACATCAGAAATATTTAATCTGCTGGTAGCTAACACTCCTTCCCAACACC
ATACACTCCTGGAGGGCCCTCTGCCTCTCCTCCTCCCGCTCCGCGTCCCTCTGCCGGGACCACCAC
TCCCCCTCCGTGAACTGCTGCTTCCTCCCCCGCCGCTGCGCCCCGATGGCCTCCGCCGCCAGCTTC
AGCCAGTGCCGCAAGCGCTGGGCGCAGCGCCGAGCCACCGGCTCGCTCAGCTCGTGGCAGCGCCGG
CACACCAGCACTATGTAATTGGCATAGTCCCCGTCACAGTAGATGACCTCCCCCCAGTGGAACATG
CGCAACAGCTTCAGATCACAGTCATACATGATCTTTATGTACATCAGGTGGGCGCCTCGAAACATC
ACACTGCCCACGTACATCACGCGACTCACGCTGGGCAGGTTCACCGCCTCCCTGAACCACCAGAAG
ATGCGATTGTACTCGCAGCCCCGGATGATCTCGCGCATCAGGGAGCGCATCACCACCTGCCCCGCG
CGGCACTCCAGACTGGACCTTTTCAGACAGTGGCAATGAAAGTTCCACAGCGTCGCGCCCGCACAG
CGTCTCCGGGCTGAAACATATCTGCTCCAGCTCCAACCCCCCACACAGGCTGTACTGCAGGAAAAT
CCATTCTTGATGGGAAAGGATGTAGCGCCAGGGGACCACAATCTCCAAACAGGGAACAAAACATAC
CGCGGCCCGGCTGTTGCGCACGGCCCCCACCGGATGCAACGTGCTCACGGAGCAGATACGGGTGGG
ACAGCGGCCCACGTCTCATAGCAAGTCAAGTCCGGAAGTGGCACGGGGTTCGCCACCACTGCTACT
GCTGCCGCTGCGCCACCAGCTCCATCGGCTCCTCCATCCTCCTCCTGTTCCATCGGCTGAGGTGCT
GCCTCCTCCTCCTCCTGCCGCTGCTCCATCATGCTCGTCTGCGGTCATCAGGAGTCAAAAAATTCA
TTGGCCACCGCACGCAGAGAGAACATGGAGCGCAGGGGCCCAGGTGCCCGGCCCGTGCGCTCGCTC
AACTCCCCCAGCAGGTACTCATAGAGATGCTCCTCCAAATCCACCGCAAACCAGGCATGCAGAAAC
TCTTCCGTTCGAGGACCGCCCACGGTAAAGACATAGCCCTCCCGCACCTTCACCGCTGCCAGCTGC
ACGCGCTCATGTCGCTGGGAGTACACCCGGACCCGGGCCTGGATGTACTCCAGCACCTGATCGCTC
AGACACCTCACAGAGATGCCAGCCTGAGCCAGCTTCTCATAGAGAGGTGGCTGAATCTTGAGCTTG
AAGCAGCGAGCGGCTAGGCACTCCCCGCCCCCTTGGAACAGGGCGGCCGGGTCAGCCATGGACTTC
CTCTACATCCGGGGTCCTGGCCACCTCACAAACTATCTGGCCAATCGCCTGACCACGGGTCACCAG
GTAAGGATGATGTCCGTTGTTGCGAATGAGAATGCTCAGAGGTGACTCGGTAGCGTTATCAATCAC
GTCCCCAAAGGTCCAAAGGTCCCAGTTAGAAGTCAGGTGCTTCAGACCGCAGACACGCCCATAGCA
ACCAGTGGGAAAAGCCAGCAAGAGATCCGTGGGCACATGCACCGAAGCTCCCGCAGGAATCTCCAC
CCACTCCGAGGCGTAGACCGTGTAAGCTACACACCCCGCCTCCCGAGTGGGAGCAGAAGCATTCTC

FIGURE 1-10

GCTCAGCCGAAAGAACTTCAGGGTGGCCTGCATATCCTCTTTTACTCACTTGTTAGCAGCTCCACA
CAGACCAGGGTTGTGTTGGCGGGAATAGGCAGCAGGGGTACGTCCCCAGTGAGGGACACCTGGATG
GGGGGCAGAGGATTGATGCCAGGAAGCAGCAGGTACTGGGAAACAGAGACCAGATCCCTCCTCTGA
AAAATCTCGCTCAGTCGGACAAACACAGCAAACCCAGTGGGCACGTAGACTAGCACATTAAAAAGG
ATCACGCTGGGCTGTTCTGACGTCAGCACCAGATGTCGGGACGTGCGCAGATGAATGCGGTTCTGA
TGAATTACCGGAGGCCTCTCACCCGCAGCCAACAGCAGACCGGGCTGCTGATGCGGTCCCGCAGAC
ATATATGAGTTCAATGTGTGTCTTTTTTCTAAACGTCTAGTGAGTGTGCTCGTCCTGCTCCTGCCA
ATCAAAATCCGGGCACCAGGGCTGGTGGTTGGACCCGATGAAGAAGCGAGGAGAGGCGGCCTCCTG
AGTGTGAAGAGTGTCCCGATCCTGCCACGCGAGGTAGGCGAAGTACAGATAGAGCACGGCGAGAAC
AGTCAGCACCGCGGCCAGCAGCAGTCGGTCGTGGGCCATGAGAGGGGGCTGATGGAAGATGGCCG
GTGACTCCTCTCGCCCCGCTTTCGGTTTCTCCTCGTCTCGCTCTCAGTGTCTCTCTCTGTGTCAGC
GCCGAGACGAGTGTGAGCGAACACCGCGAGCGGGCCGGTGATATACCCACAGCGGATGTGGCCACG
CCTGCGGTCGGTTAATCAGTACCCCATCGTCCGATCGGAATTCCCCCGCCTCCGCGTTAACGATTA
ACCCGCCCAGAAGTCCCGGGAATTCCCGCCAGCCGGCTCCGCCGCGACCTGCGACTTTGACCCCGC
CCCTCGGACTTTGACCGTTCCCACGCCACGTCATTTTCCCACGCGACGTCACGTTCCCACGCTACG
TCACACCCCTCTCCACCAATCACCGCCCGCCGCCCCCAACCCTCTCCGCCAATCACCACGCCACAA
AAGGGGCAATAAAAGTGTGCGGTATATTATTGATGATG 1 2 3 4
FIG._3A
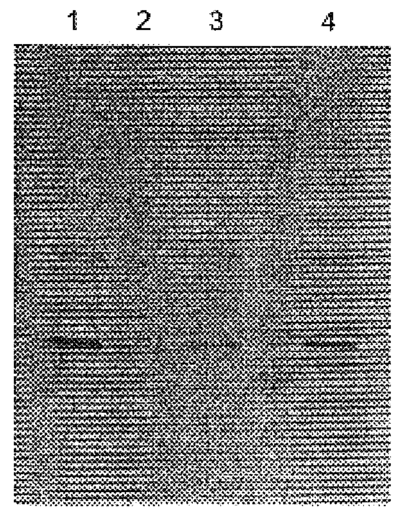
FIG._3B
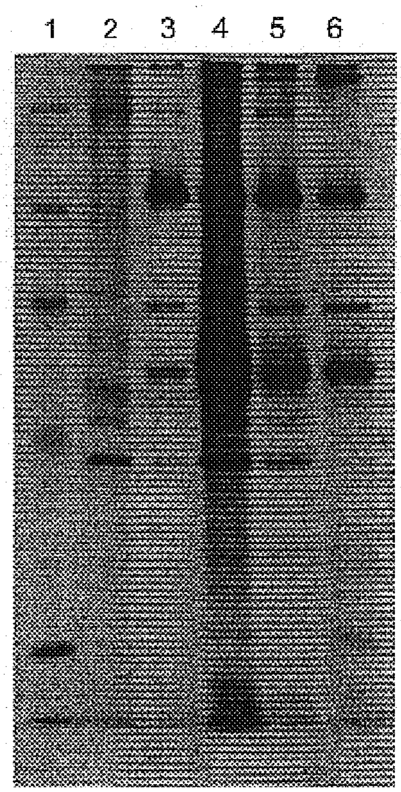
FIG._7 pPAVXhoIRL
YZ13
YZ14
YZ15
YZ16
PCR
BamHI-SpeI
SpeI- Bsu36
BamHI
Bsu36
XhoI
BamHI- Bsu36 cut
Three way ligation
SpeI
pYZ20
XhoI
XhoI cut
PAV E3 viral DNA
Homologous recombination in BJ5183
pFPAV211
PacI
(B)

AseI
SpeI
pYZ20
AseI
XhoI
SpeI cut,
ligate to PmeI linker
AseI
PmeI
pYZ20
AseI
XhoI
AseI cut
Isolate 1424 bp fragment
AseI
SpeI SpeI
pYZ37
AseI
XhoI
AseI cut
Isolate 6774 bp fragment
Ligate
AseI
PmeI SpeI
pYZ39
AseI
XhoI
PmeI cut, ligate to 1.7 kb GFP casette
SpeI
pYZ42
XhoI
XhoI cut
XhoI
XhoI
PAV E3 viral DNA
Homologous recombination in BJ5183
PacI
SpeI
pFPAV216
PacI
(F)

Figures 22A-22C:Full-length plasmids with E4 deletions 0
10
20
30
40
50
60
70
80
90
100mu 92mu
TATA (33774-33771)
AATAAAA
31189-31183
ITR
33636
Orf1
33436
33401
Orf2
33045
33036
Orf3
32659
32666
Orf4
32256
32240
Orf5
32055
32095
Orf6
31835
Orf7
31796
31305

Dorf1
Dorf1&2
Dorf2
Dorf2&3
Dorf3
Dorf3&4
Dorf4
Dorf4&5
Dorf5
Dorf5&6
Dorf6
Dorf6&7
Dorf7

| Mutant Viruses | 401 | 412 | 402 | 404 | 445 | 405 | 456 | 406 | 467 | 407 | WT |
|---|---|---|---|---|---|---|---|---|---|---|---|
| Expected | 466 | 466 | 699 | 1436 | 1436 | 1855 | 1855 | 2049 | 2049 | 2289 | |
| Sizes | 33436 | 33044 | 33044 | 32264 | 32103 | 32103 | 31834 | 31834 | 31303 | 31303 | 34097 |

PCR Analysis of Mutant Viruses

| | |
|---|---|
| PAV456 | 1029 bp |
| PAV406 | 1223 bp |
| PAV467 | 692 bp |
| PAV407 | 932 bp |
| WT | 1422 bp |

| | |
|---|---|
| PAV404 | 936 bp |
| PAV445 | 776 bp |
| PAV405 | 1194 bp |
| WT | 1333 bp |

| | |
|---|---|
| PAV401 | 814 bp |
| PAV412 | 423 bp |
| PAV402 | 665 bp |
| WT | 1009 bp |

PORCINE ADENOVIRUS E1 AND E4 REGIONS

CROSS-REFERENCED TO RELATED APPLICATIONS

This is a continuation-in-part application of U.S. patent application Ser. No. 09/963,038, filed Sep. 24, 2001, abandoned, which is incorporated by reference herein in its entirety.

TECHNICAL FIELD

The present invention is in the field of recombinant mammalian viral vectors. More particularly, it concerns recombinant porcine adenovirus vectors for diagnostic and therapeutic purposes, such as for vaccines, gene delivery and expression systems.

BACKGROUND

Adenoviruses are double-stranded DNA viruses that have been isolated from a wide variety of avian and mammalian species, including swine. Porcine adenoviruses (PAV) belong to the *Mastadenovirus* genus of Adenoviridae family. Of the five serotypes identified till date (Derbyshire et al., 1975, *J. Comp. Pathol.* 85:437-443; Hirahara et al., 1990, Japanese *J. Vet Sci.* 52:407-409), serotype 3 (PAV-3) could propagate to high titers in cell culture. While the majority of adenovirus infections in swine are subclinical, porcine adenovirus (PAV) infection has been associated with encephalitis, pneumonia, kidney lesions and diarrhea. Derbyshire (1992) In: "Diseases of Swine" (ed. Leman et al.), 7th edition, Iowa State University Press, Ames, Iowa. pp. 225-227. Thus, there is a need for vaccines that will provide protection against PAV infection.

In addition to their potential ability to provide protection against PAV infection, PAVs could also be used as viral vaccine vectors, if insertion capacity can be determined, and appropriate insertion sites can be defined and characterized. It has been shown that PAV is capable of stimulating both humoral response and a mucosal antibody responses in the intestine of infected piglets. Tuboly et al. (1993) *Res. in Vet. Sci.* 54:345-350. Thus, recombinant PAV vaccine vectors would be especially useful, as they would be likely to be capable of providing both systemic and mucosal immunity to antigens encoded by native and/or recombinant PAV genomes.

Cross-neutralization studies have indicated the existence of at least five serotypes of PAV. Derbyshire et al. (1975) *J. Comp. Pathol.* 85:437-443; and Hirahara et al. (1990) *Jpn. J. Vet. Sci.* 52:407-409. Previous studies of the PAV genome have included the determination of restriction maps for PAV Type 3 (PAV-3) and cloning of restriction fragments representing the complete genome of PAV-3. Reddy et al. (1993) *Intervirology* 36:161-168. In addition, restriction maps for PAV-1 and PAV-2 have been determined. Reddy et al. (1995b) *Arch. Virol.* 140:195-200.

Nucleotide sequences have been determined for segments of the genome of various PAV serotypes. The transcription map and complete DNA sequence of PAV-3 genome was reported (Reddy et al., 1998, *Virus Res,* 58:97-106 and Reddy et al., 1998, *Virology* 251:414-426). Sequences of the E3, pVIII and fiber genes of PAV-3 were determined by Reddy et al. (1995a) *Virus Res.* 36:97-106. The E3, pVIII and fiber genes of PAV-1 and PAV-2 were sequenced by Reddy et al. (1996) *Virus Res.* 43:99-109; while the PAV-4 E3, pVIII and fiber gene sequences were determined by Kleiboeker (1994) *Virus Res.* 31:17-25. The PAV-4 fiber gene sequence was determined by Kleiboeker (1995b) *Virus Res.* 39:299-309. Inverted terminal repeat (ITR) sequences for all five PAV serotypes (PAV-1 through PAV-5) were determined by Reddy et al. (1995c) *Virology* 212:237-239. The PAV-3 penton sequence was determined by McCoy et al. (1996a) *Arch. Virol.* 141:1367-1375. The nucleotide sequence of the E1 region of PAV-4 was determined by Kleiboeker (1995a) *Virus Res.* 36:259-268. The sequence of the protease (23K) gene of PAV-3 was determined by McCoy et al. (1996b) *DNA Seq.* 6:251-254. The sequence of the PAV-3 hexon gene (and the 14 N-terminal codons of the 23K protease gene) has been deposited in the GenBank database under accession No. U34592. The unpublished sequence of the PAV-3 100K gene has been deposited in the GenBank database under accession No. U82628. The sequence of the PAV-3 E4 region has been determined by Reddy et al. (1997) *Virus Genes* 15:87-90.

Adenoviruses have proven to be effective vectors for the delivery and expression of foreign genes in a number of specific applications, and have a number of advantages as potential gene transfer and vaccine vectors. See Gerard et al (1993) *Trends Cardiovasc. Med.* 3:171-177; Imler et al. (1995) *Hum. Gene Ther.* 6:711-721. The ability of these vectors to mediate the efficient expression of candidate therapeutic or vaccine genes in a variety of cell types, including post mitotic cells, is considered an advantage over other gene transfer vectors. Adenoviral vectors are divided into helper-independent and helper-dependent groups based on the region of the adenoviral genome used for the insertion of transgenes. Helper-dependent vectors are usually made by deletion of E1 sequences and substitution of foreign DNA, and are produced in complementing human cell lines that constitutively express E1 proteins. Graham et al. (1977) *J. Gen. Virol.* 36:59-74; Fallaux et al. (1996) *Hum. Gene Ther.* 7:215-222; Fallaux et al. (1998) *Hum. Gene Ther.* 9:1909-1917. However, porcine adenoviruses do not replicate in human cell lines; hence these lines are unsuitable for the propagation of E1-deleted PAV vectors. E1A region is described in Darbyshire (1966, *Nature* 211:102) and Whyte et al., 1988, *J. Virol.* 62:257-265.

Though E1-deleted viruses do not replicate in cells that do not express E1 proteins, the viruses can express foreign proteins in these cells, provided the genes are placed under the control of a constitutive promoter. Xiang et al. (1996) *Virology* 219:220-227. Vaccination of animals with adenovirus recombinants containing inserts in the E1 region induced a systemic immune response and provided protection against subsequent challenge. Imler et al (1995) *Hum. Gene Ther.* 6:711-721; Imler et al. (1996) *Gene Therap* 3:75-84. This type of expression vector provides a significant safety profile to the vaccine as it eliminates the potential for dissemination of the vector within the vaccine and therefore, the spread of the vector to non-vaccinated contacts or to the general environment. However, the currently used human adenovirus (HAV) based vectors are endemic in most populations, which provides an opportunity for recombination between the helper-dependent viral vectors and wild type viruses. To circumvent some of the problems associated with the use of human adenoviruses, non human adenoviruses have been explored as possible expression vectors.

Use of vectors containing an intact E1 region for gene therapy in humans and vaccination in animals is unsafe because they have the ability to replicate in normal cells and spread to other animals, and they retain any oncogenic potential of the E1 region. WO 99/53047 disclose the use of PAV vectors deleted in their E1 region. See Klonjkowski et al (1997) *Hum. Gene Ther.* 8:2103-2115 which discloses E1 deleted canine adenovirus 2.

There remains a need for improved adenoviral vectors for expression of transgenes in mammalian cells, and for the development of effective recombinant PAV vectors for use in immunization and expression systems.

SUMMARY OF THE INVENTION

The present invention relates to the characterization of the porcine adenovirus E1 and E4 regions. The present invention discloses the complete nucleotide sequence of the genome of porcine adenovirus type 3 (PAV-3) and provides the characterization of the PAV3 E1 region, including E1A, E1B$^{small}$, E1B$^{large}$ and E4 region ORF1-ORF7. As shown herein, E1A, E1B$^{large}$ and E4 ORF3 are essential for replication of PAV3. Nucleic acid sequences that are substantially homologous to those comprising a PAV genome are also encompassed by the invention. Substantially homologous sequences include those capable of duplex and/or triplex formation with a nucleic acid comprising all or part of a PAV genome (or with its complement). As is known to those of skill in the art, duplex formation is influenced by hybridization conditions, particularly hybridization stringency. Factors affecting hybridization stringency are well-known to those of skill in the art. See, for example, Sambrook et al. (1989) Molecular Cloning: A Laboratory Manual; Hames et al. 1985) Nucleic Acid Hybridisation: A Practical Approach, IRL Press Ltd., Oxford Accordingly, it is within the skill of the art to identify a sequence that is substantially homologous to a sequence from a PAV genome.

In particular, the present invention provides a replication-defective recombinant PAV vector, comprising at least one heterologous nucleotide sequence, wherein the PAV vector lacks E1A and/or E1B$^{large}$ function and retains E1B$^{small}$ function. In some embodiments, the vector comprises a deletion of part or all of the E1A and/or E1B$^{large}$ gene region. In other embodiments, the vector comprises an insertion in the E1A and/or E1B$^{large}$ gene region that inactivates the E1A and/or E1B$^{large}$ region function. In some embodiments, the vector further comprises a deletion of part or all of the E3 region, or other essential or non-essential regions of the adenovirus. In additional embodiments, the PAV is PAV3.

In yet other embodiments, the present invention provides a replication-defective recombinant PAV vector that comprises a deletion in the E1 region that consists of a deletion of the E1A and/or E1B$^{large}$ region. In yet other embodiments, the present invention provides a replication-defective recombinant PAV vector that comprises an insertion in the E1 region that consists of an insertion in the E1A and/or E1B$^{large}$ region that inactivates E1A and/or E1B$^{large}$ region function.

The present invention also provides a replication-defective recombinant PAV vector comprising at least one heterologous nucleotide sequence, wherein the PAV vector lacks E1A function and E1B$^{small}$ function and retains E1B$^{large}$ function. In some embodiments, the vector comprises a deletion of part or all of the E1A and E1B$^{small}$ regions. In other embodiments, the vector comprises an insertion that inactivates the E1A or E1B$^{small}$ gene region function. In further embodiments, the vector has a deletion of part or all of the E3 region, and/or part or all of non-essential E4 region and/or or other non-essential regions of the adenovirus.

In further embodiments, the present invention provides a PAV vector comprising at least one heterologous nucleotide sequence, wherein said vector lacks E1B$^{small}$ function and retains E1A and E1B$^{large}$ function. In some embodiments, the vector comprises a deletion of part or all of the E1B$^{small}$ region. In further embodiments, the vector comprises a deletion in the E3 region or other non-essential regions. In additional embodiments, the PAV is PAV3.

In other embodiments, the present invention provides a replication-defective PAV vector that lacks E4 ORF3 function. In some examples, the vector comprises a deletion of part or all of the E4 ORF3 region. In some examples, the vector comprises an insertion in the E4 ORF3 region that inactivates E4 ORF3.

In further embodiments, the heterologous nucleotide sequence encodes a therapeutic polypeptide. In yet further embodiments, the heterologous polypeptide sequence encodes an antigen. In yet further embodiments, the therapeutic polypeptide is selected from the group consisting of coagulation factors, growth hormones, cytokines, lymphokines, tumor-suppressing polypeptides, cell receptors, ligands for cell receptors, protease inhibitors, antibodies, toxins, immunotoxins, dystrophins, cystic fibrosis transmembrane conductance regulator (CFTR), immunogenic polypeptides and vaccine antigens.

The present invention also provides host cells infected with a recombinant PAV vector of the present invention. The present invention also provides methods for producing a recombinant PAVs that comprises introducing a PAV vector that lacks E1A function and/or E1B$^{large}$ function and retains E1B$^{small}$ function into a helper cell line that expresses E1A function and/or E1B$^{large}$ function and recovering virus from the infected cells. In one embodiment, the present invention comprises introducing a PAV vector that lacks E1A function, and retains E1B$^{small}$ and E1B$^{large}$ function, into a helper cell line that expresses E1A function. In some embodiments, the helper cell line expresses human E1A function.

The present invention also provides recombinant mammalian cell lines that comprise nucleic acid encoding mammalian adenovirus E1A function and lack nucleic acid encoding mammalian adenovirus E1B$^{small}$ function. In some embodiments, the E1A function is human E1A function. The present invention also provides recombinant mammalian cell lines that comprise nucleic acid encoding mammalian adenovirus E1B$^{large}$ function and lack nucleic acid encoding mammalian adenovirus E1B$^{small}$ function. In some embodiments, the E1B$^{large}$ function is human E1B$^{large}$ function. In other embodiments, the helper cell line expresses porcine E1B$^{large}$ function. In some embodiments, the cell line is of porcine origin. The present invention also provides methods for producing a recombinant PAV that lacks E1A and retains E1B$^{small}$ function. The present invention also provides recombinant mammalian cell lines that comprise nucleic acid encoding porcine E4 ORF3 function.

In some embodiments, the present invention provides a method comprising introducing, into an appropriate helper cell line, a porcine adenovirus vector comprising ITR sequences, PAV packaging sequences, and at least one heterologous nucleotide sequence, wherein said vector lacks E1A and/or E1B$^{large}$ function and retains E1B$^{small}$ function; culturing the cell line under conditions whereby adenovirus virus replication and packaging occurs; and recovering the adenovirus from the infected cells. In some embodiments, the PAV is PAV3. The present invention also provides methods for producing a recombinant PAV that lacks E1B$^{small}$ function and retains E1A and/or E1B$^{large}$ function.

The present invention provides viral particles comprising a PAV vector of the present invention. The present invention also provides host cells comprising a PAV vector of the present invention. In additional embodiments, the invention provides compositions that are able to elicit an immune response or able to provide immunity to PAV infection, through expression of antigenic PAV polypeptides. The invention also provides vectors comprising PAV genome sequences, including sequences encoding various PAV genes as well as PAV regulatory sequences, which are useful for controlling the expression of heterologous genes inserted into PAV vectors.

BRIEF DESCRIPTION OF THE DRAWINGS

FIGS. 1-1 through 1-10 show the complete nucleotide sequence of the PAV-3 genome (SEQ ID NO: 1).

FIG. 2 shows the transcriptional map of the PAV-3 genome derived from alignment of the sequences of cDNA clones with the genomic sequence, and nuclease protection mapping of viral transcripts. The PAV-3 genome is represented by the thick horizontal line, with the numbers below the line representing PAV-3 map units (i.e., percentage of genome length from the left end). Rightward-reading transcription units are depicted above the line and leftward-reading transcription units are shown below the line.

FIGS. 3A-3B show immunoprecipitation of E1A and E1B proteins from various cell lines. In FIG. 3A, proteins in cell lysates were separated by gel electrophoresis, and analyzed by immunoblotting using the DP11 monoclonal antibody, which recognizes the human adenovirus E1A protein. Lane 1: 293 cells (human cells transformed by HAV-5, which express adenovirus E1A and E1B); Lane 2: Fetal porcine retinal cells; Lane 3: VIDO R1 cells; Lane 4: 293 cells. In FIG. 3B, proteins in cell lysates were separated by gel electrophoresis, and analyzed by immunoblotting using the DP17 monoclonal antibody, which recognizes the human adenovirus E1B protein. Lane 1: human 293 cells; Lane 2: Fetal porcine retinal cells; Lane 3: VIDO R1 cells; Lane 4: 293 cells.

FIG. 4 shows a map of the plasmid pPAV-101.

FIG. 5 shows a map of the plasmid pPAV-102.

FIG. 6 shows a map of the plasmid pPAV-300.

FIG. 7 shows proteins labeled after infection of VIDO R1 cells with a recombinant PAV containing the PRV gp50 gene inserted in the E3 region. Labeled proteins were separated by gel electrophoresis; an autoradiogram of the gel is shown. Lane 1: Molecular weight markers of 30K, 46K, 69K and 96K, in order of increasing molecular weight. Lane 2: Mock-infected cells, 12 hours post-infection. Lane 3: PAV-3-infected cells, 12 hours post-infection. Lane 4: cells infected with a recombinant PAV containing the PRV gp50 gene, 12 hours post-infection. Lane 5: cells infected with a recombinant PAV containing the PRV gp50 gene, 16 hours post-infection. Lane 6: cells infected with a recombinant PAV containing the PRV gp50 gene, 24 hours post-infection.

FIG. 8 provides a schematic diagram of the construction of an E1- and E3-deleted PAV vector with a green fluorescent protein gene insertion.

FIG. 10 shows the immunoprecipitation of proteins synthesized by in vitro transcription and translation of plasmids. [$^{35}$S]-methionine labeled in vitro transcribed and translated pSP64-PE1A (lanes 7,9), pSP64-PE1Bs (lanes 4,6), pSP64-PE1B1 (lanes 1,3) and pSP64polyA (lanes 2,5,8) products before (lanes 3,6,9) and after immunoprecipitation with anti-E1A (lanes 8,9), anti-E1B$^{small}$ (lanes 5,6) and anti-E1B$^{large}$ (lanes 2,3) were separated on 10% SDS-PAGE gels under reducing conditions. The positions of the molecular weight markers are shown to the left of the panel.

FIGS. 15A-15B shows Virus titers of recombinant and wild-type PAV-3. Near-confluent monolayers of VIDO R1 (FIG. A) or Swine Testicular (ST) (FIG. B) cells were infected with recombinant or wild-type PAV-3. At different time points post infection, the cell pellets were freeze-thawed and virus was titrated on VIDO R1 cells as described in the text.

FIG. 16A shows a map of the plasmid used for stable transfection of the VIDO-R1 cell line. The plasmid contains the human CMV promoter, the internal ribosomal entry site (IRES), hygromycin B phosphotransferase gene and the gene for PAdV-3 E1B-large protein. FIG. 16B shows the total genomic DNA extracted from hygromycin-resistant cell clones was digested with HindIII and hybridized with the labeled 1.9 kb-HindIII fragment of pIREShyE1BL DNA containing the E1B-large gene.

Figures 18A, 18B:
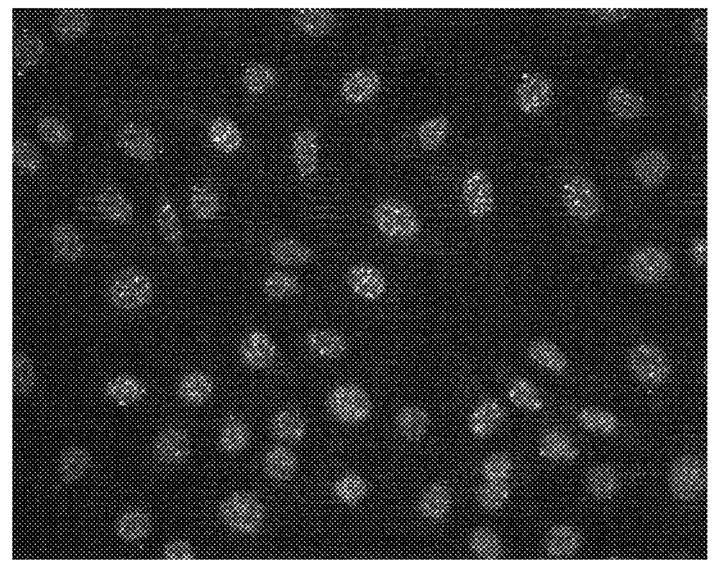
FIGS. 18A-18B show immunofluorescence of VR1BL cells. Immunofluorescence analysis was carried out using rabbit polyclonal antisera against PAdV-3 E1B-large protein.

The parent VIDO-R1 cell line is negative FIG. 18A. New VR1BL cell line is positive for PAdV-3 E1B-large protein expression FIG. 18B.

Figure 19A:
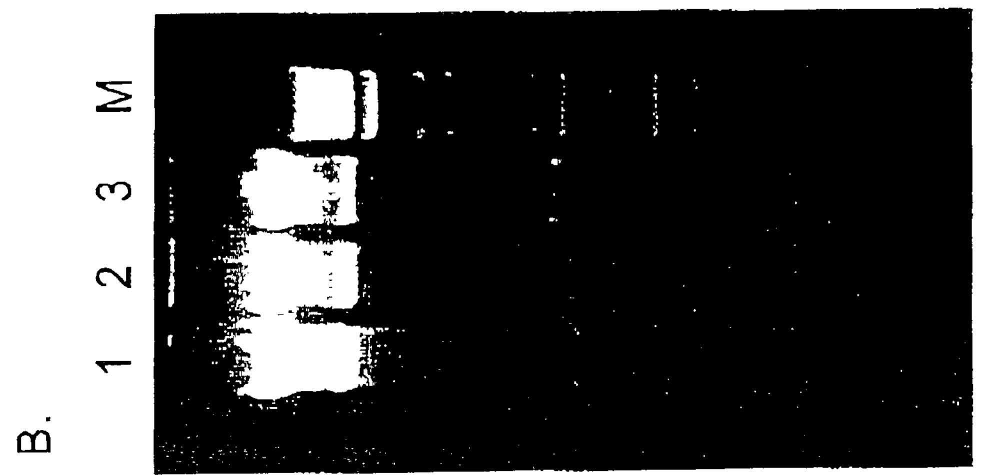
Figure 19B:
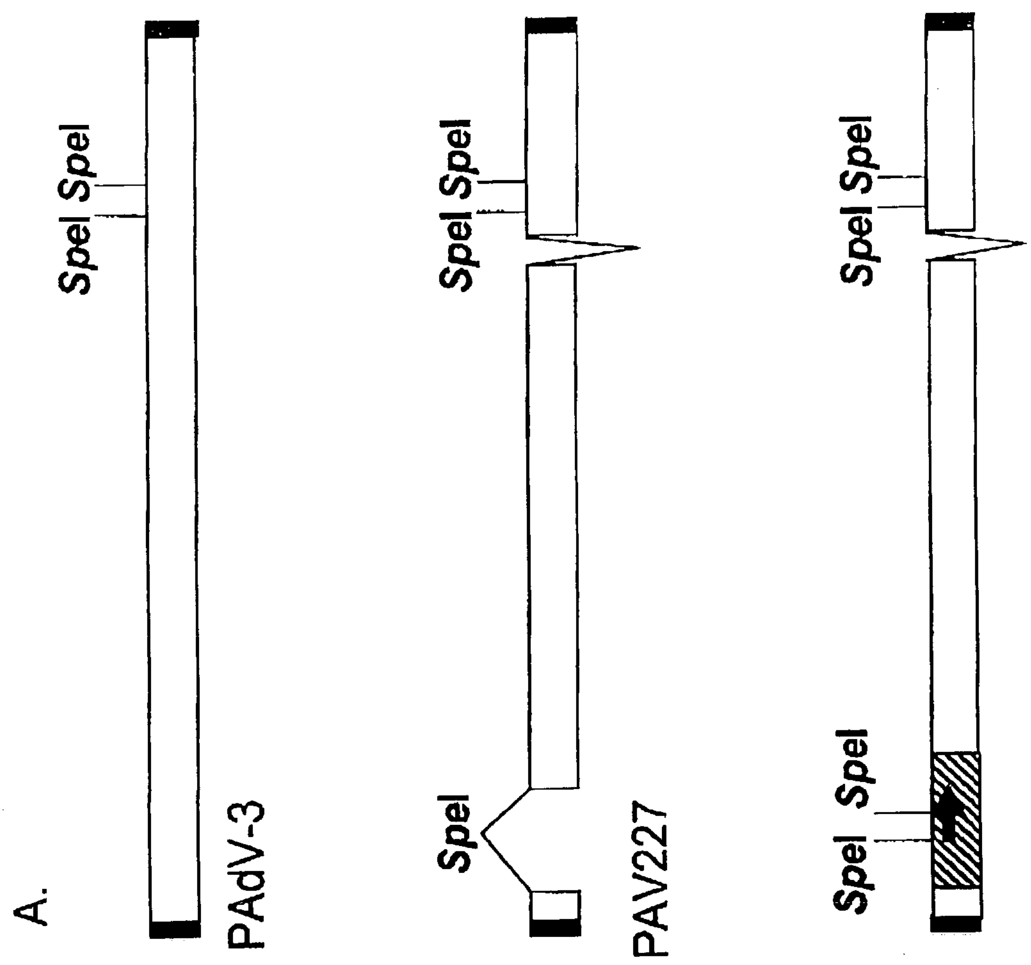

FIGS. 19A-19B. FIG. 19A shows a schematic representation of viral DNA. The origin of DNA sequences is as follows: PAdV-3 genome (open box); ITR (filled box); thin lines show the deletions in the E3 and E1 regions; GFP-expressing cassette, containing human CMV promoter, GFP gene, BGH polyA signal (hatched box). Arrow indicates the direction of the transcription of the GFP gene. FIG. 19B shows a restriction enzyme analysis of viral DNA. Recombinant viruses were rescued after transfection VR1BL cells with the full-length viral genomic DNA, cloned in plasmids. The viral DNAs were extracted from VR1BL cells infected with PAdV-3 (lane 1), PAV227 (lane 2), PAV219 (lane 3) digested with SpeI. Lane M is 1 kb+ marker.

Figure 20A:
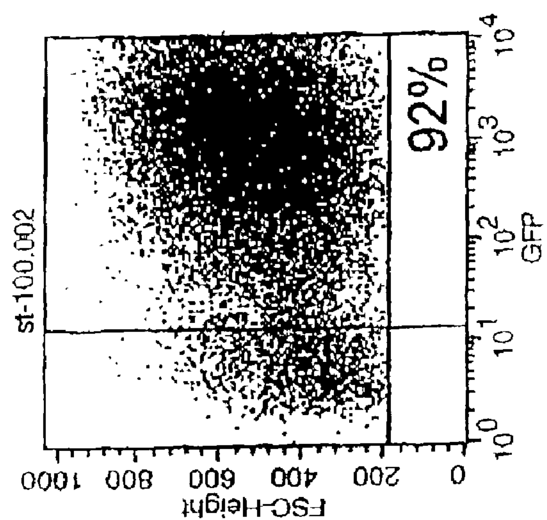
Figure 20B:
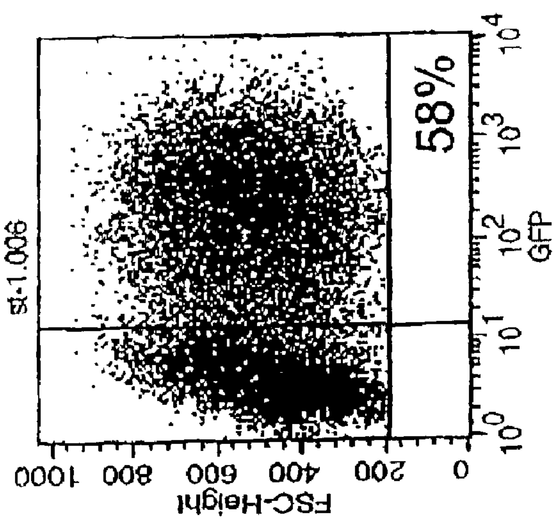
Figure 20C:
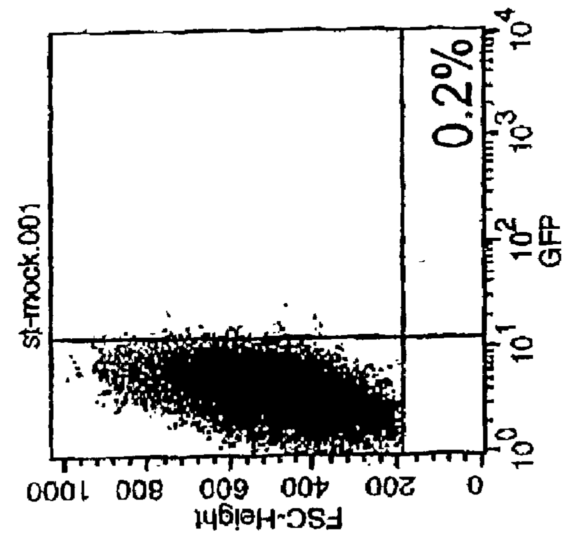

FIGS. 20A-20C. FIG. 20A shows GFP expression in PAV219 infected ST cells. To detect GFP expression by PAV219, ST (swine testis) cells were infected with m.o.i. 1 TCID50/cell FIG. 20B and 100 TCID50/cell FIG. 20C. 24 h.p.i. the cells were harvested and analyzed by FACS. FIG. 20A show mock-infected ST cells.

Figure 21:
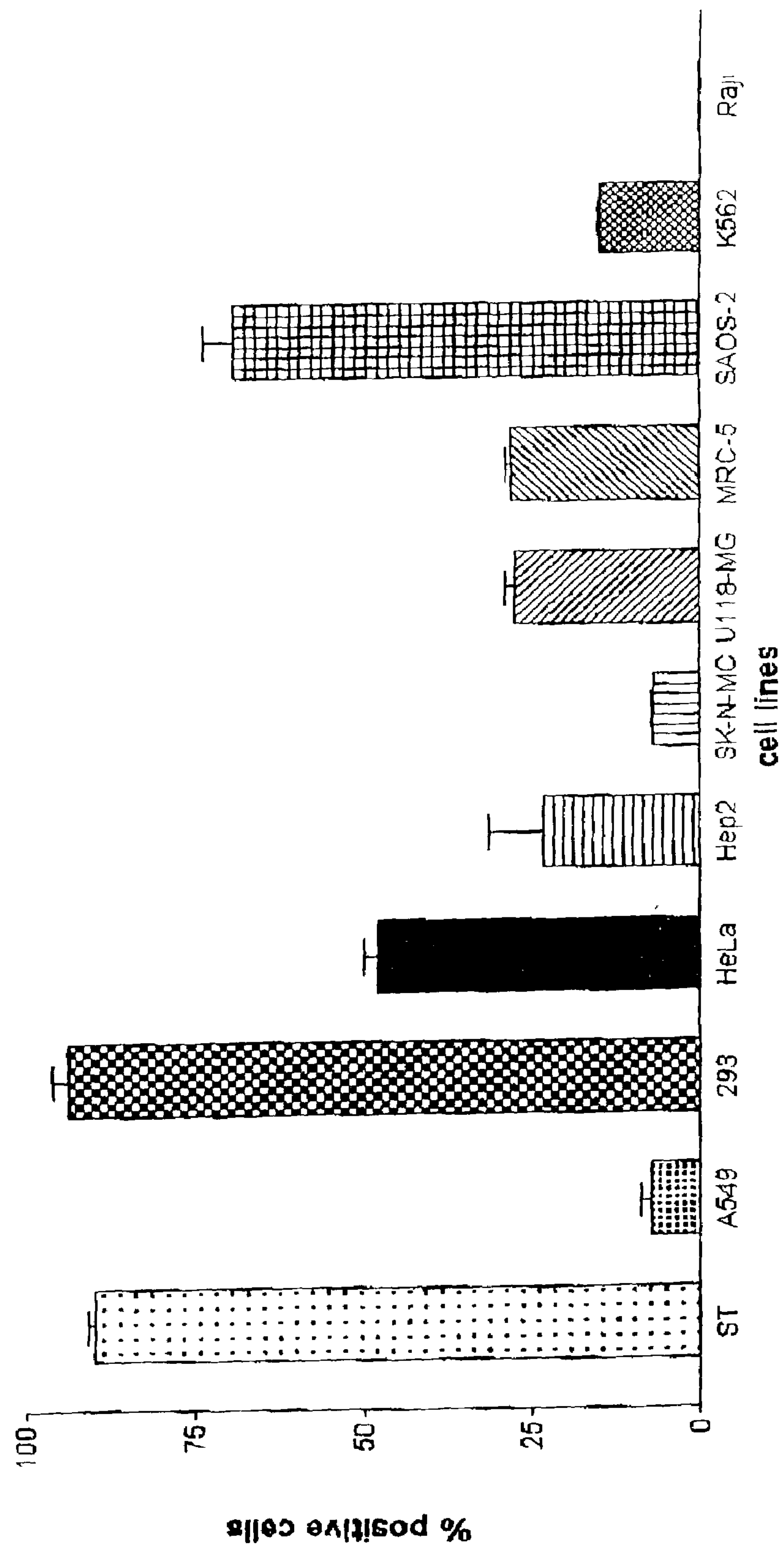

FIG. 21 shows transduction of human cell lines. Human cell lines were infected with PAV219 at m.o.i. 100 TCID50/cell. 24 h.p.i. the cells were harvested and GFP expression was analyzed by FACS. Tested human cell lines: A549 lung carcinoma; 293 embryo kidney; HeLa cervix carcinoma; Hep2 larynx carcinoma; SK-N-MC neuroblastoma; U118-MG glioblastoma; MRC-5 lung fibroblasts; SAOS-2 osteosarcoma; K562 myelogenous leukemia; Raji Burkitt's lymphoma. ST is a fetal porcine testis cell line.

Figures 22A, 22B, 22C:
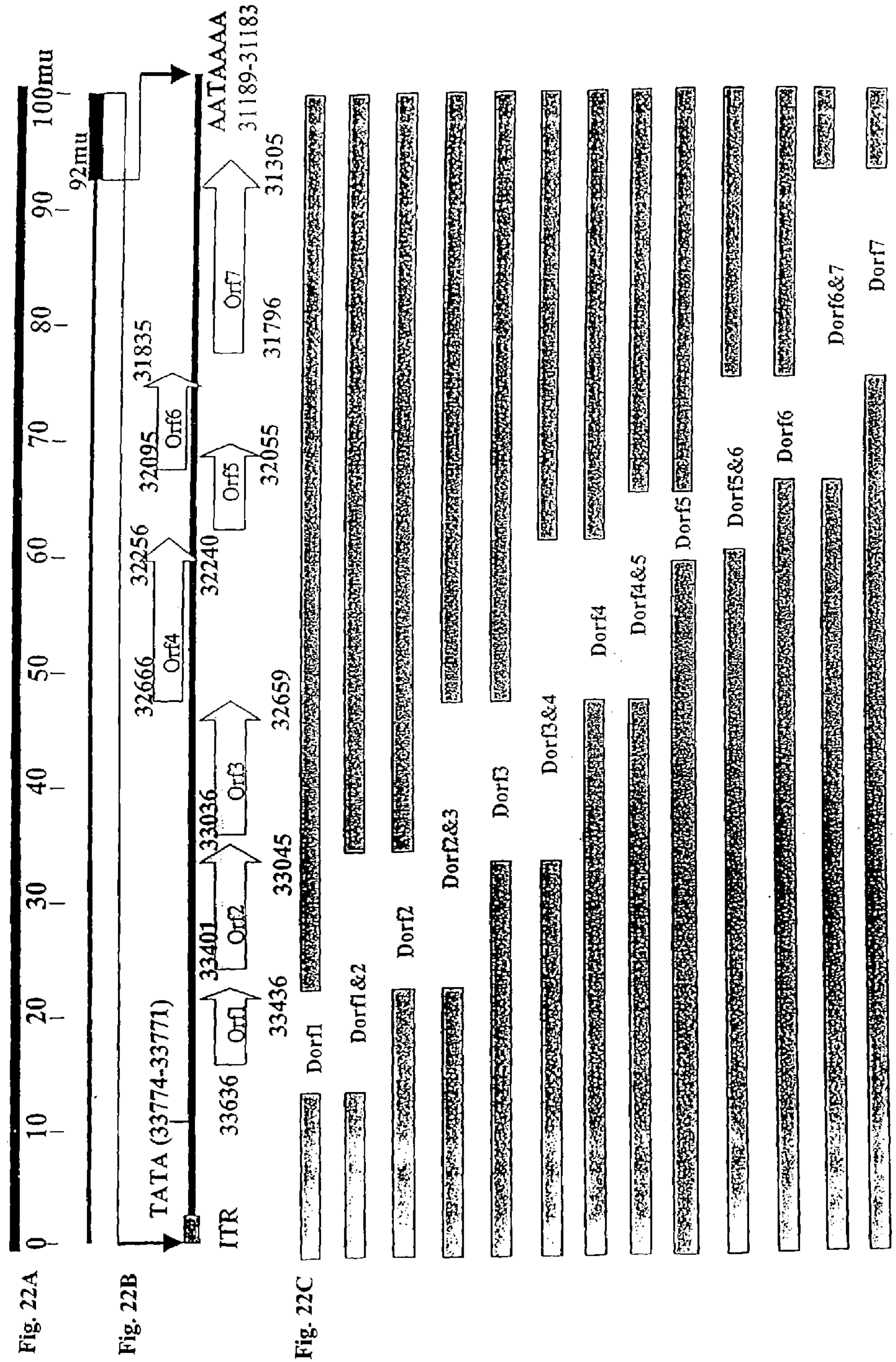

FIGS. 22A-22C show full-length plasmids with E4 deletions. FIG. 22A is the genomic map unit of PAV3. FIG. 22B shows the locations of the E4 TATA box, Poly A region and the seven putative open reading frames (ORFs). FIG. 22C shows the full-length clones with deletions of different ORFs.

Figure 23:
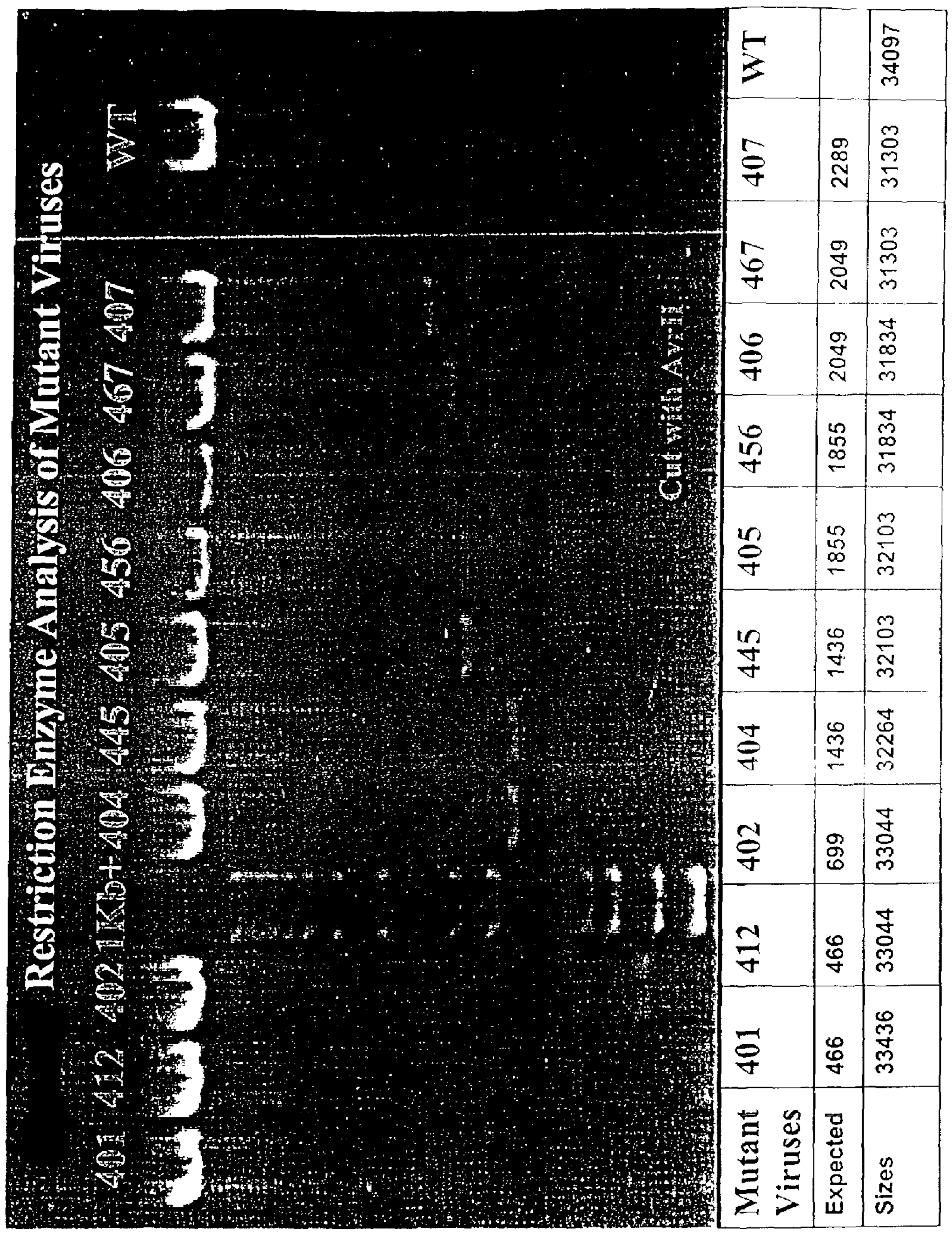

FIG. 23 shows the restriction enzyme analysis of the mutant viruses. ST cells were infected with mutant viruses and PAV3, and viral genomic DNAs were extracted from the infected cells. All the viral genomic DNAs were digested with AvrII, all the expected DNA fragment sizes generated upon digestion are shown below each of the mutant viruses. Molecular size markers of 1 kb+ are indicated.

Figure 24:
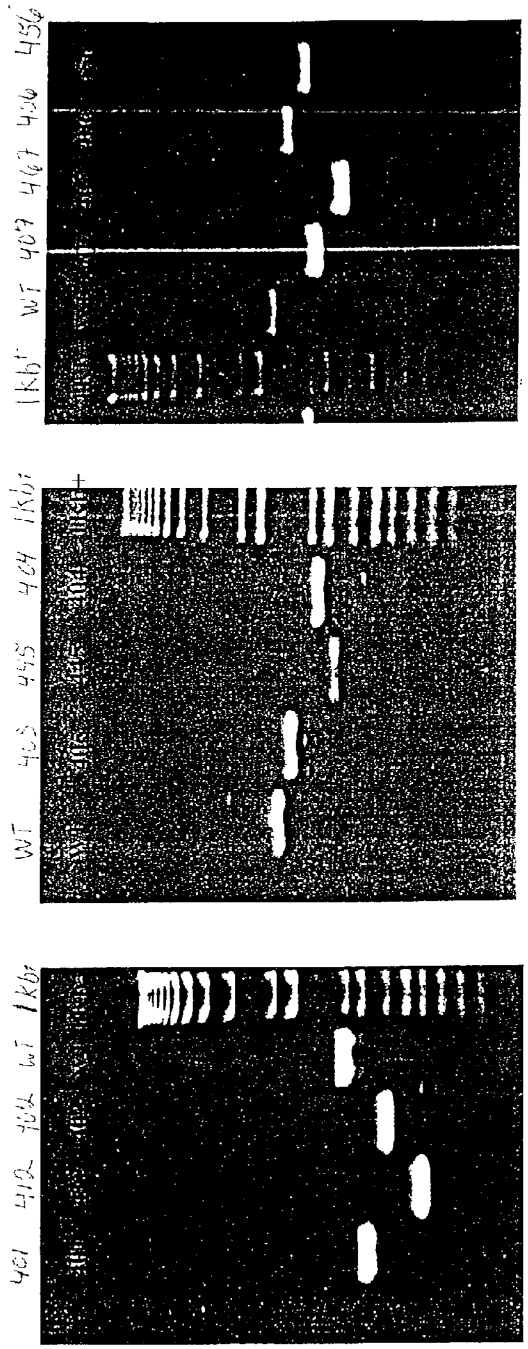

FIG. 24 shows the PCR analysis of mutant viruses. The PCR-amplified products from three different sets of primers flanking the corresponding E4 deletions are shown. The expected sizes of amplified products generated by PCRrom PAV3 and mutant viruses are also shown at the bottom. Molecular size markers of 1 kb+ are indicated.

Figure 25:
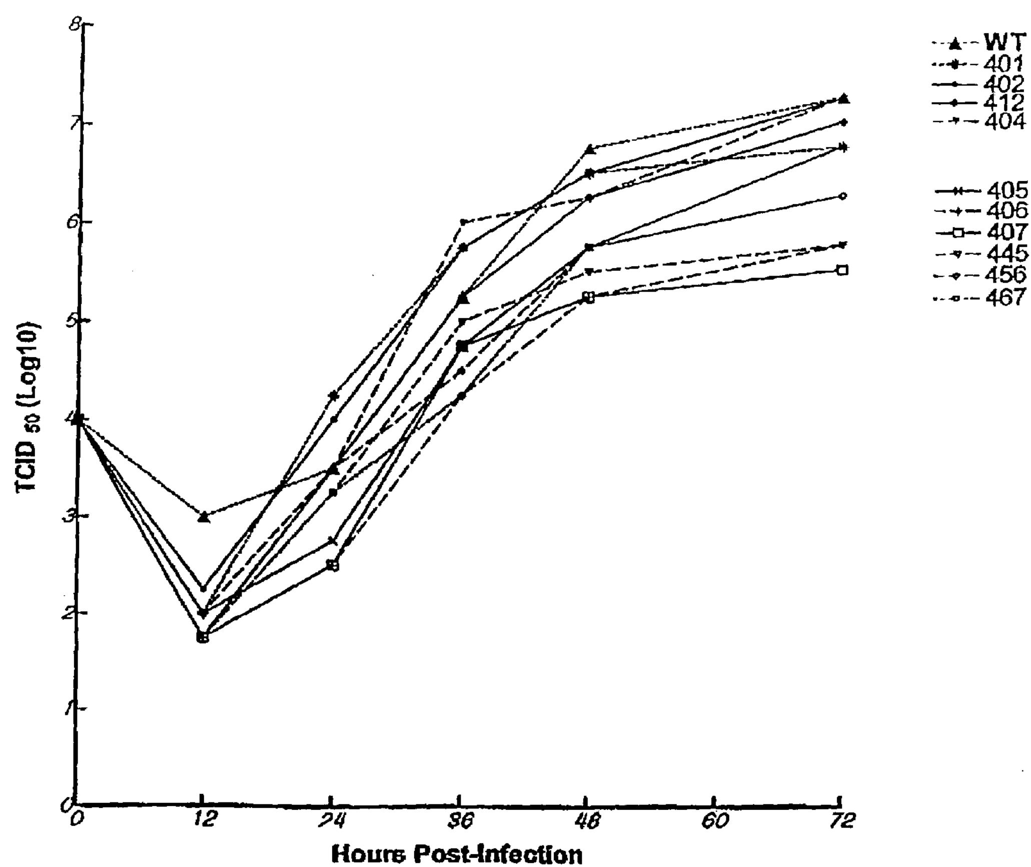

FIG. 25 shows the growth kinetics of PAV3 E4 mutant viruses.

DETAILED DESCRIPTION OF THE INVENTION

The present invention provides the complete nucleotide sequence and transcriptional map of the porcine adenovirus type 3 (PAV-3) genome and the characterization of the E1 region and E4 region of PAV3. In particular, the inventors have discovered that E1A and E1B$^{large}$ regions are essential for virus replication and E1B$^{small}$ is non-essential for virus replication. The inventors have discovered that E4 ORF 3 is essential for replication and E4 ORF1, ORF2, ORF4, ORF5, ORF6 and ORF7 are non-essential for replication. The PAV3 nucleotide sequence comprises a linear, double-stranded DNA molecule of about 34,094 base pairs, as shown in FIG. 1 (SEQ ID NO: 1). Previously-determined partial sequences can be aligned with the complete genomic sequence as shown in Table 1.

TABLE 1

Alignment of published PAV-3 sequences

| GenBank Accession No. | PAV Gene(s) included within sequence | Reference | Genome coordinates |
|---|---|---|---|
| L43077 | ITR | Reddy et al., 1995c | 1–144 |
| U24432 | penton | McCoy et al., 1996a | 13556–15283 |
| U34592 | hexon; N-terminal 14 codons of 23K (protease) gene | unpublished | 19036–21896 |
| U33016 | protease (23K) | McCoy et al., 1996b | 21897–22676 |
| U82628 | 100K | unpublished | 24056–26572 |
| U10433 | E3, pVIII, fiber | Reddy et al., 1995a | 27089–31148 |
| L43363 | E4 | Reddy et al., 1997 | 31064–34094 |

Knowledge of the PAV genome sequence is useful for both therapeutic and diagnostic procedures. Regions suitable for insertion and regulated expression of heterologous sequences have been identified. These regions include, but are not limited to the E1 region including E1A, E1B$^{small}$ and E1B$^{large}$, E3 and E4 regions, including E4 ORF 1-ORF7 regions, and the region between the E4 region and the right end of the genome. A heterologous nucleotide sequence, with respect to the PAV vectors of the invention, is one which is not normally associated with PAV sequences as part of the PAV genome. Heterologous nucleotide sequences include synthetic sequences. Regions encoding immunogenic PAV polypeptides, for use in immunodiagnostic procedures, have also been identified and are disclosed herein. These include the regions encoding the following PAV proteins: E1A, E1B$^{small}$ and E1B$^{large}$, E4, including ORF1-ORF7 regions, pIX, DBP, pTP, pol, IVa2, 52K, IIIA, pIII, pVII, pV, pX, pVI, 33K, pVIII, hexon and fiber (see Table 2). Regions essential for viral replication, such as E1 regions E1A and E1B$^{large}$, E2A, and E4 ORF3 can be deleted to provide attenuated strains for use as vaccines. Nonessential regions, such as E1B$^{small}$ and parts of the E3 and E4 regions, such as for example E4 ORF1-ORF2 and E4 ORF 4-ORF7 can be deleted to provide insertion sites, or to provide additional capacity for insertion at a site other than the deleted region. Deletions of viral sequences can be obtained by any method known in the art, including but not limited to restriction enzyme digestion and ligation, oligonucleotide-mediated deletion mutagenesis, and the like.

The practice of the present invention employs, unless otherwise indicated, conventional microbiology, immunology, virology, molecular biology, and recombinant DNA techniques which are within the skill of the art. These techniques are fully explained in the literature. See, e.g., Maniatis et al., *Molecular Cloning: A Laboratory Manual* (1982); *DNA Cloning: A Practical Approach*, vols. I & II (D. Glover, ed.); *Oligonucleotide Synthesis* (N. Gait, ed. (1984)); *Nucleic Acid Hybridization* (B. Hames & S. Higgins, eds. (1985)); *Transcription and Translation* (B. Hames & S. Higgins, eds. (1984)); *Animal Cell Culture* (R. Freshney, ed. (1986)); Perbal, *A Practical Guide to Molecular Cloning* (1984); Ausubel, et al., *Current Protocols In Molecular Biology*, John Wiley & Sons (1987, 1988, 1989, 1990, 1991, 1992, 1993, 1994, 1995, 1996); and Sambrook et al., *Molecular Cloning: A Laboratory Manual* ($2^{nd}$ Edition); vols. I, II & III (1989).

For general information related to mammalian adenovirus see "Fundamental Virology", second edition, 1991, ed. B. N.

Fields, Raven Press, New York, pages 771-813; and "Fields Virology", third edition, 1995, ed. B. N. Fields, vol. 2, pages 2111-2172.

Nucleotide Sequence, Genome Organization, and Transcription Map of Porcine Adenovirus Type 3 (PAV-3).

The complete nucleotide sequence of PAV-3 genome is 34,094 base pairs (bp) in length and has a base composition of 31.3% G, 32.5% C, 18.3% A, and 17.9% T. Thus, the sequence of the PAV-3 genome has a G+C content of 63.8%, which is unusually high when compared with the G+C content of many other animal adenoviruses. The genome termini share inverted terminal repeats (ITR) of 144 bp. Reddy et al., 1995c, supra. The organization of the genome as determined by analysis of open reading frames (ORFs), nuclease protection mapping, and sequencing of cDNA clones, is summarized in Table 2 and FIG. 2. The present invention relates to the characterization of the PAV E1 region. For PAV3, the E1A region is from nucleotide 533 to nucleotide 1222 of FIG. 1, the E1B$^{small}$ region is from nucleotide 1461 to nucleotide 2069 of FIG. 1 and the E1B$^{large}$ region is from nucleotide 1829 to nucleotide 3253 of FIG. 1. E1B$^{small}$ and E1B$^{large}$ nucleotide regions are overlapping and are differentially transcribed. Depending upon the intended use of the PAV vector, PAV constructs can be made comprising a deletion of part or all of the E1B$^{small}$ region. For example, if the entire E1B function is intended to be deleted, the entire E1B nucleotide region from nucleotides 1461 to 3253 can be deleted; or the region from nucleotides 1461 to 2069 can be deleted (which disrupts both E1B$^{small}$ and E1B$^{large}$ function); or the region from 1461 to 2069 and additionally, any portion of nucleotides 2069 through 3253 can be deleted. If it is intended to delete E1B$^{small}$ nucleotides while retaining E1B$^{large}$ function, nucleotides 1461 to 1829 are deleted, leaving the nucleotide region for E1B$^{large}$ intact.

The present invention also relates to the characterization of the E4 regions. As shown herein in the examples, E4 ORF3 is essential for replication. Table 5 in the examples provides nucleotide ranges for the E4 ORF regions.

Figure 2:
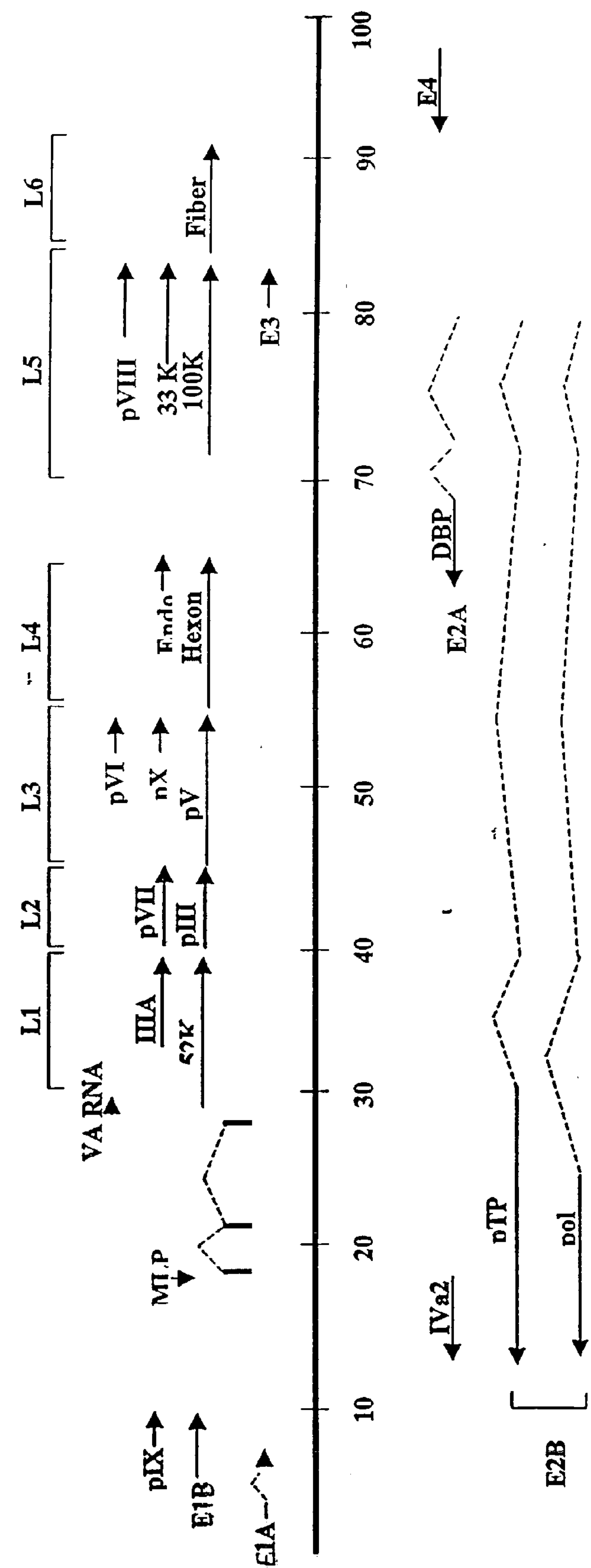

One important feature of PAV-3 genome is the presence of a short virion associated (VA) RNA gene between the splice acceptor sites of the precursor terminal protein (pTP) and 52 kDa protein genes (FIG. 2). Expression of VA genes increases the kinetics of viral replication; thereby providing the potential for higher yields of recombinant gene products using the PAV vectors of the invention. The locations of the signature sequences present upstream and downstream of VA RNA genes indicate the VA RNA gene of PAV-3 is about 126 nucleotides (nt) in length. This is somewhat shorter than most VA RNAs, whose lengths are 163±14 nts, however shorter VA RNAs have also been reported in HAV-10 and CELO virus. Ma et al. (1996) *J. Virol.* 70:5083-5099; and Chiocca et al. (1996) *J. Virol.* 70:2939-2949. The VA RNA genes were not found in the genomes of BAV-3, CAV-1, and OAV. Reddy et al. (1998) *J. Virol.* 72:1394-1402; Morrison et al. (1997) *J. Gen. Virol.* 78:873-878; and Vrati et al. (1996) *Virology* 220: 186-199.

In PAV-3 the major late transcript initiates at 17.7 map units (m.u.: an adenovirus map unit is 1% of genome length, starting from the left end of the genome). There are six 3'-coterminal families of late mRNAs, denoted L1 to L6 (see FIG. 2). All mRNAs produced from the major late promoter (MLP) contain a tripartite leader sequence (TPL). The first portion of the TPL lies next to the MLP and is 61 nts long. The second portion lies within the gene coding for pol and is 68 nt in length. The third portion is 99 nts long and is located within the gene coding for pTP. Thus the TPL of PAV-3 is 228 nt long and is derived from three exons located at 17.7, 20.9, and 28.1 m.u.

The MLP and TPL sequences can be used for expression of a heterologous sequence in a recombinant PAV vector or in any other adenoviral expression system.

TABLE 2

Transcriptional and Translational Features of the PAV-3 Genome

| Region | Gene | Transcription start site | ATG | Splice donor site | Splice acceptor site | Poly(A) signal | Poly(A) addition site |
|---|---|---|---|---|---|---|---|
| E1A | 229R | heterogeneous | 533 | | | 1286 | 1307 |
| | 214R | | 533 | 1043 | 1140 | 1286 | 1307 |
| E1B | 202R | 1382 | 1461 | | | 4085 | 4110, 4112 |
| | 474R | 1382 | 1829 | | | 4085 | 4110, 4112 |
| pIX | Pix | 3377 | 3394 | | | 4085 | 4110, 4112 |
| E2A | DBP | 17011c | 24041c | 26949c, 24714c | 24793c, 24051c | 22560c | 22536c |
| E2B | pTP | 17011c | 13638c | 24949c, 24714c | 24793c, 13772c | 4075c | 4053c |
| | pol | 17011c | 13638c | 24949c, 24714c | 24793†c, 13772†c | 4075c | 4053c |
| IVa2 | IVa2 | 5867c | 5711c | 5699c | 5441c | 4075c | 4053c |
| E3 | | 27473 | | | | 28765 | 28793 |
| E4 | | 33730c | | | | 31189c | 31170c |
| L1 | 52K | 6064 | 10629 | 9684 | 10606 | 13601 | 13627 |
| | IIIA | 6064 | 11719 | 9684 | 11715 | 13601 | 13627 |
| L2 | pIII | 6064 | 13662 | 9684 | 13662 | 15698* | 15735 |
| | pVII | 6064 | 15170 | 9684 | 15139 | 15698* | 15735 |
| L3 | pV | 6064 | 15819 | 9684 | 15793 | 18992 | 19013 |
| | pX | 6064 | 17783 | 9684 | 17776 | 18992 | 19013 |
| | pVI | 6064 | 18076 | 9684 | 18063 | 18992 | 19013 |
| L4 | Hexon | 6064 | 19097 | 9684 | 19096 | 22544 | 22567 |
| | Protease | 6064 | 21934 | 9684 | 21931† | 22544 | 22567 |
| L5 | 100k | 6064 | 24056 | 9684 | 24056 | 28765 | 28793 |
| | 33K | 6064 | 26181 | 9684 | 26130 | 28765 | 29793 |

TABLE 2-continued

Transcriptional and Translational Features of the PAV-3 Genome

| Region | Gene | Transcription start site | ATG | Splice donor site | Splice acceptor site | Poly(A) signal | Poly(A) addition site |
|---|---|---|---|---|---|---|---|
| | pVIII | 6064 | 27089 | 9684 | 26792 | 28765 | 28793 |
| L6 | Fiber | 6064 | 28939 | 9684 | 28910 | 31143 | 31164 |

Notes:
*TTGTTT is present as a polyadenylation signal instead of AATAAA
†The splice acceptor sites for the pol and protease genes were determined based on consensus splice acceptor sequences
"c"refers to sequences on the complementary (leftward-reading) strand of the PAV genome.

Construction of Recombinant PAV Vectors

In one embodiment of the invention, a recombinant PAV vector is constructed by in vivo recombination between a plasmid and a PAV genome. Generally, heterologous sequences are inserted into a plasmid vector containing a portion of the PAV genome, which may or may not possess one or more deletions of PAV sequences. The heterologous sequences are inserted into the PAV insert portion of the plasmid vector, such that the heterologous sequences are flanked by PAV sequences that are adjacent on the PAV genome. The PAV sequences serve as "guide sequences," to direct insertion of the heterologous sequences to a particular site in the PAV genome; the insertion site being defined by the genomic location of the guide sequences.

The vector is generally a bacterial plasmid, allowing multiple copies of the cloned sequence to be produced. In one embodiment, the plasmid is co-transfected, into an appropriate host cell, with a PAV genome comprising a full-length or nearly full-length PAV genomic sequence. The PAV genome can be isolated from PAV virions, or can comprise a PAV genome that has been inserted into a plasmid, using standard techniques of molecular biology and biotechnology. Construction of a plasmid containing a PAV genome is described in Example 2, infra. Nearly full-length PAV genomic sequences can be deleted in regions such as E1, E3, E4 and the region between E4 and the right end of the genome, but will retain sequences required for replication and packaging. PAV genomes can be deleted in essential regions, such as E1A and/or E1B$^{large}$ and/or E4 ORF3 if the essential function are supplied by a helper cell line.

Insertion of the cloned heterologous sequences into a viral genome occurs by in vivo recombination between a plasmid vector (containing heterologous sequences flanked by PAV guide sequences) and a PAV genome following co-transfection into a suitable host cell. The PAV genome contains inverted terminal repeat (ITR) sequences required for initiation of viral DNA replication (Reddy et al. (1995c), supra), and sequences involved in packaging of replicated viral genomes. Adenovirus packaging signals generally lie between the left ITR and the E1A promoter. Incorporation of the cloned heterologous sequences into the PAV genome thus places the heterologous sequences into a DNA molecule containing viral replication and packaging signals, allowing generation of multiple copies of a recombinant PAV genome that can be packaged into infectious viral particles. Alternatively, incorporation of the cloned heterologous sequences into a PAV genome places these sequences into a DNA molecule that can be replicated and packaged in an appropriate helper cell line. Multiple copies of a single sequence can be inserted to improve yield of the heterologous gene product, or multiple heterologous sequences can be inserted so that the recombinant virus is capable of expressing more than one heterologous gene product. The heterologous sequences can contain additions, deletions and/or substitutions to enhance the expression and/or immunological effect of the expressed gene product(s).

Attachment of guide sequences to a heterologous sequence can also be accomplished by ligation in vitro. In this case, a nucleic acid comprising a heterologous sequence flanked by PAV guide sequences can be co-introduced into a host cell along with a PAV genome, and recombination can occur to generate a recombinant PAV vector. Introduction of nucleic acids into cells can be achieved by any method known in the art, including, but not limited to, microinjection, transfection, electroporation, $CaPO_4$ precipitation, DEAE-dextran, liposomes, particle bombardment, etc.

In one embodiment of the invention, a recombinant PAV expression cassette can be obtained by cleaving a wild-type PAV genome with an appropriate restriction enzyme to produce a PAV restriction fragment representing, for example, the left end or the right end of the genome comprising E1 or E3 gene region sequences, respectively. The PAV restriction fragment can be inserted into a cloning vehicle, such as a plasmid, and thereafter at least one heterologous sequence (which may or may not encode a foreign protein) can be inserted into the E1 or E3 region with or without an operatively-linked eukaryotic transcriptional regulatory sequence. The recombinant expression cassette is contacted with a PAV genome and, through homologous recombination or other conventional genetic engineering methods, the desired recombinant is obtained. In the case wherein the expression cassette comprises the E1 essential regions, such as, E1A and/or E1B$^{large}$ or some other essential region, such as E4 ORF3, recombination between the expression cassette and a PAV genome can occur within an appropriate helper cell line such as, for example, an E1A transformed cell line when E1A region is deleted or E1A function is inactivated, an E1B$^{large}$ transformed cell line when E1B$^{large}$ is deleted or E1B$^{large}$ function is inactivated or an E4 ORF 3 cell line when E4 ORF3 is deleted or E4 ORF3 function is inactivated. Restriction fragments of the PAV genome other than those comprising the E1 or E3 regions are also useful in the practice of the invention and can be inserted into a cloning vehicle such that heterologous sequences can be inserted into the PAV sequences. These DNA constructs can then undergo recombination in vitro or in vivo, with a PAV genome either before or after transformation or transfection of an appropriate host cell.

The invention also includes an expression system comprising a porcine adenovirus expression vector wherein a heterologous nucleotide sequence, e.g. DNA, replaces part or all of the E3 region, part or all of the E1 region, part or all of the E2 region, part or all of the E4 region, part or all of the late region and/or part or all of the regions occupied by the pIX, DBP, pTP, pol, IVa2, 52K, IIIA, pIII, pVII, pV, pX, pVI, and 33K genes. The expression system can be used wherein the foreign nucleotide sequences, e.g. DNA, are optionally in operative linkage with a eukaryotic transcriptional regulatory sequence. PAV expression vectors can also comprise inverted terminal repeat (ITR) sequences and packaging sequences.

The PAV E1A, E1B$^{large}$, E4 ORF3, pIX, DBP, pTP, pol, IVa2, 52K, IIIA, pIII, pVII, pV, pX, pVI, and 33K genes are essential for viral replication. Therefore, PAV vectors comprising deletions in any of these genes, or which lack functions encoded by any of these genes, are grown in an appropriate complementing cell line (i.e., a helper cell line). E1B$^{small}$ and most, if not all, of the open reading frames in the E3 and E4 regions, e.g. ORF1, ORF2 and ORF4-ORF7 of PAV-3 are non-essential for viral replication and, therefore, deletions in these regions can be constructed for insertion or to increase vector capacity, without necessitating the use of a helper cell line for growth of the viral vector.

In another embodiment, the invention provides a method for constructing a full-length clone of a PAV genome by homologous recombination in vivo. In this embodiment, two or more plasmid clones, containing overlapping segments of the PAV genome and together covering the entire genome, are introduced into an appropriate bacterial host cell. Approximately 30 base pairs of overlap is required for homologous recombination in *E. coli*. Chartier et al. (1996) *J. Virol.* 70:4805-4810. Through in vivo homologous recombination, the PAV genome segments are joined to form a full-length PAV genome. In a further embodiment, a recombinant plasmid containing left-end sequences and right-end sequences of the PAV genome, separated by a unique restriction site, is constructed. This plasmid is digested with the restriction enzyme recognizing the unique restriction site, to generate a unit-length linear plasmid, which is introduced into a cell together with a full-length PAV genome. Homologous recombination within the cell will result in production of a recombinant plasmid containing a full-length PAV genome. Recombinant plasmids will also generally contain sequences specifying replication in a host cell and one or more selective markers, such as, for example, antibiotic resistance.

Suitable host cells include any cell that will support recombination between a PAV genome and a plasmid containing PAV sequences, or between two or more plasmids, each containing PAV sequences. Recombination is generally performed in procaryotic cells, such as *E. coli*, while transfection of a plasmid containing a viral genome, to generate virus particles, is conducted in eukaryotic cells, preferably mammalian cells, most preferably porcine cell cultures. The growth of bacterial cell cultures, as well as culture and maintenance of eukaryotic cells and mammalian cell lines are procedures which are well-known to those of skill in the art.

In one embodiment of the invention, a replication-defective recombinant PAV vector is used for expression of heterologous sequences. In some embodiments, the replication-defective vector lacks E1A and/or E1B$^{large}$ and/or E4 ORF3 region function. In some embodiments, the replication-defective PAV vector comprises a deletion of the E1A region or an inactivation of the E1A gene function, such as through an insertion in the E1A gene region. Construction of a deletion in the E1 region of PAV is described in Example 3 and Example 10, infra. Heterologous sequences can be inserted so as to replace the deleted E1A or E1B region(s), and/or can be inserted at other sites in the PAV genome, preferably E3, E4 and/or the region between E4 and the right end of the genome. Replication-defective vectors with deletions in essential E1 regions, such as, E1A and E1B$^{large}$ are grown in helper cell lines expressing E1A and E1B$^{large}$, which provide the deleted E1 function. Replication-defective vectors with deletions in E4 ORF3 are grown in helper cell lines expressing E4 ORF3.

Accordingly, in one embodiment of the invention, a number of recombinant helper cell lines are produced according to the present invention by constructing an expression cassette comprising an adenoviral essential E1 region, such as E1A and/or E1B$^{large}$ and/or E4 ORF3 and transforming host cells therewith to provide complementing cell lines or cultures providing deleted functions. In some embodiments, the host cell is transformed with a human or porcine E1A gene region. In other embodiments, the host cell is transformed with human or porcine E1B gene region. In other embodiments, the host cell is transformed with human or porcine E4 ORF3 gene region. The terms "complementing cell," "complementing cell line," "helper cell" and "helper cell line" are used interchangeably herein to denote a cell line that provides a viral function that is deficient in a deleted PAV, including an essential E1 function or essential E4 function. These recombinant complementing cell lines are capable of allowing a replication-defective recombinant PAV, having a deleted E1 gene region that is essential for replication, such as E1A and E1B$^{large}$, wherein the deleted sequences are optionally replaced by heterologous nucleotide sequences, to replicate and express one or more foreign genes or fragments thereof encoded by the heterologous nucleotide sequences. PAV vectors with E1 deletions, wherein heterologous sequences are inserted in regions other than E1, can also be propagated in these complementing cell lines, and will express the heterologous sequences if they are inserted downstream of a PAV promoter or are inserted in operative linkage with a eukaryotic regulatory sequence. Helper cell lines include VIDO R1 cells, as described in Example 1, infra. Briefly, the VIDO R1 cell line is a porcine fetal retinal cell line that has been transfected with DNA from the human adenovirus type 5 (HAV-5) E1 region, and which supports the growth of PAV E1A deletions and HAV-5 E1 deletions. Recombinant complementing cell lines expressing E4 ORF3 are capable of allowing a replication-defective recombinant PAV, having a deleted E4 ORF3 gene region that is essential for replication and optionally replaced by heterologous nucleotide sequences, to replicate and express one or more foreign genes or fragments thereof encoded by the heterologous nucleotide sequences.

In the present invention, a PAV E1-complementing cell line employing the E1 region of HAV-5 is shown to complement PAV-3 E1 mutants. There are several reasons that the E1 region of HAV-5 was used for transformation of porcine embryonic retinal cells. The E1 region of HAV-5 was shown to transform human retina cells very efficiently. Fallaux et al. (1998) supra. The E1 region of HAV-5 has been thoroughly characterized and the monoclonal antibodies against the E1 proteins are readily available from commercial sources. In addition, the E1 A region of HAV-5 was shown to complement the E1A functions of several non-human adenoviruses. Ball et al. (1988) *J. Virol.* 62:3947-3957; Zheng et al. (1994) *Virus Res.* 31:163-186. As shown herein in Example 11, a helper cell line expressing human adenovirus E1 and porcine E1 B$^{large}$ was able to rescue a porcine adenovirus having a deletion of the entire E1 region, including E1B$^{large}$ nucleic acid.

More generally, replication-defective recombinant PAV vectors, lacking one or more essential functions encoded by the PAV genome, can be propagated in appropriate complementing cell lines, wherein a particular complementing cell line provides a function or functions that is (are) lacking in a particular defective recombinant PAV vector. Complementing cell lines can provide viral functions through, for example, co-infection with a helper virus, or by integrating or otherwise maintaining in stable form a fragment of a viral genome encoding a particular viral function.

In another embodiment of the invention, E1 function (or the function of any other viral region which may be mutated or deleted in any particular viral vector) can be supplied (to provide a complementing cell line) by co-infection of cells with a virus which expresses the function that the vector lacks.

PAV Expression Systems

In one embodiment, the present invention identifies and provides means of deleting regions of the PAV genome, to provide sites into which heterologous or homologous nucleotide sequences encoding foreign genes or fragments thereof can be inserted to generate porcine adenovirus recombinants. In preferred embodiments, deletions are made in part or all of the nucleotide sequences of the PAV E1, E3, or E4 regions and/or the region between E4 and the right end of genome. E1 gene region deletions are described in Example 3 and Example 10. E3 deletion and insertion of heterologous sequence in the E3 region are described in Example 4 and 5; and insertion of a heterologous sequence between the E4 region and the right end of the PAV genome, as well as expression of the inserted sequence, is described in Example 6, infra. E4 region deletions are shown in Example 14.

In another embodiment, the invention identifies and provides additional regions of the PAV genome (and fragments thereof) suitable for insertion of heterologous or homologous nucleotide sequences encoding foreign genes or fragments thereof to generate PAV recombinants. These regions include nucleotides 145-13,555; 15,284-19,035; 22,677-24,055; 26,573-27,088; and 31,149-34,094 and comprise the E2 region, the late region, and genes encoding the pIX, DBP, pTP, pol, IVa2, 52K, IIIA, pIII, pVII, pV, pX, pVI, and 33K proteins. These regions of the PAV genome can be used, among other things, for insertion of foreign sequences, for provision of DNA control sequences including transcriptional and translational regulatory sequences, or for diagnostic purposes to detect the presence, in a biological sample, of viral nucleic acids and/or proteins encoded by these regions. Example 7, infra, describes procedures for constructing insertions in these regions.

One or more heterologous sequences can be inserted into one or more regions of the PAV genome to generate a recombinant PAV vector, limited only by the insertion capacity of the PAV genome and ability of the recombinant PAV vector to express the inserted heterologous sequences. In general, adenovirus genomes can accept inserts of approximately 5% of genome length and remain capable of being packaged into virus particles. The insertion capacity can be increased by deletion of non-essential regions and/or deletion of essential regions whose function is provided by a helper cell line. In some examples, E4ORF1-ORF2 and ORF4-ORF7 non essential regions and E1B$^{small}$ are deleted to provide additional insertion capacity.

In one embodiment of the invention, insertion can be achieved by constructing a plasmid containing the region of the PAV genome into which insertion is desired. The plasmid is then digested with a restriction enzyme having a recognition sequence in the PAV portion of the plasmid, and a heterologous sequence is inserted at the site of restriction digestion. The plasmid, containing a portion of the PAV genome with an inserted heterologous sequence, in co-transformed, along with a plasmid (such as pPAV-200) containing a full-length PAV genome, into a bacterial cell (such as, for example, *E. coli*), wherein homologous recombination between the plasmids generates a full-length PAV genome containing inserted heterologous sequences.

Deletion of PAV sequences, to provide a site for insertion of heterologous sequences or to provide additional capacity for insertion at a different site, can be accomplished by methods well-known to those of skill in the art. For example, for PAV sequences cloned in a plasmid, digestion with one or more restriction enzymes (with at least one recognition sequence in the PAV insert) followed by ligation will, in some cases, result in deletion of sequences between the restriction enzyme recognition sites. Alternatively, digestion at a single restriction enzyme recognition site within the PAV insert, followed by exonuclease treatment, followed by ligation will result in deletion of PAV sequences adjacent to the restriction site. A plasmid containing one or more portions of the PAV genome with one or more deletions, constructed as described above, can be co-transfected into a bacterial cell along with a plasmid containing a full-length PAV genome to generate, by homologous recombination, a plasmid containing a PAV genome with a deletion at a specific site. PAV virions containing the deletion can then be obtained by transfection of mammalian cells (such as ST or VIDO R1 cells) with the plasmid containing a PAV genome with a deletion at a specific site.

Expression of an inserted sequence in a recombinant PAV vector will depend on the insertion site. Accordingly, preferred insertion sites are adjacent to and downstream (in the transcriptional sense) of PAV promoters. The transcriptional map of PAV, as disclosed herein, provides the locations of PAV promoters. Locations of restriction enzyme recognition sequences downstream of PAV promoters, for use as insertion sites, can be easily determined by one of skill in the art from the PAV nucleotide sequence provided herein. Alternatively, various in vitro techniques can be used for insertion of a restriction enzyme recognition sequence at a particular site, or for insertion of heterologous sequences at a site that does not contain a restriction enzyme recognition sequence. Such methods include, but are not limited to, oligonucleotide-mediated heteroduplex formation for insertion of one or more restriction enzyme recognition sequences (see, for example, Zoller et al. (1982) *Nucleic Acids Res.* 10:6487-6500; Brennan et al. (1990) *Roux's Arch. Dev. Biol.* 199:89-96; and Kunkel et al. (1987) *Meth. Enzymology* 154:367-382) and PCR-mediated methods for insertion of longer sequences. See, for example, Zheng et al. (1994) *Virus Research* 31:163-186.

It is also possible to obtain expression of a heterologous sequence inserted at a site that is not downstream from a PAV promoter, if the heterologous sequence additionally comprises transcriptional regulatory sequences that are active in eukaryotic cells. Such transcriptional regulatory sequences can include cellular promoters such as, for example, the bovine hsp70 promoter and viral promoters such as, for example, herpesvirus, adenovirus and papovavirus promoters and DNA copies of retroviral long terminal repeat (LTR) sequences.

In another embodiment, homologous recombination in a procaryotic cell can be used to generate a cloned PAV genome; and the cloned PAV-3 genome can be propagated as a plasmid. Infectious virus can be obtained by transfection of mammalian cells with the cloned PAV genome rescued from plasmid-containing cells. Example 2, infra describes construction of an infectious plasmid containing a PAV-3 genome.

The invention provides PAV regulatory sequences which can be used to regulate the expression of heterologous genes. A regulatory sequence can be, for example, a transcriptional regulatory sequence, a promoter, an enhancer, an upstream regulatory domain, a splicing signal, a polyadenylation signal, a transcriptional termination sequence, a translational regulatory sequence, a ribosome binding site and a translational termination sequence.

Therapeutic Genes and Polypeptides

The PAV vectors of the invention can be used for the expression of, production of, therapeutic polypeptides in applications such as in vitro polypeptide production, vaccine production, nucleic acid immunization and gene delivery, for example. The PAV vectors of the present invention can be used to produce polypeptides, of therapeutic or diagnostic value. Therapeutic polypeptides comprise any polypeptide sequence with therapeutic and/or diagnostic value and include, but are not limited to, coagulation factors, growth hormones, cytokines, lymphokines, tumor-suppressing polypeptides, cell receptors, ligands for cell receptors, protease inhibitors, antibodies, toxins, immunotoxins, dystrophins, cystic fibrosis transmembrane conductance regulator (CFTR) and immunogenic polypeptides.

In some examples, PAV vectors will comprise heterologous sequences encoding protective determinants of various pathogens of mammals such as for example, humans or swine, for use in subunit vaccines and nucleic acid immunization. Representative swine pathogen antigens include, but are not limited to, pseudorabies virus (PRV) gp50; transmissible gastroenteritis virus (TGEV) S gene; porcine rotavirus VP7 and VP8 genes; genes of porcine respiratory and reproductive syndrome virus (PRRS), in particular ORFs 3, 4 and 5; genes of porcine epidemic diarrhea virus; genes of hog cholera virus, genes of porcine parvovirus, and genes of porcine influenza virus. Representative human pathogens include, but are not limited to, HIV virus and Hepatitis virus.

Various foreign genes or nucleotide sequences or coding sequences (prokaryotic, and eukaryotic) can be inserted into a PAV vector, in accordance with the present invention, particularly to provide protection against a wide range of diseases for use in mammals including humans and swine. Many such genes are already known in the art; the problem heretofore having been to provide a safe, convenient and effective vaccine vector for the genes or sequences.

A heterologous (i.e., foreign) nucleotide sequence can consist of one or more gene(s) of interest, and preferably of therapeutic interest. In the context of the present invention, a gene of interest can code either for an antisense RNA, a ribozyme or for an mRNA which will then be translated into a protein of interest. A gene of interest can be of genomic type, of complementary DNA (cDNA) type or of mixed type (minigene, in which at least one intron is deleted). It can code for a mature protein, a precursor of a mature protein, in particular a precursor intended to be secreted and accordingly comprising a signal peptide, a chimeric protein originating from the fusion of sequences of diverse origins, or a mutant of a natural protein displaying improved or modified biological properties. Such a mutant can be obtained by deletion, substitution and/or addition of one or more nucleotide(s) of the gene coding for the natural protein, or any other type of change in the sequence encoding the natural protein, such as, for example, transposition or inversion.

A gene of interest can be placed under the control of regulatory sequences suitable for its expression in a host cell. Suitable regulatory sequences are understood to mean the set of elements needed for transcription of a gene into RNA (ribozyme, antisense RNA or mRNA), for processing of RNA, and for the translation of an mRNA into protein. Among the elements needed for transcription, the promoter assumes special importance. It can be a constitutive promoter or a regulatable promoter, and can be isolated from any gene of eukaryotic, prokaryotic or viral origin, and even adenoviral origin. Alternatively, it can be the natural promoter of the gene of interest. Generally speaking, a promoter used in the present invention can be chosen to contain cell-specific regulatory sequences, or modified to contain such sequences. For example, a gene of interest for use in the present invention is placed under the control of an immunoglobulin gene promoter when it is desired to target its expression to lymphocytic host cells. There may also be mentioned the HSV-1 TK (herpesvirus type 1 thymidine kinase) gene promoter, the adenoviral MLP (major late promoter), in particular of human adenovirus type 2, the RSV (Rous Sarcoma Virus) LTR (long terminal repeat), the CMV (Cytomegalovirus) early promoter, and the PGK (phosphoglycerate kinase) gene promoter, for example, permitting expression in a large number of cell types.

Alternatively, targeting of a recombinant PAV vector to a particular cell type can be achieved by constructing recombinant hexon and/or fiber genes. The protein products of these genes are involved in host cell recognition; therefore, the genes can be modified to contain peptide sequences that will allow the virus to recognize alternative host cells.

Among genes of interest which are useful in the context of the present invention, there may be mentioned:

- genes coding for cytokines such as interferons and interleukins;
- genes encoding lymphokines;
- genes coding for membrane receptors such as the receptors recognized by pathogenic organisms (viruses, bacteria or parasites), preferably by the HIV virus (human immunodeficiency virus);
- genes coding for coagulation factors such as factor VIII and factor IX;
- genes coding for dystrophins;
- genes coding for insulin;
- genes coding for proteins participating directly or indirectly in cellular ion channels, such as the CFTR (cystic fibrosis transmembrane conductance regulator) protein;
- genes coding for antisense RNAs, or proteins capable of inhibiting the activity of a protein produced by a pathogenic gene which is present in the genome of a pathogenic organism, or proteins (or genes encoding them) capable of inhibiting the activity of a cellular gene whose expression is deregulated, for example an oncogene;
- genes coding for a protein inhibiting an enzyme activity, such as $\alpha_1$-antitrypsin or a viral protease inhibitor, for example;
- genes coding for variants of pathogenic proteins which have been mutated so as to impair their biological function, such as, for example, trans-dominant variants of the tat protein of the HIV virus which are capable of competing with the natural protein for binding to the target sequence, thereby preventing the activation of HIV;
- genes coding for antigenic epitopes in order to increase the host cell's immunity;
- genes coding for major histocompatibility complex classes I and II proteins, as well as the genes coding for the proteins which are inducers of these genes;
- genes coding for antibodies;
- genes coding for immunotoxins;
- genes encoding toxins;
- genes encoding growth factors or growth hormones;
- genes encoding cell receptors and their ligands;
- genes encoding tumor suppressors;
- genes coding for cellular enzymes or those produced by pathogenic organisms; and suicide genes. The HSV-1 TK suicide gene may be mentioned as an example. This viral TK enzyme displays markedly greater affinity compared to the cellular TK enzyme for certain nucleoside analogues (such as acyclovir or gancyclovir). It converts them to monophosphorylated molecules, which can themselves be converted by cellular enzymes to nucleotide precursors, which are toxic. These nucleotide analogues can-be incorporated into replicating DNA molecules, hence incorporation occurs chiefly in the DNA of dividing cells. This incorporation can result in specific destruction of dividing cells such as cancer cells.

This list is not restrictive, and any other gene of interest can be used in the context of the present invention. In some cases the gene for a particular antigen can contain a large number of introns or can be from an RNA virus, in these cases a complementary DNA copy (cDNA) can be used. It is also possible that only fragments of nucleotide sequences of genes can be used (where these are sufficient to generate a protective immune response or a specific biological effect) rather than the complete sequence as found in the wild-type organism. Where available, synthetic genes or fragments thereof can also be used. However, the present invention can be used with a wide variety of genes, fragments and the like, and is not limited to those set out above.

Recombinant PAV vectors can be used to express antigens for provision of, for example, subunit vaccines for use in mammals including humans and swine. Antigens used in the present invention can be either native or recombinant antigenic polypeptides or fragments. They can be partial sequences, full-length sequences, or even fusions (e.g., having appropriate leader sequences for the recombinant host, or with an additional antigen sequence for another pathogen). The preferred antigenic polypeptide to be expressed by the virus systems of the present invention contain full-length (or near full-length) sequences encoding antigens. Alternatively, shorter sequences that are antigenic (i.e., encode one or more epitopes) can be used. The shorter sequence can encode a "neutralizing epitope," which is defined as an epitope capable of eliciting antibodies that neutralize virus infectivity in an in vitro assay. Preferably the peptide should encode a "protective epitope" that is capable of raising in the host a "protective immune response;" i.e., a humoral (i.e. antibody-mediated), cell-mediated, and/or mucosal immune response that protects an immunized host from infection.

The antigens used in the present invention, particularly when comprised of short oligopeptides, can be conjugated to a vaccine carrier. Vaccine carriers are well known in the art: for example, bovine serum albumin (BSA), human serum albumin (HSA) and keyhole limpet hemocyanin (KLH). A preferred carrier protein, rotavirus VP6, is disclosed in EPO Pub. No. 0259149, the disclosure of which is incorporated by reference herein.

Genes for desired antigens or coding sequences thereof which can be inserted include those of organisms which cause disease in mammals, particularly porcine pathogens such as pseudorabies virus (PRV), transmissible gastroenteritis virus (TGEV), porcine rotavirus, porcine respiratory and reproductive syndrome virus (PRRS), porcine epidemic diarrhea virus (PEDV), hog cholera virus (HCV), porcine parvovirus and the like. Genes encoding antigens of human pathogens, such as HIV and Hepatitis are also useful in the practice of the invention.

Therapeutic Applications

With the recombinant viruses of the present invention, it is possible to elicit an immune response against disease antigens and/or provide protection against a wide variety of diseases affecting swine, cattle, humans and other mammals. Any of the recombinant antigenic determinants or recombinant live viruses of the invention can be formulated and used in substantially the same manner as described for the antigenic determinant vaccines or live vaccine vectors.

The present invention also includes pharmaceutical compositions comprising a therapeutically effective amount of a recombinant vector, recombinant virus or recombinant protein, prepared according to the methods of the invention, in combination with a pharmaceutically acceptable vehicle and/or an adjuvant. Such a pharmaceutical composition can be prepared and dosages determined according to techniques that are well-known in the art. The pharmaceutical compositions of the invention can be administered by any known administration route including, but not limited to, systemically (for example, intravenously, intratracheally, intraperitoneally, intranasally, parenterally, enterically, intramuscularly, subcutaneously, intratumorally or intracranially) or by aerosolization or intrapulmonary instillation. Administration can take place in a single dose or in doses repeated one or more times after certain time intervals. The appropriate administration route and dosage will vary in accordance with the situation (for example, the individual being treated, the disorder to be treated or the gene or polypeptide of interest), but can be determined by one of skill in the art.

The vaccines of the invention carrying foreign genes or fragments can be orally administered in a suitable oral carrier, such as in an enteric-coated dosage form. Oral formulations include such normally-employed excipients as, for example, pharmaceutical grades of mannitol, lactose, starch, magnesium stearate, sodium saccharin cellulose, magnesium carbonate, and the like. Oral vaccine compositions may be taken in the form of solutions, suspensions, tablets, pills, capsules, sustained release formulations, or powders, containing from about 10% to about 95% of the active ingredient, preferably about 25% to about 70%. An oral vaccine may be preferable to raise mucosal immunity (which plays an important role in protection against pathogens infecting the gastrointestinal tract) in combination with systemic immunity.

In addition, the vaccine can be formulated into a suppository. For suppositories, the vaccine composition will include traditional binders and carriers, such as polyalkaline glycols or triglycerides. Such suppositories may be formed from mixtures containing the active ingredient in the range of about 0.5% to about 10% (w/w), preferably about 1% to about 2%.

Protocols for administering to animals the vaccine composition(s) of the present invention are within the skill of the art in view of the present disclosure. Those skilled in the art will select a concentration of the vaccine composition in a dose effective to elicit antibody, cell-mediated and/or mucosal immune responses to the antigenic fragment. Within wide limits, the dosage is not believed to be critical. Typically, the vaccine composition is administered in a manner which will deliver between about 1 to about 1,000 micrograms of the subunit antigen in a convenient volume of vehicle, e.g., about 1-10 ml. Preferably, the dosage in a single immunization will deliver from about 1 to about 500 micrograms of subunit antigen, more preferably about 5-10 to about 100-200 micrograms (e.g., 5-200 micrograms).

The timing of administration may also be important. For example, a primary inoculation preferably may be followed by subsequent booster inoculations, for example, several weeks to several months after the initial immunization, if needed. To insure sustained high levels of protection against disease, it may be helpful to re-administer booster immunizations at regular intervals, for example once every several years. Alternatively, an initial dose may be administered orally followed by later inoculations, or vice versa. Preferred vaccination protocols can be established through routine vaccination protocol experiments.

The dosage for all routes of administration of in vivo recombinant virus vaccine depends on various factors including, the size of patient, nature of infection against which protection is needed, carrier and the like and can readily be determined by those of skill in the art. By way of non-limiting example, a dosage of between approximately $10^3$ pfu and $10^8$ pfu can be used. As with in vitro subunit vaccines, additional dosages can be given as determined by the clinical factors involved.

A problem that has beset the use of adenovirus vectors for immunization and gene delivery in humans is the rapid development of an immunological response (or indeed in some cases existing immunity) to human adenoviruses (HAVs). Recombinant PAV vectors are likely to be less immunogenic in humans and, for this and other reasons, will be useful either as a substitute for HAV vectors or in combination with HAV vectors. For example, an initial immunization with a HAV vector can be followed by booster immunizations using PAV vectors; alternatively, initial immunization with a recombinant PAV vector can be followed by booster immunizations with HAV and/or PAV vectors. As shown herein in Examples 14 and 15, PAV can infect a variety of human cell lines.

The presence of low levels of helper-independent vectors in the batches of helper-dependent human adenoviruses that are grown in complementing human cell lines has been reported. Fallaux et al. (1998) supra. This occurs as a result of recombination events between the viral DNA and the integrated adenoviral sequences present in the complementing cell line. Hehir et al. (1996) *J. Virol* 70:8459-8467. This type of contamination constitutes a safety risk, which could result in the replication and spread of the virus. Complete elimination of helper-dependent adenoviruses in the batches of helper-dependent vectors can be achieved using two approaches. The first is by developing new helper cell lines and matched vectors that do not share any common sequences. Fallaux et al. (1998) supra. The second approach is to take advantage of possible cross-complementation between two distantly related adenoviruses such as HAV-5 and PAV-3. VIDO R1 cells contain the E1 coding sequences of HAV-5. Although there is no significant homology between the E1 regions of HAV-5 and PAV-3 at the nucleotide sequence level, the proteins produced from the region can complement each others' function(s). Thus, the problem of helper-independent vector generation by homologous recombination is eliminated when VIDO R1 cells are used for the propagation of recombinant PAV-3.

The invention also encompasses a method of treatment, according to which a therapeutically effective amount of a PAV vector, recombinant PAV, or host cell of the invention is administered to a mammalian subject requiring treatment. The finding that PAV-3 was effective in entering canine, sheep and bovine cells in which it does not replicate or replicates poorly is an important observation. See Example 8, infra. This may have implications in designing PAV-3 vectors for vaccination in these and other animal species. As shown herein, PAV is able to replicate in a number of mammalian cell lines.

Recombinant PAV vectors can be used for regulated expression of foreign polypeptides encoded by heterologous nucleotide sequences. Standard conditions of cell culture, such as are known to those of skill in the art, will allow maximal expression of recombinant polypeptides. They can be used, in addition, for regulated expression of RNAs encoded by heterologous nucleotide sequences, as in, for example, antisense applications and expression of ribozymes.

When the heterologous sequences encode an antigenic polypeptide, PAV vectors comprising insertions of heterologous nucleotide sequences can be used to provide large quantities of antigen which are useful, in turn, for the preparation of antibodies. Methods for preparation of antibodies are well-known to those of skill in the art. Briefly, an animal (such as a rabbit) is given an initial subcutaneous injection of antigen plus Freund's complete adjuvant. One to two subsequent injections of antigen plus Freund's incomplete adjuvant are given at approximately 3 week intervals. Approximately 10 days after the final injection, serum is collected and tested for the presence of specific antibody by ELISA, Western Blot, immunoprecipitation, or any other immunological assay known to one of skill in the art.

Adenovirus E1 gene products transactivate many cellular genes; therefore, cell lines which constitutively express E1 proteins can express cellular polypeptides at a higher levels than other cell lines. The recombinant mammalian, particularly porcine, cell lines of the invention can be used to prepare and isolate polypeptides, including those such as (a) proteins associated with adenovirus E1A proteins: e.g. p300, retinoblastoma (Rb) protein, cyclins, kinases and the like; (b) proteins associated with adenovirus E1B protein: e.g. p53 and the like; growth factors, such as epidermal growth factor (EGF), transforming growth factor (TGF) and the like; (d) receptors such as epidermal growth factor receptor (EGF-R), fibroblast growth factor receptor (FGF-R), tumor necrosis factor receptor (TNF-R), insulin-like growth factor receptor (IGF-R), major histocompatibility complex class I receptor and the like; (e) proteins encoded by proto-oncogenes such as protein kinases (tyrosine-specific protein kinases and protein kinases specific for serine or threonine), p21 proteins (guanine nucleotide-binding proteins with GTPase activity) and the like; (f) other cellular proteins such as actins, collagens, fibronectins, integrins, phosphoproteins, proteoglycans, histones and the like, and (g) proteins involved in regulation of transcription such as TATA-box-binding protein (TBP), TBP-associated factors (TAFs), Sp1 binding protein and the like.

Gene Delivery

The invention also includes a method for delivering a gene to a mammal, such as a porcine, human or other mammal in need thereof, to control a gene deficiency. In one embodiment, the method comprises administering to said mammal a live recombinant porcine adenovirus containing a heterologous nucleotide sequence encoding a non-defective form of said gene under conditions wherein the recombinant virus vector genome is incorporated into said mammalian genome or is maintained independently and extrachromosomally to provide expression of the required gene in the target organ or tissue. These kinds of techniques are currently being used by those of skill in the art to replace a defective gene or portion thereof. Examples of foreign genes, heterologous nucleotide sequences, or portions thereof that can be incorporated for use in gene therapy include, but are not limited to, cystic fibrosis transmembrane conductance regulator gene, human minidystrophin gene, alpha-1-antitrypsin gene and the like.

In particular, the practice-of the present invention in regard to gene delivery in humans is intended for the prevention or treatment of diseases including, but not limited to, genetic diseases (for example, hemophilia, thalassemias, emphysema, Gaucher's disease, cystic fibrosis, Duchenne muscular dystrophy, Duchenne's or Becker's myopathy, etc.), cancers, viral diseases (for example, AIDS, herpesvirus infection, cytomegalovirus infection and papillomavirus infection) and the like. For the purposes of the present invention, the vectors, cells and viral particles prepared by the methods of the invention may be introduced into a subject either ex vivo, (i.e., in a cell or cells removed from the patient) or directly in vivo into the body to be treated. Preferably, the host cell is a human cell and, more preferably, is a lung, fibroblast, muscle, liver or lymphocytic cell or a cell of the hematopoietic lineage.

Diagnostic Applications

The PAV genome, or any subregion of the PAV genome, is suitable for use as a nucleic acid probe, to test for the presence of PAV nucleic acid in a subject or a biological sample. The presence of viral nucleic acids can be detected by techniques known to one of skill in the art including, but not limited to, hybridization assays, polymerase chain reaction, and other types of amplification reactions. Suitable labels and hybridization techniques are well-known to those of skill in the art. See, for example, Kessler (ed.), *Nonradioactive Labeling and Detection of Biomolecules*, Springer-Verlag, Berlin, 1992; Kricka (ed.) *Nonisotopic DNA Probe Techniques*, Academic Press, San Diego, 1992; Howard (ed.) *Methods in Nonradioactive Detection*, Appleton & Lange, Norwalk, 1993; Ausubel et al., supra; and Sambrook et al., supra. Diagnostic kits comprising the nucleotide sequences of the invention can also contain reagents for cell disruption and nucleic acid purification, as well as buffers and solvents for the formation, selection and detection of hybrids.

Regions of the PAV genome can be inserted into any expression vector known in the art and expressed to provide, for example, vaccine formulations, protein for immunization, etc. The amino acid sequence of any PAV protein can be determined by one of skill in the art from the nucleotide sequences disclosed herein. PAV proteins can be used for diagnostic purposes, for example, to detect the presence of PAV antigens. Methods for detection of proteins are well-known to those of skill in the art and include, but are not limited to, various types of direct and competitive immunoassays, ELISA, Western blotting, enzymatic assay, immunohistochemistry, etc. See, for example, Harlow & Lane (eds.): Antibodies, A Laboratory Manual, Cold Spring Harbor Press, New York, 1988. Diagnostic kits comprising PAV polypeptides or amino acid sequences can also comprise reagents for protein isolation and for the formation, isolation, purification and/or detection of immune complexes.

EXAMPLES

Materials and Methods

Virus and Viral DNA.

The 6618 strain of PAV-3 was propagated in the swine testis (ST) cell line and in E1-transformed porcine retinal cells (VIDO R1, see below). Porcine embryonic retinal cells were obtained from the eyeballs of piglets delivered by caesarian section two weeks before the parturition date. Uninfected cells were grown in MEM supplemented with 10% fetal bovine serum (FBS). MEM with 2% FBS was used for maintenance of infected cells. Viral DNA was extracted either from infected cell monolayers by the method of Hirt (1967) *J. Mol. Biol.* 26:365-369, or from purified virions as described by Graham et al. (1991) in "Methods in Molecular Biology" Vol. 7, Gene transfer and expression protocols, ed. E. J. Murray, Humana Press, Clifton, N.J., pp. 109-128.

Plasmids and Genomic DNA Sequencing.

Selected restriction enzyme fragments of PAV-3 DNA were cloned into pGEM-3Z and pGEM-7Zf(+) plasmids (Promega). Nucleotide sequences were determined on both strands of the genome by the dideoxy chain-termination method using Sequenase® enzyme (U.S. Biochemicals) and the dye-terminator method with an Applied Biosystems (Foster City, Calif.) DNA sequencer.

cDNA Library.

A cDNA library was generated from polyadenylated RNA extracted from PAV-3 infected ST cells at 12 h and 24 h post infection. Double stranded cDNAs were made with reagents from Stratagene and cloned into Lambda ZAP vector. Plaques which hybridized to specific restriction enzyme fragments of PAV-3 DNA were plaque purified twice. Plasmids containing cDNAs were excised from the Lambda ZAP vector according to the manufacturer's protocol. The resulting plasmid clones were characterized by restriction endonuclease analysis and by sequencing of both ends of the cDNA insert with T3- and T7-specific primers. Selected clones were sequenced with internal primers. cDNA sequences were aligned with genomic sequences to determine the transcription map.

Viral Transcript Mapping by Nuclease Protection

Transcript mapping was conducted according to the method of Berk et al. (1977) *Cell* 12:721-732.

Example 1

Development of an E1-Complementing Helper Cell Line (VIDO R1)

Primary cultures of porcine embryonic retina cells were transfected with 10 μg of plasmid pTG 4671 (Transgene, Strasbourg, France) by the calcium phosphate technique. The pTG 4671 plasmid contains the entire E1A and E1B sequences (nts 505-4034) of HAV-5, along with the puromycin acetyltransferase gene as a selectable marker. In this plasmid, the E1 region is under the control of the constitutive promoter from the mouse phosphoglycerate kinase gene, and the puromycin acetyltransferase gene is controlled by the constitutive SV40 early promoter. Transformed cells were selected by three passages in medium containing 7 μg/ml puromycin, identified based on change in their morphology from single foci (i.e., loss of contact inhibition), and subjected to single cell cloning. The established cell line was first tested for its ability to support the growth of E1 deletion mutants of HAV-5. Subsequently the cell line was further investigated for the presence of E1 sequences in the genome by PCR, expression of the E1A and E1B proteins by Western blot, and doubling time under cell culture conditions. E1 sequences were detected, and production of E1A and E1B proteins was demonstrated by immunoprecipitation (FIG. 3). Doubling time was shorter, when compared to that of the parent cell line. Example 3, infra, shows that this cell line is capable of complementing a PAV E1A deletion mutant.

To assess the stability of E1 expression, VIDO R1 cells were cultured through more than 50 passages (split 1:3 twice weekly) and tested for their ability to support the replication of E1-deleted HAV-5. Expression of the E1A and E1B proteins at regular intervals was also monitored by Western blot. The results indicated that the VIDO R1 line retained the ability to support the growth of E1-deleted virus and expressed similar levels of E1 proteins during more than 50 passages in culture. Therefore, VIDO R1 can be considered to be an established cell line.

Example 2

Construction of a Full-Length Infectious Clone of PAV-3

A plasmid clone containing a full-length copy of the PAV-3 genome (pPAV-200) was generated by first constructing a plasmid containing left- and right-end sequences of PAV-3, with the PAV-3 sequences bordered by PacI sites and separated by a PstI restriction site (pPAV-100), then allowing recombination between PstI-digested pPAV-100 and an intact PAV-3 genome. Left- and right-end sequences for insertion into pPAV-100 were produced by PCR amplification, as follows.

The plasmid p3SB (Reddy et al., 1993, *Intervirology* 36:161-168), containing the left end of PAV-3 genome (position 1-8870) was used for amplification of the first 433 bp of the PAV-3 genome by PCR. Amplification primers were oligonucleotides 1 (5'-GCGGATCCTTAATTAA CATCATCAATAATATACCGCACACTTTT-3') (SEQ ID NO.: 2) and 2 (5'-CACCTGCAG ATACACCCACACACGTCATCTCG-3') (SEQ ID NO.: 3). In the sequences shown here, adenoviral sequences are shown in bold/underlined and engineered restriction enzyme sites are italicized.

For amplification of sequences at the right end of the PAV-3 genome, the plasmid p3SA (Reddy et al., 1993, supra) was used. This plasmid was used as template in PCR for amplification of the terminal 573 bp of the genome using oligonucleotide 1 (above) and oligonucleotide 3 (5'-CACCTGCAG CCTCCTGAGTGTGAAGAGTGTCC-3') (SEQ ID NO.: 4). The primers were designed based on the nucleotide sequence information described elsewhere (Reddy et al., 1995c, supra; and Reddy et al, 1997, supra).

For construction of pPAV-100, the PCR product obtained with oligonucleotides 1 and 2 was digested with BamHI and PstI restriction enzymes and the PCR product obtained using primers 1 and 3 was digested with PstI and PacI enzymes. Modified bacterial plasmid pPolyIIsn14 was digested with BamHI and PacI enzymes. This plasmid was used based on its suitability for homologous recombination in *E. coli*. The two PCR products described above were cloned into pPolyIIsn14 by three way ligation to generate the plasmid pPAV-100 which carries both termini of PAV-3, separated by a PstI site and bordered by PacI restriction enzyme sites.

Plasmid pPAV-200, which contains a full length PAV-3 genome, was generated by co-transformation of *E. coli* BJ 5183 recBC sbcBC (Hanahan, 1983, *J. Mol. Biol.* 166:557-580) with PstI-linearized pPAV-100 and the genomic DNA of PAV-3. Extensive restriction enzyme analysis of pPAV-200 indicated that it had the structure expected of a full-length PAV-3 insert, and that no unexpected rearrangements had occurred during recombination in *E. coli.*

The infectivity of pPAV-200 was demonstrated by lipofectin transfection (Life Technologies, Gaithersburg, Md.) of ST cells following PacI enzyme digestion of the plasmid to release the viral genome from the plasmid. Viral plaques were evident 7 days following transfection, and titers were equivalent to, or higher than, those obtained after infection with wild-type PAV. The plaques were amplified and the viral DNA was extracted and analyzed by restriction enzyme digestion. The viral DNA obtained by cleavage of pPAV-200 with PacI contained an extra 3 bases at each end; but these extra bases did not substantially reduce the infectivity of the PAV genome excised from pPAV-200. In addition, the bacterial-derived genomes lacked the 55-kDa terminal protein that is covalently linked to the 5' ends of adenoviral DNAs and which enhances infectivity of viral DNA.

Example 3

Generation of E1 Deletion Mutants of PAV-3

Figure 4:
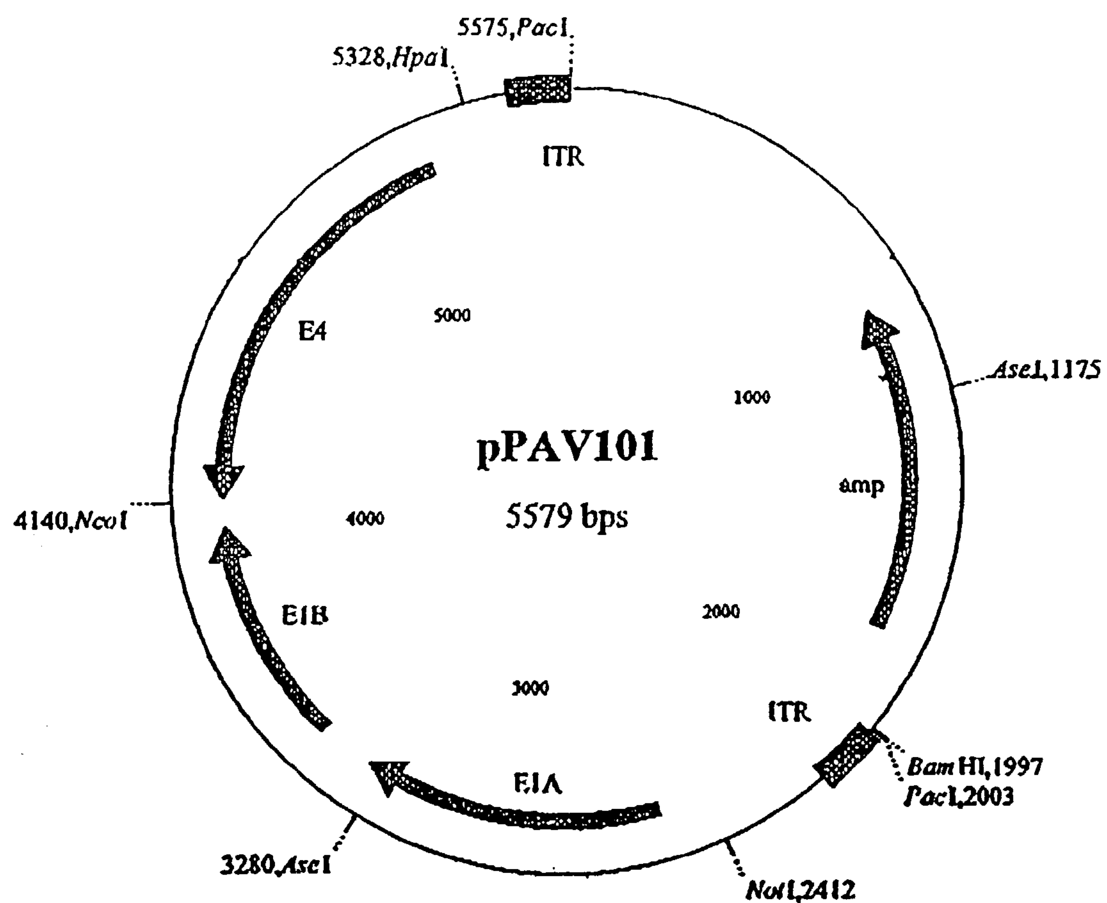
Figure 5:
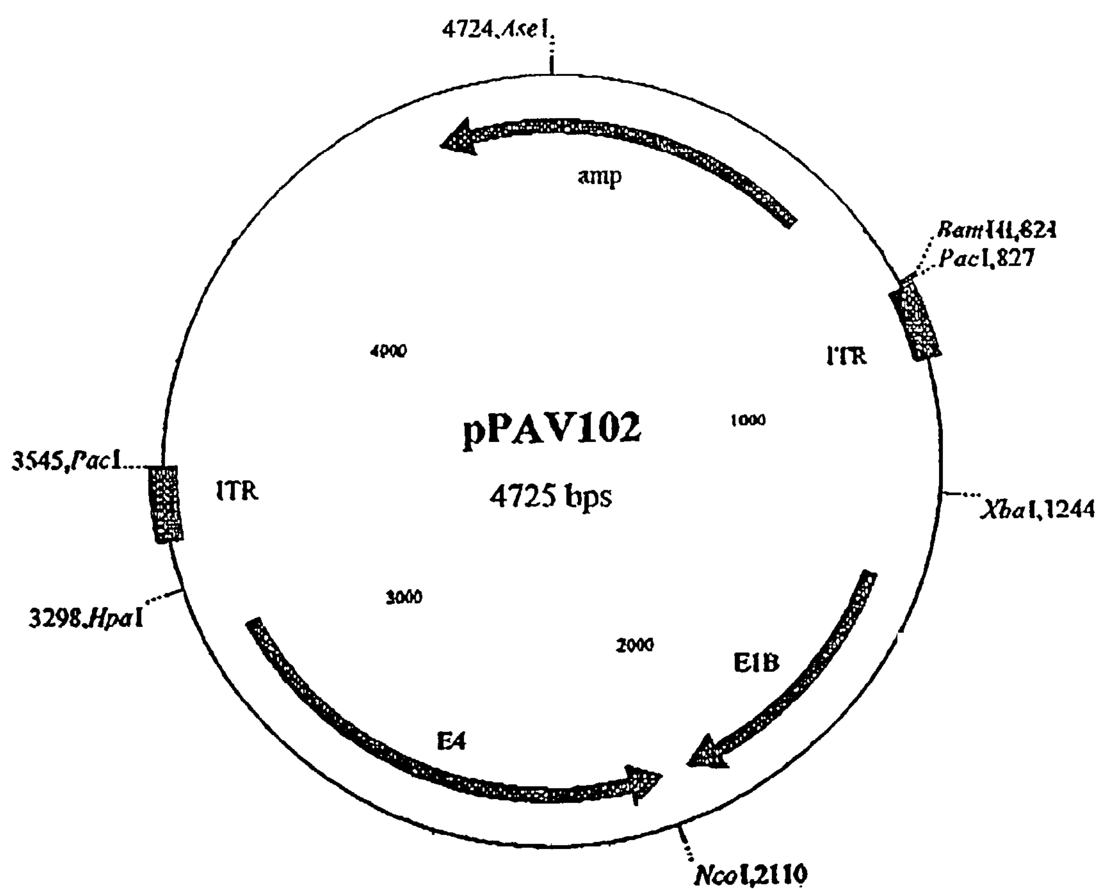

A plasmid (pPAV-101) containing the left (nucleotides 1-2,130) and the right (nucleotides 32,660-34,094) terminal NcoI fragments of the PAV-3 genome was constructed by digesting pPAV-200 with the enzyme NcoI (which has no recognition sites in the vector backbone, but many sites in the PAV insert), gel-purifying the appropriate fragment and self-ligating the ends. See FIG. 4. The E1A sequences of pPAV-101, between nucleotides 407 and 1270 (PAV genome numbering), were deleted by digestion of pPAV-101 with NotI (recognition site at nucleotide 407) and AseI (recognition site at 1270), generation of blunt ends, and insertion of a double-stranded oligonucleotide encoding a XbaI restriction site to create a plasmid, pPAV-102, containing PAV left- and right-end sequences, separated by a NcoI site, with a deletion of the E1A region and a XbaI site at the site of the deletion. See FIG. 5. Plasmid pPAV-201, containing a full-length PAV-3 genome minus E1A sequences, was created by co-transformation of *E. coli* BJ 5183 with NcoI linearized pPAV-102 and genomic PAV-3 DNA. The resulting construct, when transfected into VIDO R1 cells following digestion with PacI restriction enzyme, produced a virus that had a deletion in the E1 region. In similar fashion, construction of a virus with deletions in E1 and E3 was accomplished by transformation of BJ 5183 cells with NcoI linearized pPAV-102 and genomic PAV-3 DNA containing an E3 deletion. These E1A deletion mutants did not grow on either ST (swine testis) cells or fetal porcine retina cells and could only be grown in the VIDO R1 cell line.

Example 4

Generation of E3 Inserts and Deletion Mutants

To systematically examine the extent of the E3 region that could be deleted, a E3 transfer vector was constructed. The vector (pPAV-301) contained a PAV-3 segment from nucleotides 26,716 to 31,064 with a green fluorescent protein (GFP) gene inserted into the SnaBI site (located at nucleotide 28,702) in the same orientation as E3. The GFP gene was obtained from the plasmid pGreen Lantern-1™ (Life Technologies), by NotI digestion followed by purification of a 732-nucleotide fragment. Similarly, another construct was made with GFP cloned into the SacI site located at nucleotide 27,789. KpnI-BamHI fragments encompassing the modified E3 regions were then isolated from these E3 transfer vectors and recombined in *E coli* with pPAV-200 that had been linearized at nucleotide position 28,702 by SnaBI digestion. Virus were obtained with a construct that had the GFP gene cloned into the SnaBI site.

To delete the non-essential portion of E3 from the transfer vector, a PCR approach was used. In this approach, the region of the PAV genome between nucleotides 27,402 and 28,112 was amplified using the following primers:

```
5'-GACTGACGCCGGCATGCAAT-3'          SEQ ID NO: 5
5'-CGGATCCTGACGCTACGAGCGGTTGTA-3'   SEQ ID NO: 6
```

In a second PCR reaction, the portion of the PAV genome between nucleotides 28,709 and 29,859 was amplified using the following two primers:

```
5'-CGGATCCATACGTACAGATGAAGTAGC-3'     SEQ ID NO: 7

5'-TCTGACTGAAGCCGACCTGC-3'            SEQ ID NO: 8
```

Figure 6:
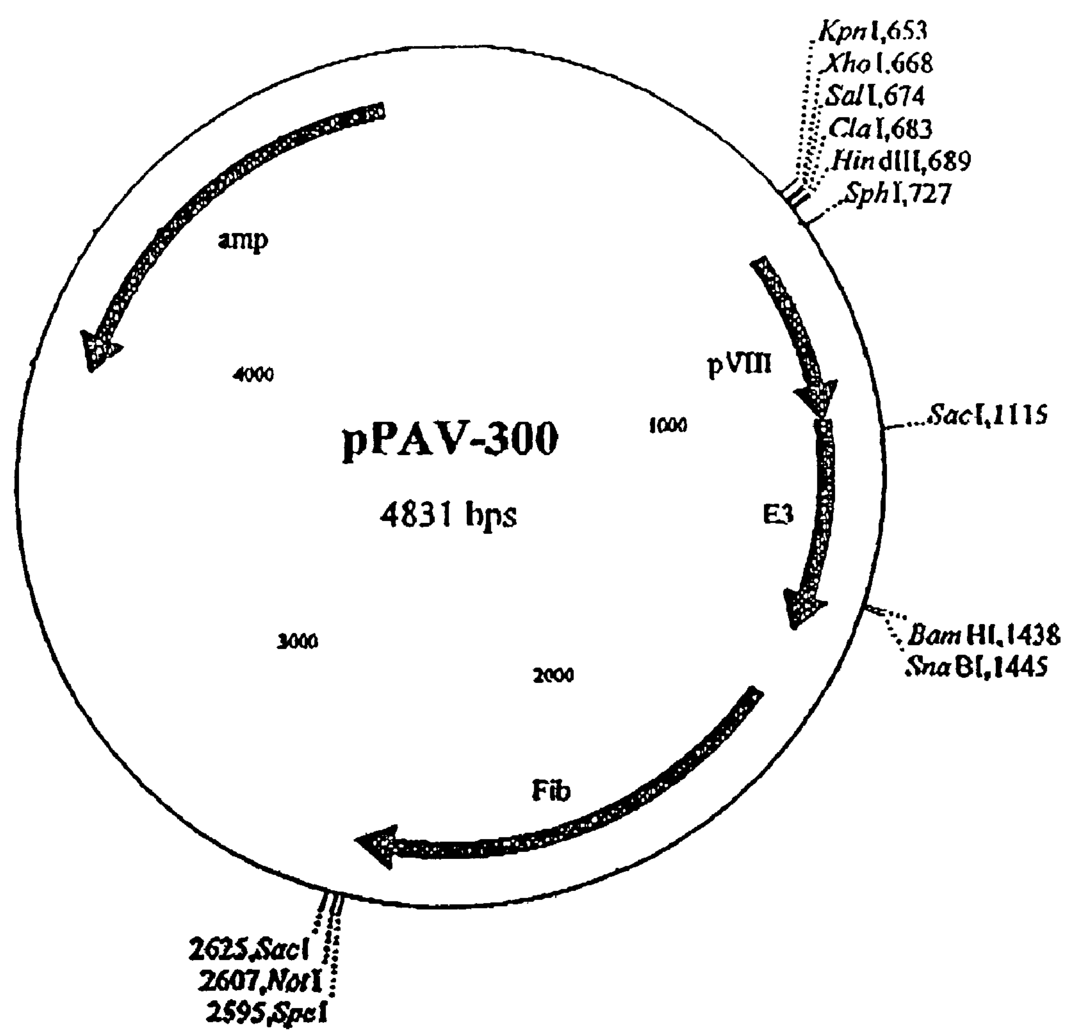

In the oligonucleotides designated SEQ ID NO: 6 and SEQ ID NO: 7, a BamHI recognition sequence is indicated by underlining. The template for amplification was a KpnI-BamHI fragment encompassing nucleotides 26,716-31,063 of the PAV genome, inserted into the plasmid pGEM3Z (Promega), and Pfu polymerase (Stratagene) was used for amplification. The first PCR product (product of amplification with SEQ ID NO: 5 and SEQ ID NO: 6) was digested with BamHI and gel-purified. The second PCR product (product of amplification with SEQ ID NO: 7 and SEQ ID NO: 8) was digested with BamHI and SpeI and gel-purified. They were inserted into SmaI/SpeI-digested pBlueScript II SK(+) (Stratagene) in a three-way ligation reaction to generate pPAV-300. See FIG. 6. pPAV-300 contains the portion of the PAV-3 genome extending from nucleotides 27,402 to 29,859, with 594 base pairs (bp) between nucleotides 28,113 and 28,707 deleted from the E3 region. A virus with such a deletion was constructed as follows: A SphI-SpeI fragment from pPAV-300, containing part of the pVIII gene, a deleted-E3 region, and part of the fiber gene was isolated (see FIG. 6). This fragment was co-transfected, with SnaBI-digested pPAV-200 (which contains a full-length PAV-3 genome) into *E. coli*. Homologous recombination generated a plasmid, pFPAV-300, containing a full-length PAV genome with a deletion in the E3 region. pFPAV-300 was digested with PacI and transfected into VIDO R1 cells (Example 1) to generate recombinant virus with a deletion in the E3 region of the genome.

Example 5

Construction of a PAV Recombinant with an Insertion of the PRV gp50 Gene in the PAV E3 Region and Expression of the Inserted Gene To construct a recombinant PAV expressing pseudorabies virus (PRV) gp50, the PRV gp50 gene was inserted at the SnaBI site of pPAV-300 to create plasmid pPAV-300-gp50. A SphI-SpeI fragment from pPAV-300-gp50, containing part of the pVII gene, a deleted E3 region with the PRV gp50 gene inserted, and part of the fiber gene, was purified and co-transfected, along with SnaBI-digested pFPAV-300 (E3-deleted) into *E. coli*. In the bacterial cell, homologous recombination generated pFPAV-300-gp50, a plasmid containing a PAV genome with the PRV gp50 gene replacing a deleted E3 region. Recombinant virus particles were obtained as described in Example 4.

Expression of the inserted PRV gp50 was tested after infection of VIDO R1 cells with the recombinant virus, by $^{35}$S labeling of infected cells (continuous label), followed by immunoprecipitation with an anti-gp50 monoclonal antibody and gel electrophoresis of the immunoprecipitate. FIG. 7 shows that large amounts of gp50 are present by 12 hours after infection, and expression of gp50 persists up to 24 hours after infection.

Example 6

Expression of the Chloramphenicol Acetyltransferase Gene from a Region that lies Between the Promoter of the E4 Region and the Right ITR The right terminal fragment of the PAV genome (encompassing nucleotides 31,054-34,094) was obtained by XhoI digestion of pPAV-200 and cloned between the XhoI and NotI sites of pPolyIIsn14. A Chloramphenicol acetyltransferase (CAT) gene expression cassette, in which the CAT gene was flanked by the SV40 early promoter and the SV40 polyadenylation signal, was inserted, in both orientations, into a unique HpaI site located between the E4 region promoter and the right ITR, to generate plasmids pPAV-400A and pPAV-400B. The modified terminal fragments were transferred into a plasmid containing a full-length PAV-3 genome by homologous recombination in *E coli* between the isolated terminal fragments and HpaI-digested pPAV-200. Recombinant viruses expressing CAT were obtained following transfection of VIDO R1 cells with the plasmids. PAV-CAT2 contained the CAT gene cassette in a leftward transcriptional orientation (i.e., the same orientation as E4 region transcription), while, in PAV-CAT6, the CAT gene cassette was in the rightward transcriptional orientation.

These recombinant viruses were tested for expression of CAT, after infection of VIDO R1 cells, using a CAT Enzyme Assay System from Promega, following the instructions provided by the supplier. See, Cullen (1987) *Meth. Enzymology* 43:737; and Gorman et al., (1982) *Mol. Cell. Biol.* 2:1044. The results are shown in Table 3.

TABLE 3

CAT activity expressed by recombinant PAV viruses

| Sample | $^3$H cpm |
|---|---|
| Mock-infected | 458 |
| CAT positive control* | 199,962 |
| PAV-CAT2 | 153,444 |
| PAV-CAT6 | 63,386 |

*the positive control sample contained 0.1 Units of purified CAT.

These results show that recombinant PAV viruses, containing an inserted gene, are viable and are capable of expressing the inserted gene.

Example 7

Construction of Replication Defective PAV-3 Expressing GFP

Figure 8:
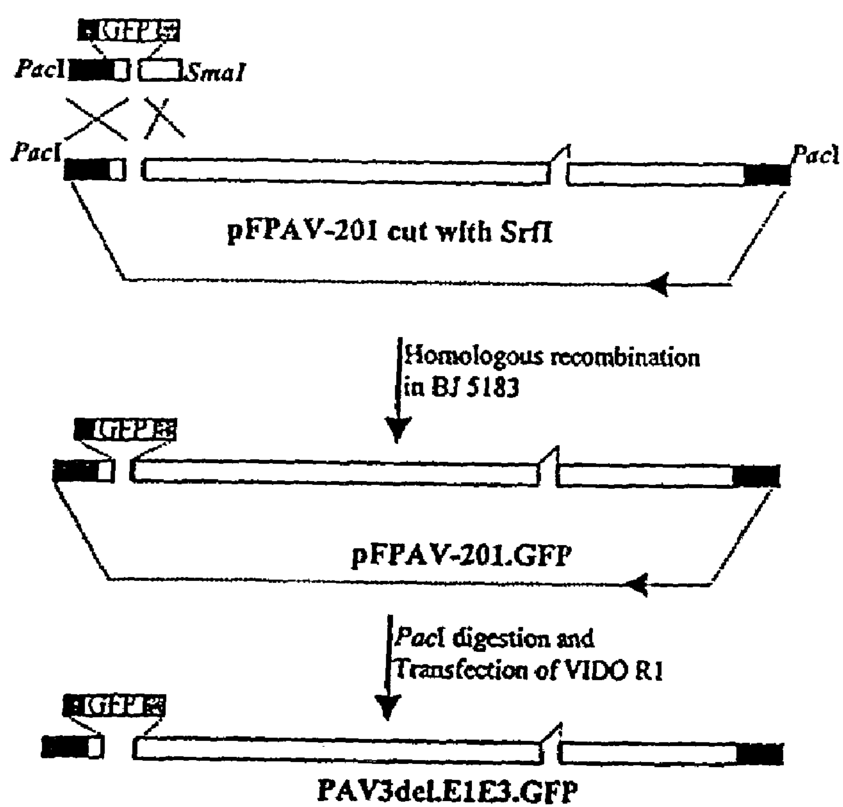

A 2.3 kb fragment containing the CMV immediate early promoter, the green fluorescent protein (GFP) gene and the bovine growth hormone poly(A) signal was isolated by digesting pQBI 25 (Quantum Biotechnology) with BglII and DraIII followed by filling the ends with T4 DNA polymerase. This fragment was inserted into the SrfI site of pPAV-102 in both orientations to generate pPAV-102GFP (FIG. 8). This plasmid, digested with PacI and Sma1 enzymes, and the fragment containing part of the E1 sequence and the GFP gene was gel purified. This fragment and the SrfI digested pFPAV-201 were used to transform *E. Coli* BJ 5183 to generate the full-length clone containing GFP in the E1 region (pFPAV-201-GFP) by homologous recombination. The recombinant virus, PAV3delE1E3.GFP was generated following transfection of VIDO R1 cells with PacI restricted pFPAV-201-GFP that had the GFP transcription unit in the opposite orientation to the E1. A similar virus with the GFP in the same orientation as E1 could not be rescued from transfected cells. Presence of the GFP gene in the viral genome was confirmed by restriction enzyme analysis. The recombinant virus replicated in VIDO R1 cells two logs less efficiently than the wild type PAV-3.

Example 8

Virus Entry and Replication of PAV-3 in Human and Animal Cells

To initially characterize the host species restriction of PAV in vitro, monolayers of 11 cell types from 6 different mammalian species were infected with wild type PAV-3 or PAV3del.E1E3.GFP. ST, VIDO R1 (porcine), 293, A549 (human), MDBK, VIDO R2 (bovine, ATCC accession number PTA 156), C3HA (mouse), COS, VERO (monkey), sheep skin fibroblasts or cotton rat lung cells were incubated with 1 pfu/cell of wild type PAV-3 or helper-dependent PAV-3 expressing GFP. The cells infected with wild type PAV were harvested at 2 h and 3 days post-infection, subjected to two cycles of freeze-thaw, and virus titers were determined on VIDO R1 cells. Cells that were infected with the recombinant virus expressing GFP were observed with the aid of a fluorescent microscope for green fluorescence.

A ten-fold increase in virus titers in Vero and COS cells, and a hundred-fold increase in cotton rat lung fibroblasts and VIDO R2 cells, was noticed. No increase in the virus titers was observed with 293, A549, MDBK, sheep skin fibroblasts, dog kidney and C3HA cells. All of these cell types showed bright green fluorescence when infected with PAV3delE1E3.GFP except human cells, which showed a weak fluorescence. In addition, low levels of GFP expression were achieved in human cells with recombinant PAV-3. These observations suggest that virus entry into some human cells is limited and/or the human cells are non-permissive for the replication of the virus. These results also demonstrated that GFP was expressed by the PAV-3 vector in cells which are semi-permissive (VERO, COS, Cotton rat lung fibroblasts and VIDO R2), or non-permissive (Sheep skin fibroblasts, MDBK and human cells) for virus replication.

Example 9

Insertions in the Regions of the PAV-3 Genome Defined by Nucleotides 145-13,555; 15,284-19,035; 22,677-24,055; 26,573-27,088; and 31,149-34,094

Insertions are made by art-recognized techniques including, but not limited to, restriction digestion, nuclease digestion, ligation, kinase and phosphatase treatment, DNA polymerase treatment, reverse transcriptase treatment, and chemical oligonucleotide synthesis. Heterologous nucleic acid sequences of interest are cloned into plasmid vectors containing portions of the PAV genome (which may or may not contain deletions of PAV sequences) such that the foreign sequences are flanked by sequences having substantial homology to a region of the PAV genome into which insertion is to be directed. Substantial homology refers to homology sufficient to support homologous recombination. These constructs are then introduced into host cells that are co-transfected with PAV-3 DNA or a cloned PAV genome. During infection, homologous recombination between these constructs and PAV genomes will occur to generate recombinant PAV genome-containing plasmids. Recombinant virus are obtained by transfecting the recombinant PAV genome-containing plasmids into a suitable mammalian host cell line. If the insertion occurs in an essential region of the PAV genome, the recombinant PAV virus is propagated in a helper cell line which supplies the viral function that was lost due to the insertion.

Example 10

Analysis of Early Region 1 of Porcine Adenovirus

Materials and Methods

Cells and Viruses

VIDO R1 (Reddy et al., 1999(b), *J. Gen. Virol.* 80:2909-2916) and Swine Testicular (ST) cells (ATCC Cat. No. CRL 1746) were grown and maintained in minimum essential medium (MEM) supplemented with 10% fetal bovine serum (FBS). The PAV strains (wild-type PAV-3 strain 6618) were propagated and titrated in VIDO R1 cells (Reddy et al., 1999 (b), supra).

GST Fusion and Antibody Production

The plasmid pE1A was created by amplifying part of E1A (nt 556 to 1222) by PCR and ligating in-frame to glutathione S-transferase (GST) gene in plasmid pGEX-5X-3. To create plasmid pE1Bs, part of $E1B^{small}$ ORF (nt 1470 to 2070) was amplified by PCR and ligated in-frame to the GST gene in plasmid pGEX-5X-3. The plasmid pE1B1 was created by amplifying complete $E1B^{large}$ ORF (nt 1831-3250) by PCR and ligated in-frame to the GST gene in plasmid pGEX-5X-3. The junctions of the sequences encoding GST-E1A, GST-$E1B^{small}$ or GST-$E1B^{large}$ were sequenced to ensure that the coding domains are in frame. The competent *Escherichia coli* strain BL121 was transformed with pE1A, pE1Bs or pE1B1 plasmids. The fusion protein(s) were induced by addition of 0.1 M isopropyl-β-$_D$-thiogalactoside and purified using sodium dodecyl sulphate (SDS)-polyacrylamide gel electrophoresis (PAGE). Rabbits were immunized subcutaneously with 300 ug of gel purified GST-E1A, GST-$E1B^{small}$ or GST-$E1B^{large}$ fusion proteins in Freund's complete followed by three injections in Freund's incomplete adjuvant at 4-weeks interval.

In Vitro Transcription and Translation

The complete coding regions of E1A, $E1B^{small}$ and $E1B^{large}$ were individually cloned into the SmaI site of plasmid pSP64 polyA creating plasmid pSP64-PE1A, pSP64-PE1Bs and pSP64-PE1B1 respectively. The plasmid DNAs were transcribed and translated in vitro by using a rabbit reticulocyte lysate coupled transcription translation system in the presence of 50 μCi of [$^{32}$S]-methionine. The in vitro translated proteins were analyzed with or without immunoprecipitation with the protein specific polyclonal rabbit serum.

Construction of PAV-3 Recombinant Plasmids

Figure 9A:
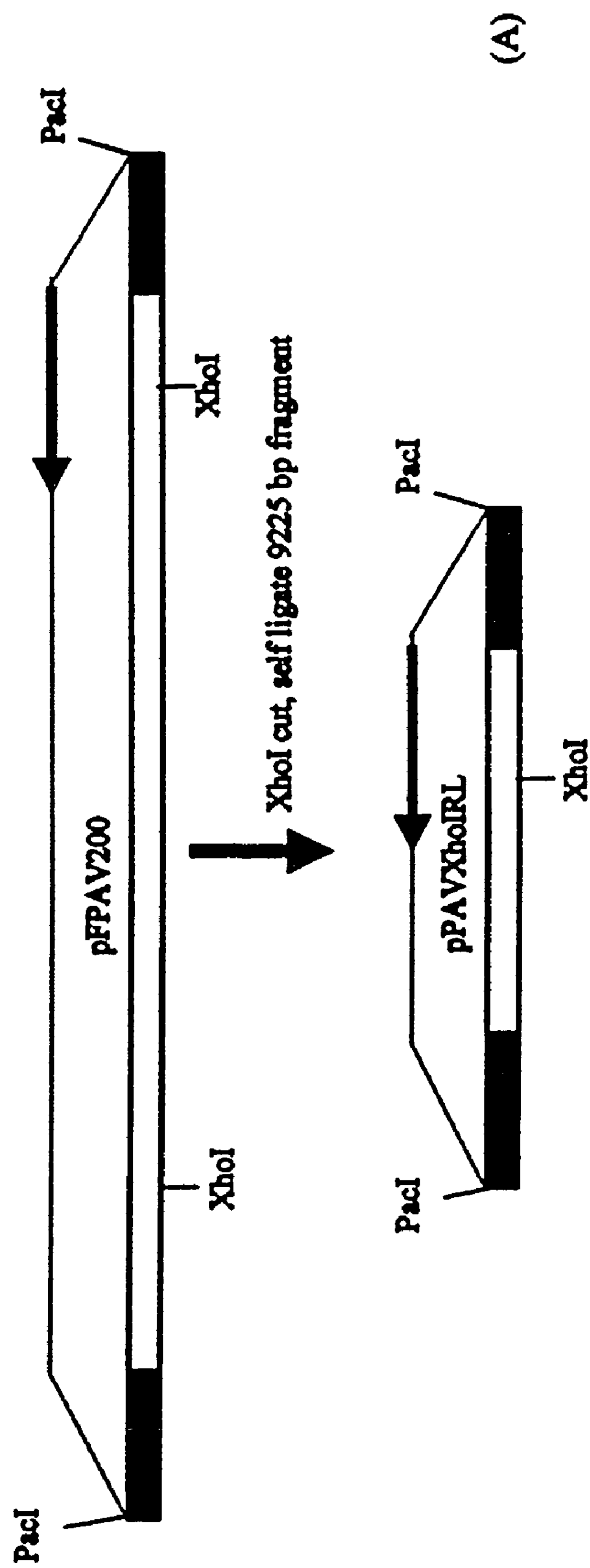
FIGS. 9A-9F provide a schematic representation of strategies used for generation of porcine genomic DNA in plasmids. (FIG. A) plasmid pPAVXhoIRL; (FIG. B) plasmid pFPAV211; (FIG. C) plasmid pFPAV212; (FIG. D) plasmid pFPAV507; (FIG. E) plasmid pFPAV214; (FIG. F) plasmid pFPAV216. ITR (filled box); The origin of DNA sequences is as follows: BAV-3 genome (open box); AmpR gene (arrow); plasmid DNA (broken line). The plasmid maps are not drawn to scale.
Figure 9B:
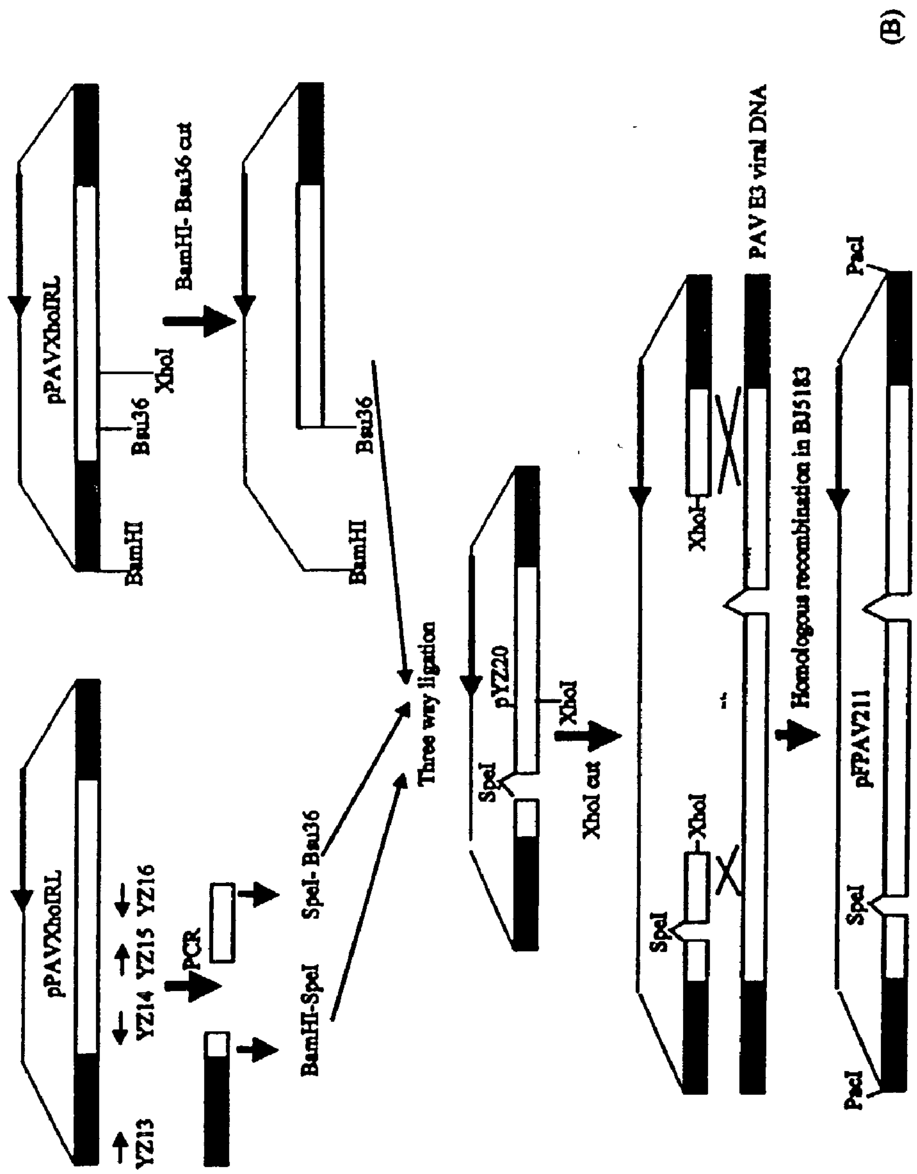
Figure 9C:
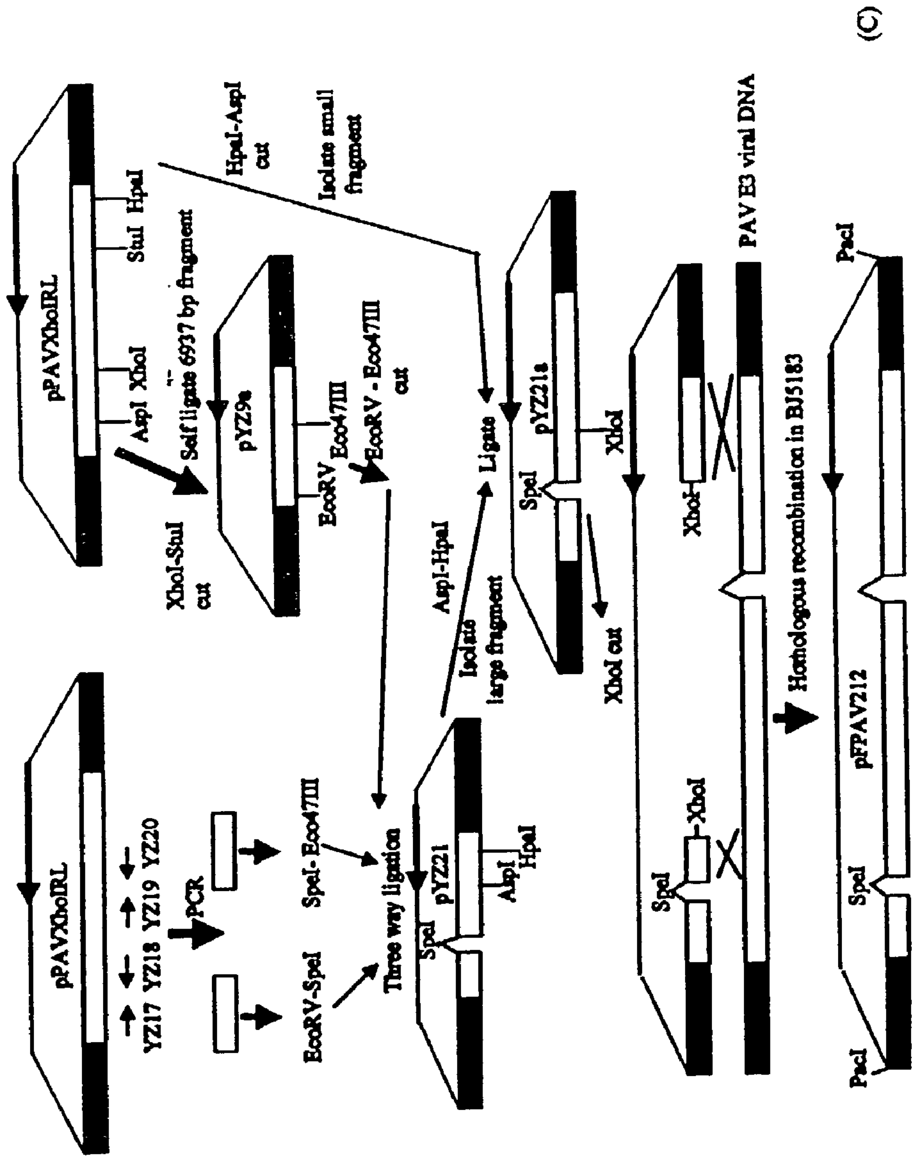
Figure 9D:
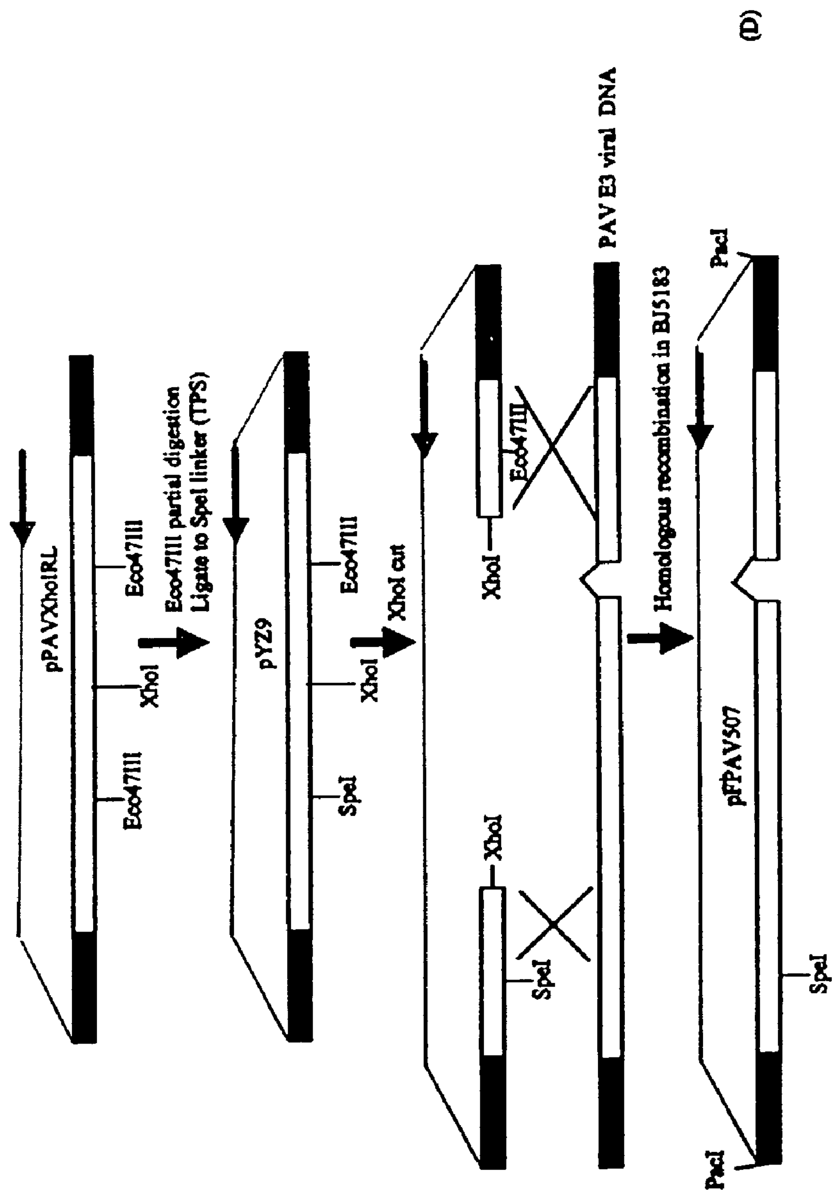
Figure 9E:
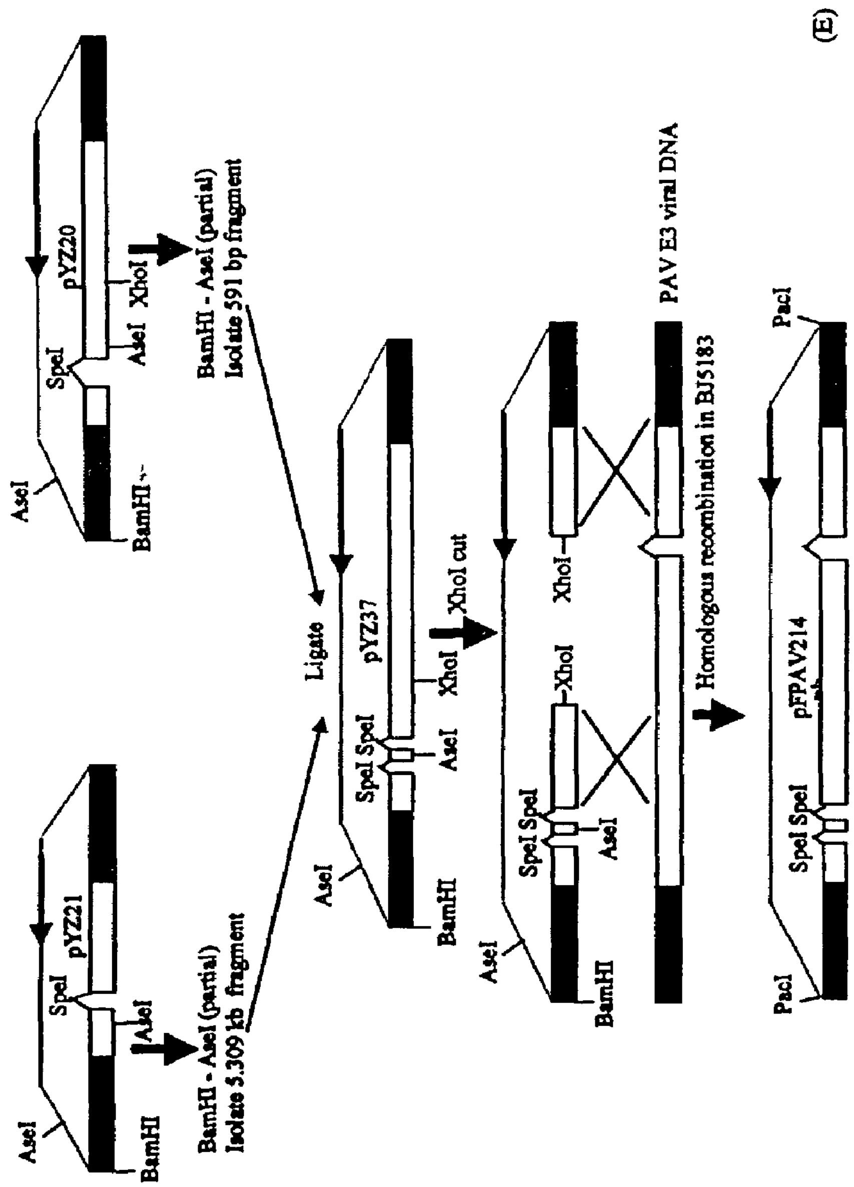
Figure 9F:
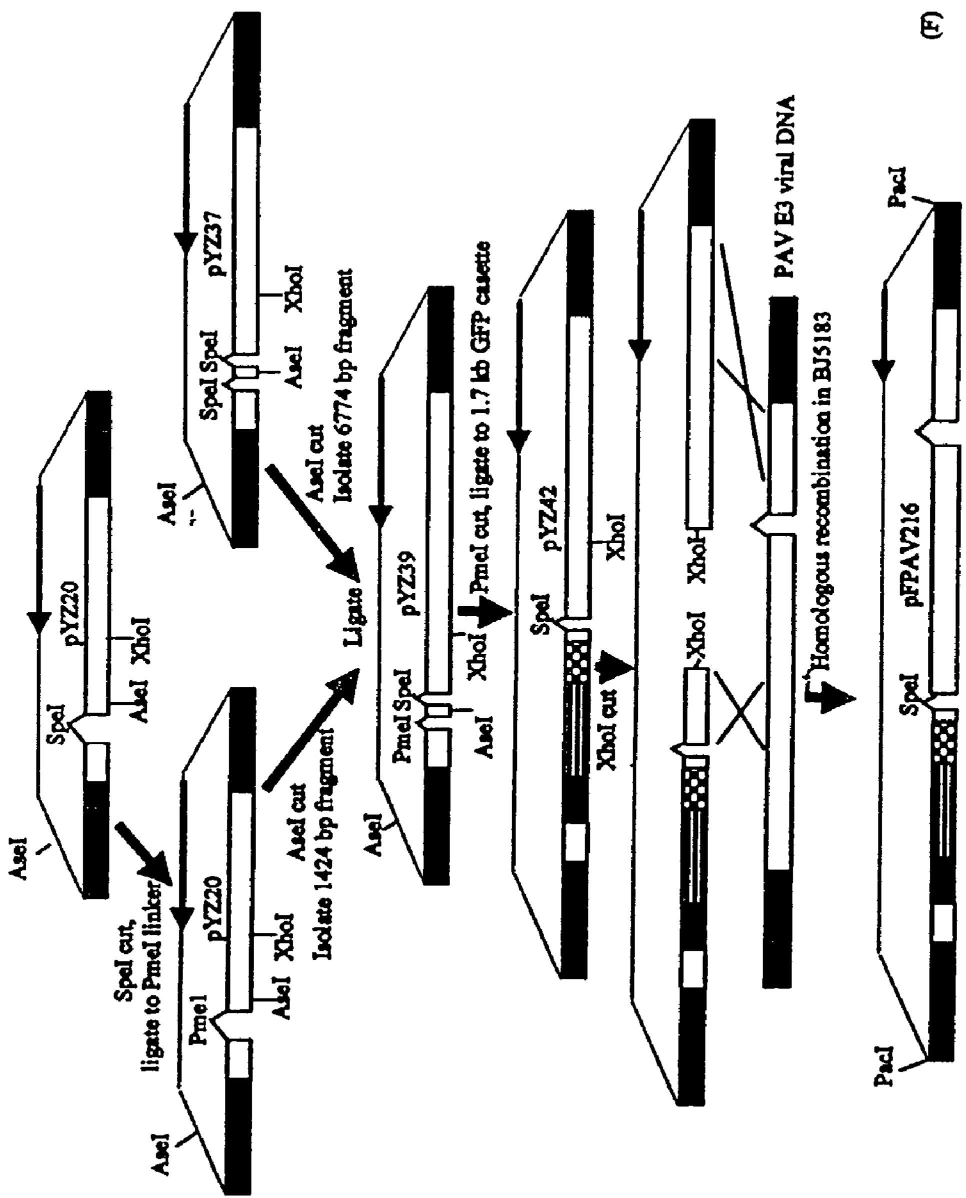

The recombinant plasmid vectors were constructed by standard procedures using restriction enzymes and other DNA modifying enzymes.

i) Construction of plasmid pFPAV211. A 9.225 kb XhoI fragment (containing vector backbone plus left [nt 004159] and right [nt 31053 to 34094] termini of PAV-3 genome) isolated from plasmid pFPAV200 (Reddy et al., 1999(a), *J. Gen. Virol.* 80:563-570) was religated creating plasmid pPAVXhoIRL (FIG. 9A). Nucleotide numbers of the PAV-3 genome referred to in this report are according to GenBank accession no. AF083132 (and are the same as in FIGS. 1-1 through 1-10). To delete the E1A region, PAV-3 genome between nucleotides (nt) 0 to 531 was amplified by using primers YZ-13 5'-ATA GGC GTA TCA CGA GGC-3' (SEQ ID NO: 9) and YZ-14 5'-CTG GAC TAG TCT GTT CCG CTG AGA GAA AAC-3' (SEQ ID NO: 10), and plasmid pPAVXhoIRL DNA as a template in a PCR reaction. The PAV-3 genomic DNA between nt 1231 and 1529 was amplified by using primers YZ-15 5'-GTG GAC TAG TCTCAT GCA GCG AACAAC C-3' (SEQ ID NO: 11) and YZ-16 5'-GTA CTA TCA CCT TCC TAA GG-3' (SEQ ID NO: 12), and plasmid pPAVXhoIRL DNA as a template in a PCR reaction. The product of first PCR was digested with BamHI-SpeI and gel purified. The second PCR product was digested with SpeI-Bsu36 and gel purified. The two gel purified fragments were cloned into BamHI and Bsu36 digested plasmid pPAVXhoIRL in a three-way ligation. The resulting plasmid pYZ20 carried 700 bp (nt 530 to 1230) deletion in E1A region and an engineered SpeI site. The recombinant PAV-3 genome containing deletions in the E1A and E3 regions (pFPAV211) was generated by homologous DNA recombination in *E.coli* BJ 5183 between XhoI linearized pYZ20 and genomic DNA of PAV-3 E3 (Reddy et al., 1999(a), supra, FIG. 1B).

ii) Construction of Plasmid pFPAV212.

A 633 bp fragment (nt 827 to 1460) isolated by PCR amplification (using oligonucleotides YZ-17 5'-ACA GTA ATG AGG AGG ATA TC-3' (SEQ ID NO: 13) and YZ-18 5'-TAG GAC TAG TCC CAC AGA AAA AGA AAA GG-3' (SEQ ID NO: 14) as primers and plasmid pPAVXhoIRL as a template) was digested with EcoRV-SpeI and gel purified. A 403 bp fragment (nt 1820 to 2223 of PAV-3 genome) isolated by PCR amplification (using oligonucleotides YZ-19 5'-ATG GAC TAG TCT TCT GGT GCC GCC ACT A-3' (SEQ ID NO: 15) and YZ-20 5'-CCT AAT CTG CTC AAA GCT G-3' (SEQ ID NO: 16) as primers and plasmid pPAVXhoIRL DNA as a template) was digested with SpeI-Eco47III and gel purified. A 6.947 kb XhoI-StuI fragment of plasmid pPAVXhoIRL was blunt end repaired with T4 polymerase and religated to create plasmid pYZ9a. The two gel purified DNA fragments were ligated to EcoRV-Eco47III digested plasmid pYZ9a in a three way ligation. The resulting plasmid pYZ21 contains 360 bp deletion (nt 1460-1820) in $E1B^{small}$ region and an engineered SpeI site. Finally, a 5.506 kb HpaI-AspI fragment of pYZ21 was ligated to 3.374 kb HpaI-AspI fragment of pPAVXhoIRL to create plasmid pYZ21a. The recombinant PAV-3 genome containing deletions in the $E1B^{small}$ and the E3 region (pFPAV212) was generated by homologous DNA recombination in *E. coli* BJ5183 between XhoI linearized pYZ21a and the genomic DNA from PAV E3 (Reddy et al., 1999(a), supra; FIG. 1C).

iii) Construction of Plasmid pFPAV507.

Plasmid pPAVXhoIRL was digested partially with Eco47III and ligated to SpeI linker (triple phase stop [TPS] codon). Plasmid pYZ9 containing SpeI linker inserted in $E1B^{large}$ ORF was selected. The recombinant PAV-3 genome containing deletion in E3 and insertion in $E1B^{large}$ (pFPAV507) was generated by homologous DNA recombination machinery in *E. coli* BJ5183 between XhoI linearized pYZ9 and the genomic DNA from PAV E3 (Reddy et al., 1999(a); FIG. 1D).

iv) Construction of Plasmid pFPAV214.

A 0.591 kb BamHI-AseI fragment was excised from plasmid pYZ20 and ligated to 5.309 bp BamHI-AseI (partial) digested pYZ21 to create plasmid pYZ36. Finally, a 4.813 kb HpaI-AspI fragment excised from plasmid pYZ36 was ligated to 3.373 kb HpaI-AspI fragment of plasmid pPAVXhoIRL to create plasmid pYZ37. The recombinant PAV-3 genome containing deletions in E1A, $E1B^{small}$ and E3 region (pFPAV214) was generated by homologous recombination in *E. coli* BJ5183 between XhoI linearized plasmid pYZ37 and genomic DNA from PAV E3 (Reddy et al., 1999a; FIG. E). The full length plasmid pFPAV214 contained 727 bp (nt 530-1230) deletion in E1A, 360 bp (nt 1460-1820) deletion in $E1B^{small}$ and 597 bp (nt 27405-28112) deletion in E3.

v) Construction of Plasmid pFPAV216.

Plasmid pYZ20 was digested with SpeI, blunt end repaired with T4 polymerase and ligated to PmeI linker (GTTTAAAC) creating plasmid pYZ39. A 1.424 kb AseI fragment of plasmid pYZ39 was isolated and ligated to 6.774 kb AseI fragment of pYZ37 to create plasmid pYZ40. Finally, a 1.730 kb NruI-PvuII fragment (containing human cytomegalovirus (HCMV) immediate early promoter, GFP gene and bovine growth hormone (BGH) poly(A) signal) was excised from plasmid pYZ41a (Zhou et al., 2001, *Virology*) and ligated to PmeI digested pYZ40 to create plasmid pYZ42. The recombinant PAV-3 genome containing GFP expression cassette insertion in E1A region of E1A, $E1B^{small}$ and E3 deleted regions was generated by homologous recombination in *E. coli* BJ5183 between XhoI linearized pYZ42 and genomic DNA from PAV E3 (Reddy et al., 1999, supra)

Transfection and Isolation of PAV-3 Mutant Viruses

VIDO R1 cell monolayers seeded in 6-well plate were transfected with 5-10 μg of PacI-digested pFPAV211, pFPAV212, pFPAV214, pFPAV216 or pFPAV507 recombinant plasmid DNAs using the Lipofectin method (Gibco BRL). After 7-10 days of incubation at 37° C., the transfected cells showing 50% cytopathic effects were collected and freeze-thawed three times. Finally, the recombinant virus was plaque purified and expanded in VIDO R1 cells.

Virus Growth Curve

VIDO R1 or ST cells were infected with mutant or wild-type PAV-3 at an MOI of 5. The infected cells, harvested at indicated times post infection were lysed in the infection medium by three rounds of freeze-thaw. Virus titers were determined by serial dilution infections of VIDO R1 cells followed by immunohistochemical detection of DNA binding protein. Titers were expressed as infectious unit (IU), in which 1 IU was defined as one positive stained focus at 3 days post infection.

Western Blot

For Western blot, about $1\times10^6$ VIDO R1 or Swine Testicular (ST) cells (ATCC catalogue no. CRL 1746) were infected with recombinant or wild-type PAV-3 at an MOI of 5. At indicated times post infection, the cells were collected and lysed in 100 μl of RIPA (0.15M NaCl, 50 mM Tris-HCl pH 8.0, 1% NP-40, 1% deoxycholate, 0.1% SDS). Proteins were resolved on SDS-PAGE under the reducing condition and electrotransferred to nitrocellulose membrane (Bio-Rad). Nonspecific binding sites were blocked with 1% bovine serum albumin fraction V, and the membrane was probed with the protein specific rabbit polyclonal serum. The membrane was washed and exposed to goat anti-rabbit IgG conjugated to alkaline phosphatase and developed using an alkaline phosphatase color development kit (Bio-Rad).

Radioimmunoprecipitation

VIDO R1 cells in six well plates were infected with wild-type PAV-3 at an MOI of 5. After virus adsorption for 1 h, the cells were incubated in MEM containing 5% FBS. At different times post-infection, the cells were incubated in methionine-cysteine free MEM for 1 h before labeling with [$^{35}$S] methionine-cysteine (100 μCi/well). After 6 or 24 h of labeling, the cells were harvested. Proteins were immunoprecipitated from cells lysed with modified radioimmunoprecipitation (RIPA) buffer and analyzed by SDS-PAGE as described previously (Tikoo et al., 1993, *J. Virol.* 67:726-733).

Results

The results of the experimentation disclosed below indicate that E1A is essential for virus replication and is required for the activation of other PAV3 early genes; E1B$^{small}$ is not essential for replication of PAV-3; and E1B$^{large}$ is essential for virus replication. The results also demonstrate expression of a desired transgene in a recombinant porcine adenovirus vector comprising a deletion in E1A, E1B$^{small}$ and E3.

Characterization of PAV-3 E1 Proteins

Figure 10:
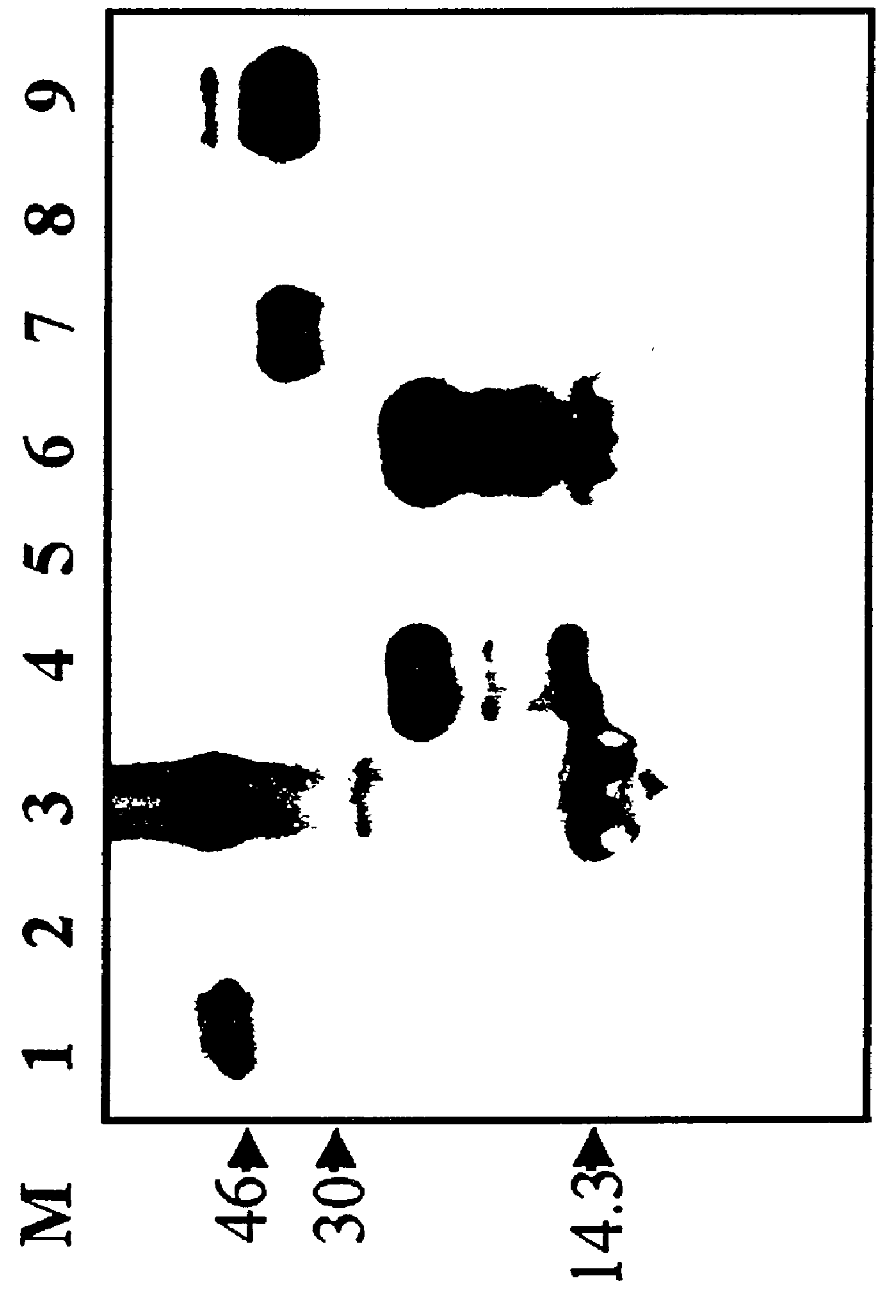

In order to identify and characterize the proteins encoded by E1 region of PAV-3, anti-E1A, anti-E1B$^{small}$ and E1B$^{large}$ sera were produced by immunizing rabbits with 300 ug of gel purified GST-protein (glutathione S-transferase) fusions. Sera collected after the final boost was analysed by in vitro transcription and translation assays to determine specificity of the antibodies in the rabbit sera. The plasmids pSP64-PE1A, pSP64-PE1Bs and pSP64-PE1B1 were generated in which coding sequence of E1A, E1B$^{small}$ and E1B$^{large}$ respectively, was placed downstream of the SP6 promoter (pSP64polyA vector containing SP6 promoter from Promega, Cat. No. P1241). In vitro translation of pSP64-PE1A RNA resulted in the synthesis of a polypeptide of 35 kDa (FIG. 10, lane 9), which was recognized by anti-E1A serum (FIG. 10, lane 7). In vitro translation of pSP64-PE1Bs RNA resulted in the synthesis of a polypeptide of 23 kDa (FIG. 10, lane 6) which was recognized by anti-E1B$^{small}$ serum (FIG. 10, lane 4). Similarly in vitro translation of pSP64-E1B1 RNA resulted in the synthesis of a polypeptide of 53 kDa (FIG. 10, lane 3), which was recognized by anti-E1B$^{large}$ serum (FIG. 10, lane 1). These proteins were not immunoprecipitated with anti-E1A serum (FIG. 10, lane 8), anti-E1B$^{small}$ serum (FIG. 10, lane 5) or anti-E1B$^{large}$ serum (FIG. 10, lane 2) from reactions in which pSP64polyA (negative control plasmid) was translated in vitro.

Figure 11:
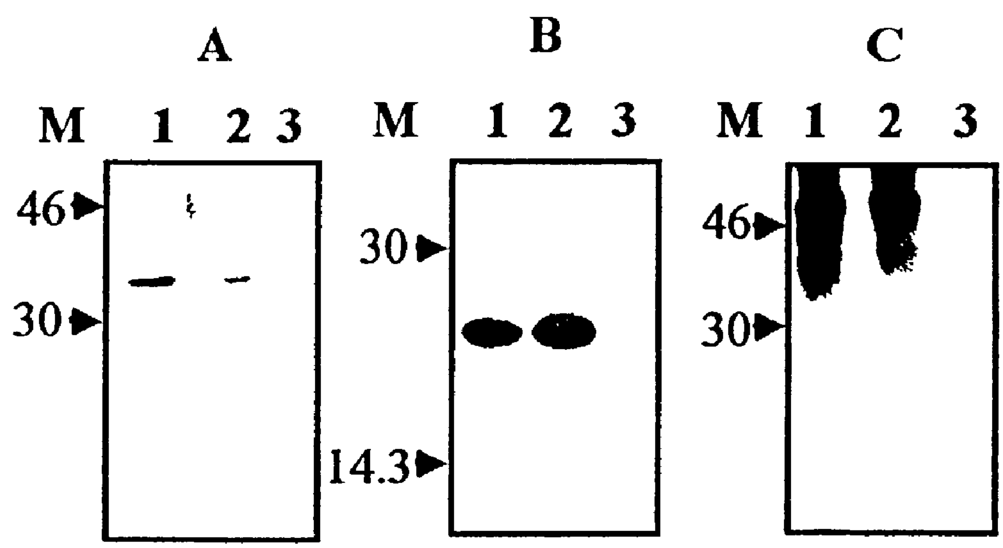
FIG. 11 shows the in vivo immunoprecipitation of E1 proteins. Proteins from the lysates of [$^{35}$S] methionine-cysteine labeled mock (lane 3) or PAV3 infected (lane 1, 6 h post infection; lane 2, 24 h post infection) VIDO R1 cells were immunoprecipitated with anti-E1A serum (panel A), anti-E1B$^{small}$ serum (panel B), anti-E1B$^{large}$ serum (panel C) and separated on 10% SDS-PAGE under reducing conditions. The positions of the molecular weight markers are indicated to the left of each panel.

To further characterize the proteins and to confirm the specificity of the antisera, radioimmunoprecipitation assays were performed. Anti-E1A serum detected a protein of 35 kDa in PAV-3 infected (FIG. 11A, lane 1-2) but not in mock-infected cells (FIG. 11A, lane 3). The 35 kDa protein was detected at 6 h (FIG. 11A, lane 1) and 24 h (FIG. 11A, lane 2) post infection. Anti-E1B$^{small}$ detected a protein of 23 kDa in PAV-3 infected (FIG. 11B, lane 1-2) but not in mock infected (FIG. 11B, lane 3) cells. The 23 kDa protein was detected at 6 h (FIG. 11B, lane 1) and 24 h (FIG. 11B, lane 2) post infection. Similarly, anti-E1B$^{large}$ serum detected a protein of 53 kDa in PAV-3 infected (FIG. 11C, lane 1-2) but not in mock infected cells. The 53 kDa protein was detected at 6 h (FIG. 11C, lane 1) and 24 h (FIG. 11C, lane 2) post infection.

Generation of PAV-3 E1 Deletion/Insertional Mutants

Figure 12A:
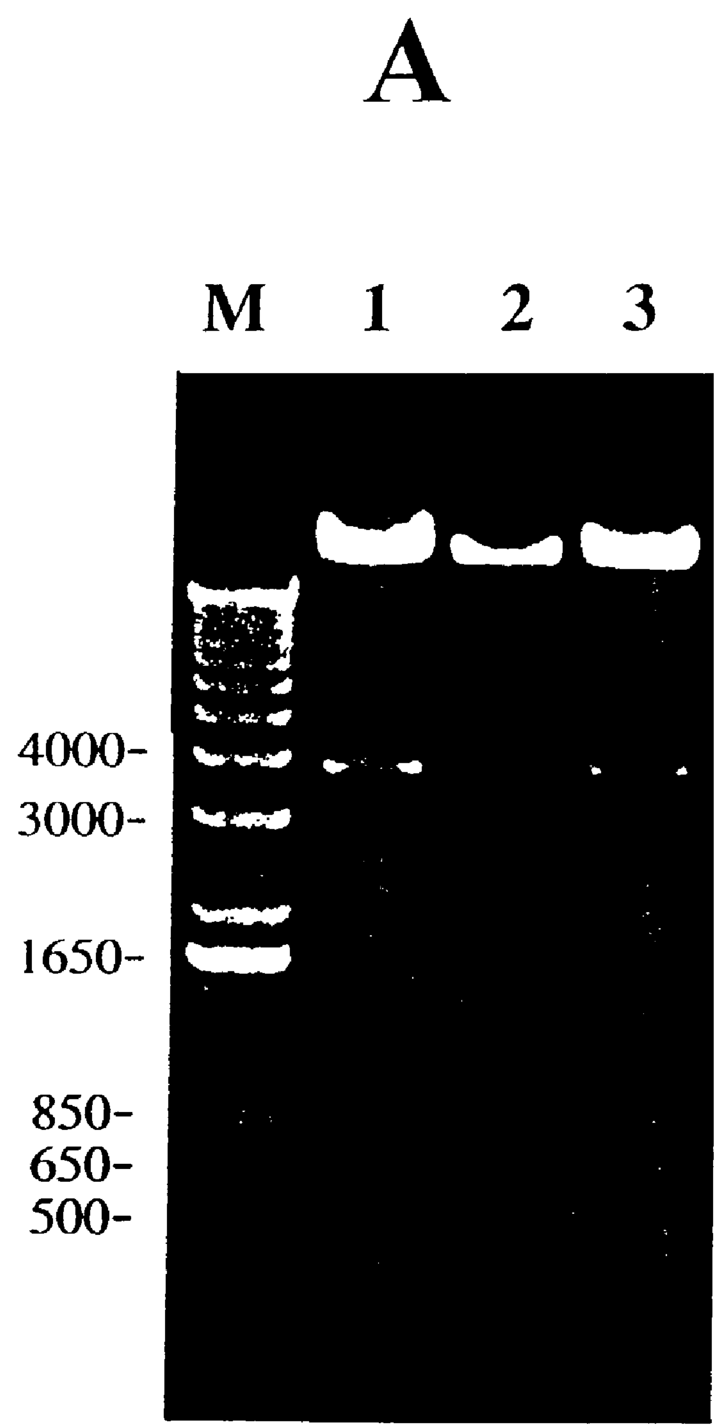
FIGS. 12A-12C provide the restriction enzyme analysis of recombinant PAV-3 genome. (FIG. A) The viral DNAs were extracted from VIDO R1 cells infected with PAV211 (lane 1), PAV212 (lane 2) or wild-type PAV-3 (lane 3) and digested with SpeI. Sizes of marker (M) are shown in basepairs. (FIG. B) The viral DNAs were extracted from VIDO R1 cells infected with PAV214 (lane 1) or wild-type PAV-3 (lane 2) and digested with NheI. Sizes of marker (M) are shown in base pairs. (FIG. C) The viral DNAs were extracted from VIDO R1 cells infected with PAV216 (lane 2) or wild-type PAV-3 (lane 1) and digested with AseI. Sizes of marker (M) are shown in base pairs.

Taking advantage of homologous recombination in *E. coli* strain BJ5183, three full-length plasmids were constructed a) pFPAV211 containing deletions in E1A (nt 530-1230) and E3 (nt 28112-28709) regions, b) pFPAV212 containing deletions in E1B$^{small}$ (nt 1460-1820) and E3 (nt 28112-28709) regions and c) pFPAV507 containing TPS codon in E1B$^{large}$ (nt 2190) and deletion of E3 (nt 28112-28709) region (all nucleotide numbers are with reference to FIG. 1). The PacI digested pFPAV211 or pFPAV212 plasmid DNAs were transfected into VIDO R1 cells and produced cytopathic effects in 10-14 days. However, repeated transfection of VIDO R1 cells with PacI digested pFPAV507 DNA did not produce any cytopathic effects. The infected cell monolayers were collected and freeze-thawed, and recombinant viruses were plaque purified and propagated in VIDO R1 cells. The recombinant PAVs were named PAV211 (E1A+E3 deletion) and PAV212 (E1B$^{small}$+E3 deletion). The viral DNA was isolated from virus infected cells by Hirt extraction method (Hirt, 1967, J. Mol. Biol. 26:365-369) and analysed by agarose gel electrophoresis after digestion with restriction enzymes. Since PAV211 and PAV212 genomes contain an additional SpeI site in place of E1A or E1B$^{small}$ regions respectively, the recombinant viral DNAs were digested with SpeI. As seen in FIG. 12A, compared with-wild-type PAV-3 (lane 3), the PAV211 (lane 1) or PAV212 (lane 2) genomes contain an additional expected band of 527 bp and 1463 bp respectively.

The ability of PAV211 and PAV212 to produce E1A and E1B$^{small}$ or DNA binding protein (DBP) was tested by Western blot analysis of these proteins from lysates of virus infected Swine Testicular (ST) cells using PAV-3 E1A, E1B$^{small}$ or DBP specific anti-serum. DBP anti-serum was prepared in the following manner. A 900-bp fragment coding for the PAV-3 DBP (amino acids 102 to 457) was amplified by PCR using primers PDBP-3 (5'-CGG GAT CCG GCC GCT GCT GCA GCT-3' (SEQ ID NO: 17)), PDBP-4 (5'-GCG TCG ACT CAA AAC AGG CTC TCA T-3'(SEQ ID NO: 18)) and plasmid PAV3c63 (DBP cDNA) (Reddy et al., 1998, *Virology* 251:414-426) DNA as a template. The PCR fragment was digested with BamHI-SalI and ligated to BamHI-SalI digested plasmid pGEX-5X-3 (Pharmacia Biotech) creating plasmid pPDBPL8. This plasmid contains the coding region of DBP (amino acids 102 to 457) fused in-frame to the C-terminus of *Schistosoma japonicum* 26-kD glutathione S-transferase (GST) gene.

Competent *Escherichia coli* BL21 were transformed with either plasmid pPDBPL8 or plasmid pGEX-5X-3. Overnight cultures of 100 ml LB broth were inoculated and grown until $OD_{600}$ reached 0.5. Cultures were induced for 4 h in 10 mM IPTG (isopropyl-1-thio-β-D-galactopyranoside). Cells were pelleted and resuspended in 5 ml PBS. The cells were lysed by sonication and the supernatant, collected after centrifugation was applied to GST column. The matrix was washed by the addition of 10 bed volumes of PBS and the fusion protein bound to the column was eluted in glutathione elution buffer. The insoluble protein retained in the cell pellet was purified by sodium dodecyl sulphate (SDS)-polyacrylamide gel electrophoresis (PAGE). The area containing the protein was excised and eluted by incubating the gel slice in 20 ml water at 4° C. overnight.

Rabbits were immunized subcutaneously with purified GST-DBP fusion protein in freund's complete adjuvant followed by two injections in Freund's incomplete adjuvant at two weeks interval and DBP anti-serum was collected.

Figure 13:
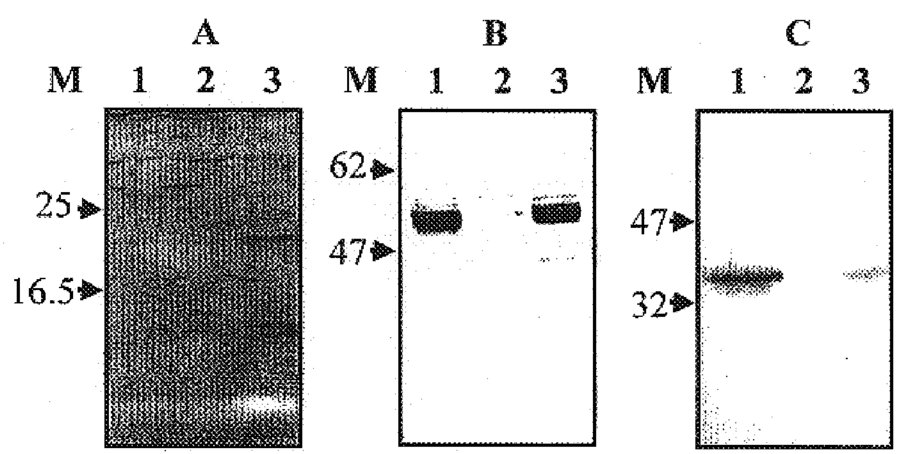
FIG. 13 shows Western blot analysis of PAV-3 protein expression in mutant infected cells. Proteins from wild-type PAV3 (lane 3), PAV211 (lane 2), or PAV212 (lane 1) infected ST cells were separated by 12.5% SDS-PAGE under reducing conditions and transferred to nitrocellulose. The separated proteins were probed in Western blots by anti-E1A (panel C), anti-E1B$^{small}$ (panel A) or anti-DBP (panel B). The positions of the molecular weight markers are shown to the left of each panel.

Wild-type PAV-3 (FIG. 13C, lane 3) or PAV212 (FIG. 13C, lane 1) infected cells produced an E1A protein of 35 kDa. No such protein was detected in PAV211 (FIG. 13C, lane 2) infected cells. Similarly, wild-type PAV-3 (FIG. 13B, lane 3) and PAV212 (FIG. 13B, lane 1) produced a DBP protein of 50 kDa. No such protein was detected in PAV211 (FIG. 13B, lane 2) infected cells. In addition, wild-type PAV-3 (FIG. 13A, lane 3) infected cells produced an E1B$^{small}$ protein of 23 kDa (FIG. 13B, lane 3). However, no such protein was detected in PAV211 (FIG. 13A, lane 2) or PAV212 (FIG. 13A, lane 1) infected cells.

Construction of E1A+E1B$^{small}$+E3 Deletion Mutant of PAV-3

Figure 12B:
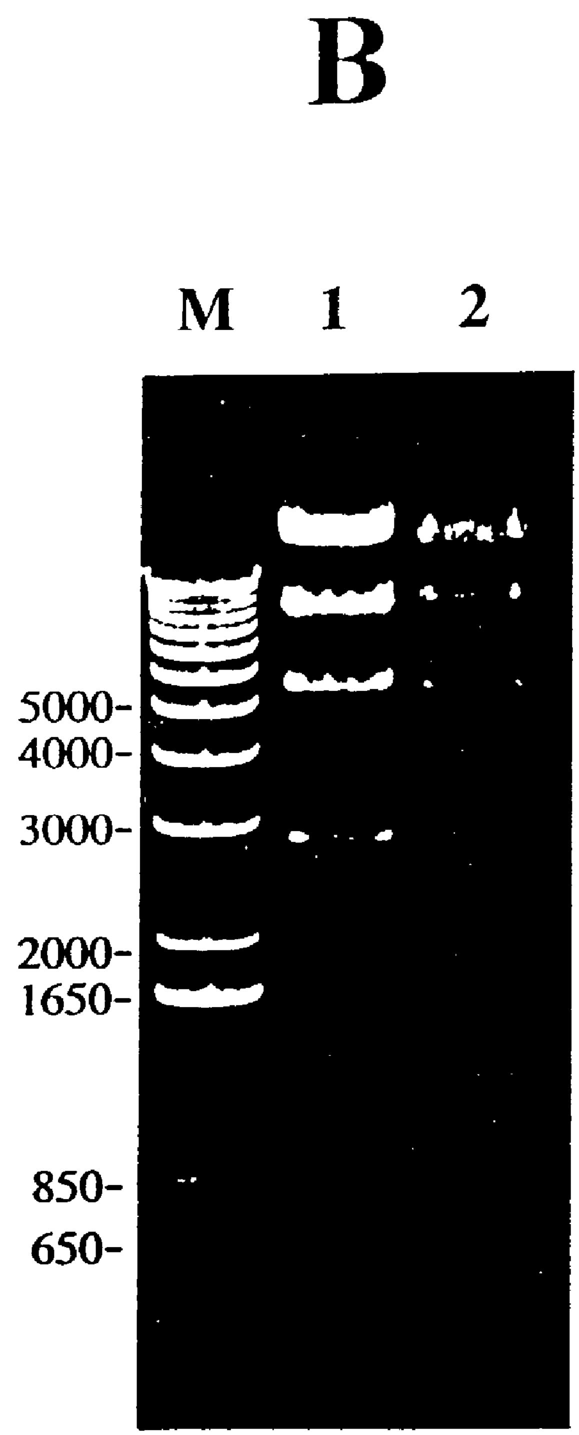

In order to increase insertion capacity of the PAV-3 vector, a full length plasmid pFPAV214 carrying deletions in E1A (nt 530-1230), E1B$^{small}$ (nt 1460-1820) and E3 (nt 28112-28709) was constructed by homologous recombination in *E.coli* BJ5183. Transfection of VIDO R1 cells with PacI digested plasmid pFPAV214 DNA produced cytopathic effects in 7-10 days. The recombinant PAV-3 named PAV214 was plaque purified and expanded in VIDO R1 cells. The viral DNA was extracted and analyzed by agarose gel electrophoresis after digestion with NheI. As seen in FIG. 12B, the wild-type PAV-3 had a fragment of 1.430 kb (lane 2) that was missing in PAV214, which instead had a fragment of 0.737 kb (lane 1).

Construction of E1A+E1B$^{small}$+E3 Deleted PAV-3 Expressing GFP

Figure 12C:
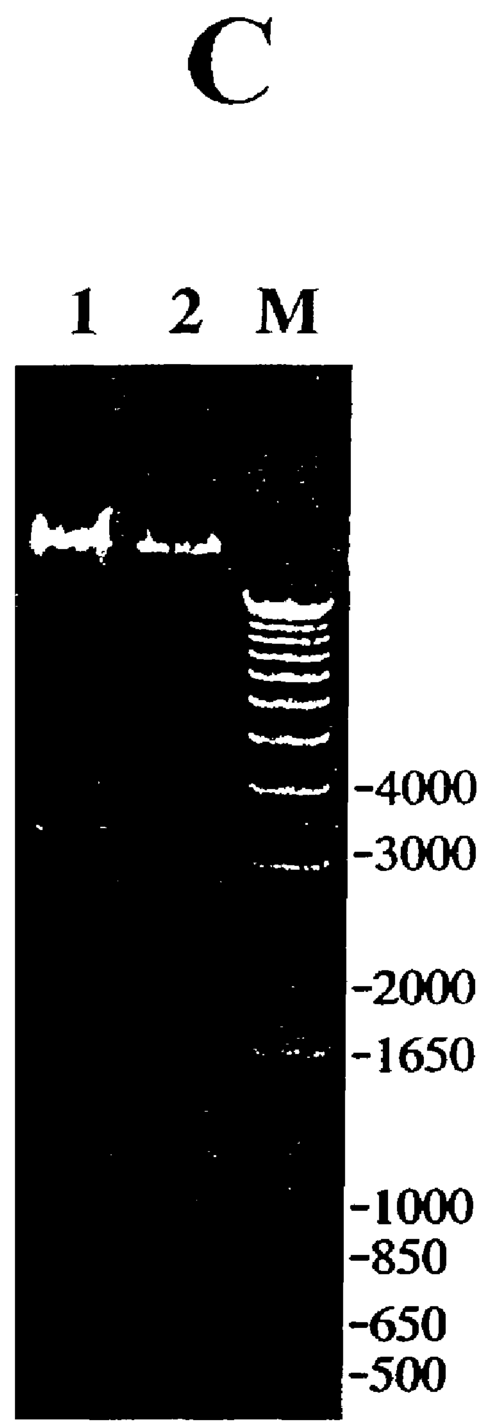
Figure 14:
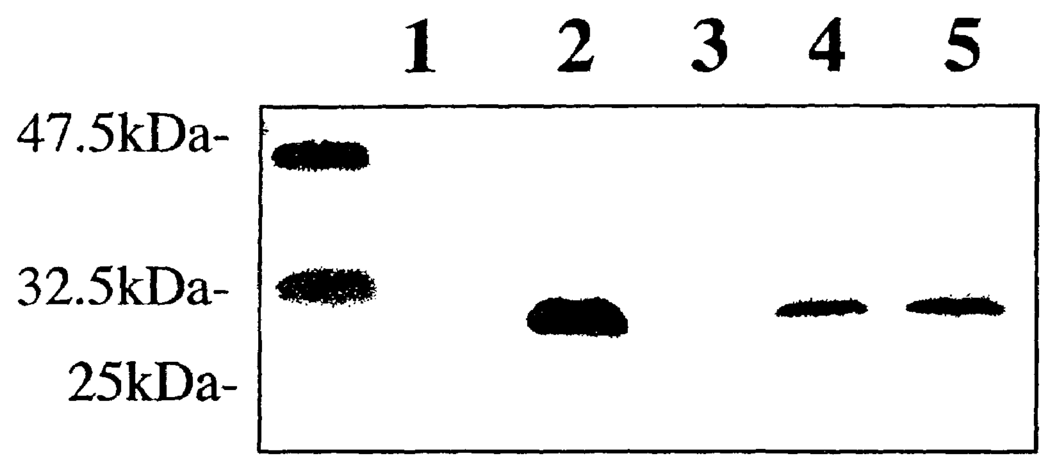
FIG. 14 shows Western Blot analysis of GFP expression. Proteins from purified GFP (lane 2) or mock (lane 1), wild-type PAV-3 (lane 3) and PAV216 (lane 4 and 5) infected VIDO R1 cells harvested at 24 h.p.i (lane 3, 4) and 48 h.p.i. (lane 5) were separated by 10% SDS-PAGE under reducing conditions and transferred to nitrocellulose. The separated proteins were probed Western blots by anti-GFP polyclonal antibody.

In order to determine if PAV214 genome (E1A, E1B$^{small}$ and E3 deleted) is useful for expression of foreign genes, a recombinant PAV-3 expressing Green fluorescent protein (GFP) was constructed. The full-length GFP gene (flanked by the HCMV promoter and BGH poly (A) signal) was inserted into the E1A region of pFPAV214 in the same transcriptional orientation as E1 (using the homologous recombination machinery of *E. coli*) creating plasmid pFPAV216. The PacI digested pFPAV216 DNA was transfected into VIDO R1 cells to isolate recombinant virus PAV216. The viral DNA was extracted and analysed by agarose gel electrophoresis after digestion with restriction enzyme. Since there is an AseI site in the CMV promoter, insertion of GFP transcription cassette in the E1A region of PAV214 genome was confirmed by AseI digestion. As seen in FIG. 12C, wild-type PAV-3 had a fragment of 1.274 kb (lane 1) that is missing in PAV216, which instead had two fragments of 0.584 kb and 1.739 kb (lane 2). Expression of GFP protein was confirmed by Western blot using GFP specific polyclonal antibody (Clonetech). As seen in FIG. 14, the GFP could be detected in PAV216 infected VIDO R1 cells at 24 h.p.i. (lane 4) and 48 h.p.i. (lane 5). The size of GFP expressed in cells infected with virus is similar to that of purified GFP protein (lane 2), which is 28 kDa in size. No such protein could be detected in mock-infected cells (lane 1) or wild-type PAV-3 infected cells (lane 3).

Growth Kinetics of PAV211, PAV212, PAV214 and PAV216

In order to determine the importance of E1A and E1B$^{small}$ in viral replication, the ability of mutant viruses to grow in VIDO R1 cells and Swine Testicular (ST) cells was compared to that of wild-type PAV-3. Virus infected cells were harvested at different times point infection, freeze-thawed three times and the cell lysates were analyzed for virus titer by DBP detection assay. Virus titers were determined as infectious units (IU) by qualitative DNA binding protein immuno-peroxidase staining. The cell monolayers in 12-well plates were infected with serial dilutions of virus. After adsorption of virus for 90 min, the cells were washed and overlaid with MEM containing 2% FBS and 0.7% agarose (Sigma, low melting temperature). On day 3 post infection, the agarose overlay was carefully removed, the cells were permeabilized with methanol/acetone (1:1 in volume) for 10 min at −20° C. and finally washed with PBS. Non-specific binding sites were blocked by incubating the cells in PBS containing 1% bovine serum albumin for 2 hr at room temperature. The blocking solution was removed and rabbit anti-PAV-3 DBP serum diluted in PBS was added to the plates. After 1 hr incubation at room temperature, the plates were washed with PBS and then processed using Vectastain Elite ABC kit (Vector Laboratories) containing biotinylated anti-rabbit IgG and HRP-steptavidin complex. Finally, the reaction was developed by the addition of substrate 3,3'-diaminobenzidine (DAB) tetrahydrochloride. Titers were expressed as IU in which 1 IU was defined as one positively stained cell/foci at 3 days post infection. Virus titres were also determined using conventional plaque assay.

Figures 15A, 15B:
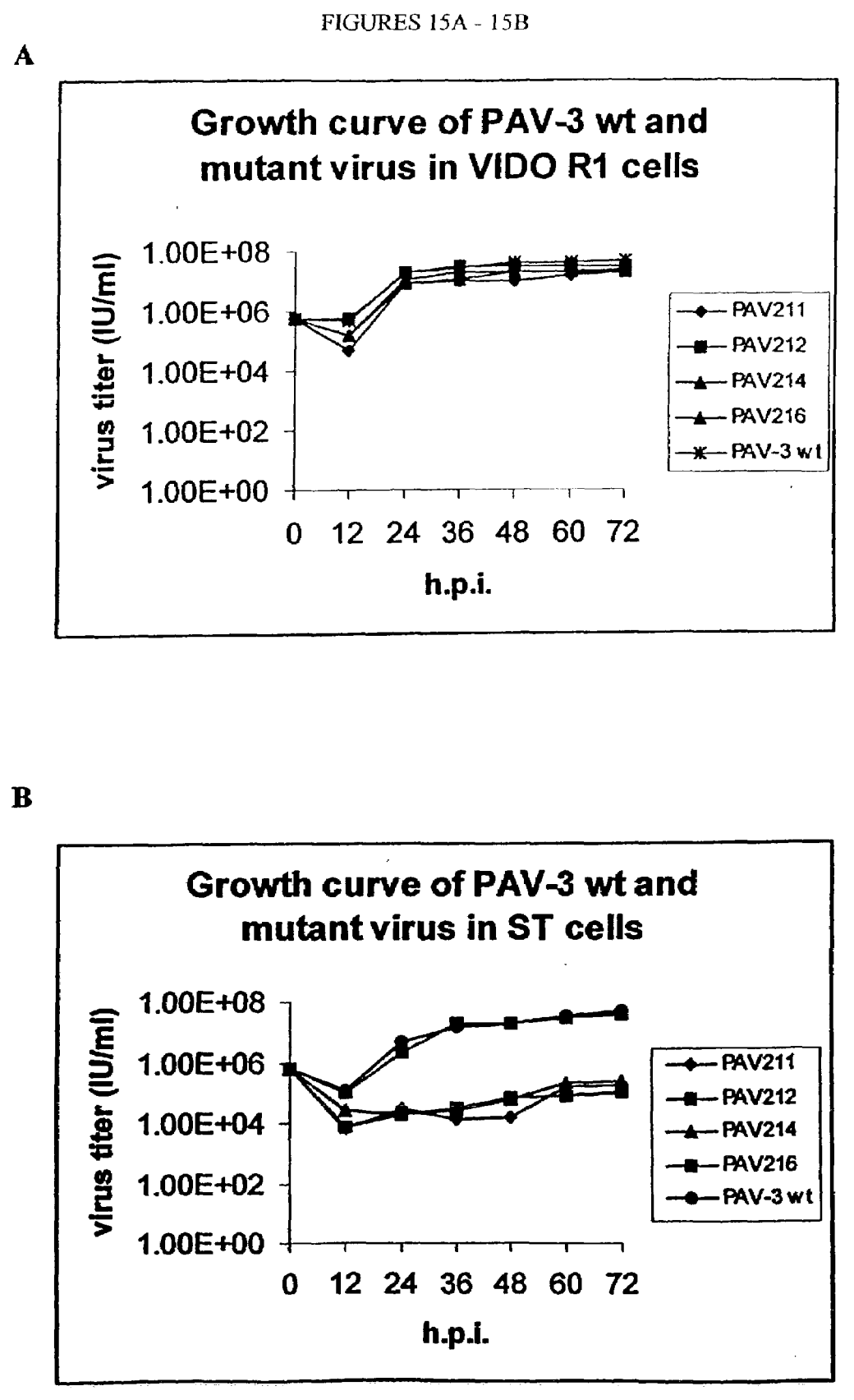

Wild-type PAV-3 titer was $5.2\times10^7$ IU\ml at 72 h p.i. on VIDO R1 cells. The titers of mutant viruses were between $2\times10^7$-$3.2\times10^7$ IU/ml, which are quite similar to that of wild-type PAV-3 virus. Therefore, PAV vectors with deletions in E1A and/or E1B$^{small}$ did not have any affect on the ability of PAV-3 to propagate in VIDO R1 cells (E1 complementing cell line) (FIG. 15A). In contrast, we could not observe any progeny virus production in PAV211, PAV214 and PAV216 infected ST cells (E1 non complementing). The virus titers at 72 h.p.i. were never more than $2\times10^5$ IU/ml, which was lower than the amount of input virus (FIG. 15B). All of these three viruses carry deletions in E1A region. Most notably, mutant virus PAV212 that carried deletions in E1B$^{small}$ region was able to grow both in complementing and non-complementing cell lines (FIGS. 15A and 15B). At 72 h.p.i. the production of PAV212 in VIDO R1 and ST cells were $3.3\times10^7$ IU/ml and $3.9\times10^7$ IU/ml respectively.

Example 11

Generation of E1-Complementing Cell Line

The production of E1-deleted adenovirus vectors relies on trans-complementation of the E1 functions in helper cells. Cell line VIDO-R1 was generated by transformation of fetal porcine retina cells with the plasmid DNA containing the E1 sequence of HAdV-5 (Reddy et al., 1999; ATCC accession number PTA-155). Using this complementing cell line the recombinant PAdV-3 with deletions in E1A (nt 530-1230); E1B$^{small}$ (nt 1460-1820) and E3 nt (28112-28709) has been rescued (Zhou and Tikoo, 2001, *Virology,* 291:68-76). However, attempts to rescue the recombinants with increased deletion size were unsuccessful. We suggested that for rescuing the E1-deleted PAdV-3 the E1 B-large protein of PAdV-3 is needed. To check this hypothesis, a new cell line, stably expressing the gene for PAdV-3 E1B-large protein was developed.

The gene encoding PAdV 3 E1B large protein was cloned into p1REShyg vector. This vector contains the human CMV promoter, the internal ribosome entry site (IRES) of the encephalomyocarditis virus and hygromyrin B phosphotransferase gene. IRES permits the translation of two open reading frames from one mRNA. VIDO-R1 cells (fetal porcine retina cells transformed with HAdV 5 E1) were transfected with pIREShygE1BL DNA and selected with hygromycin B. About 20 days post-transfection hygromycin-resistant colonies were observed. A. new cell line was established following single cell cloning and designed VR1BL.

Figures 16A, 16B:
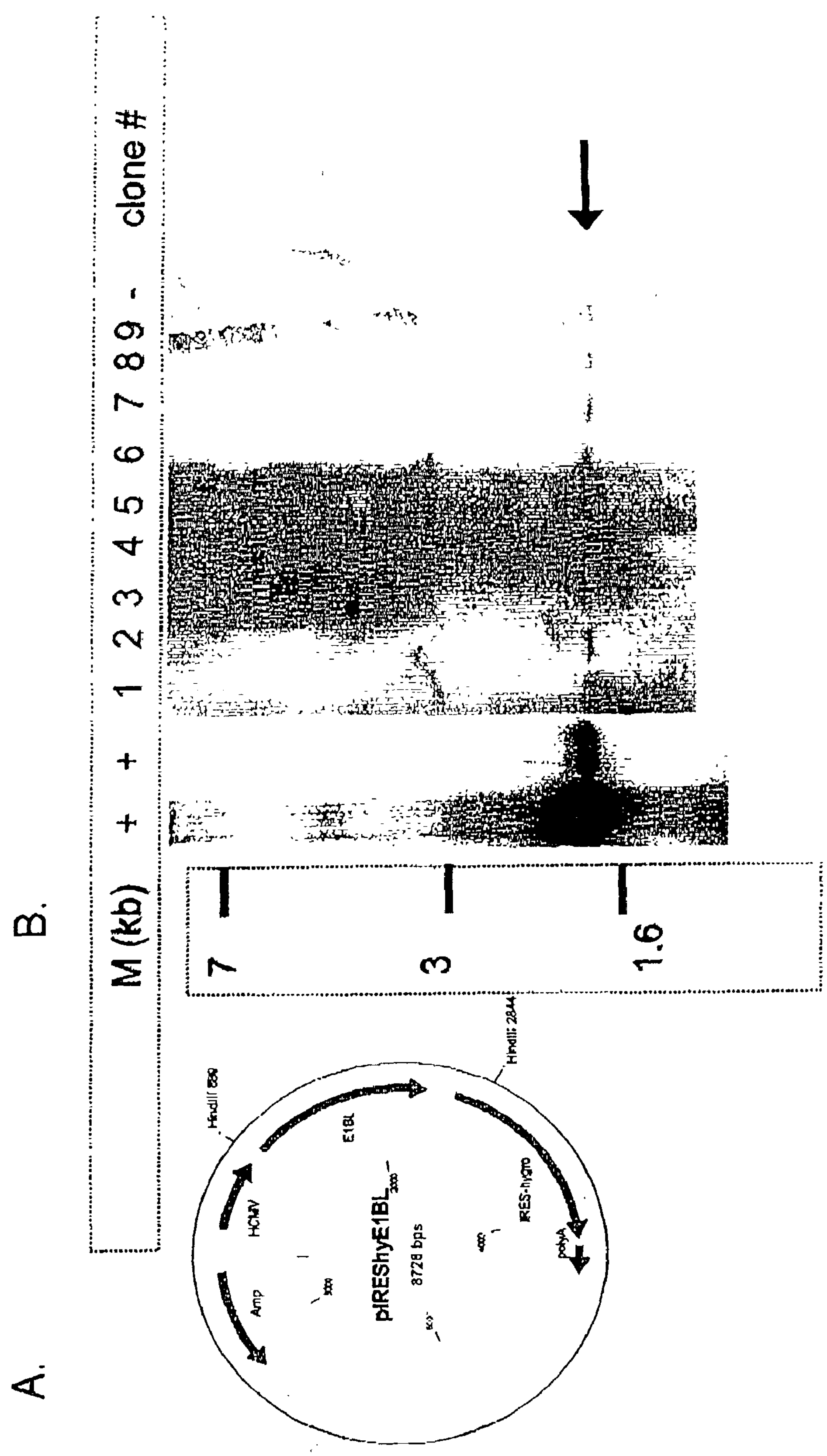
FIGS. 16A-16B.

To study whether the cell line contains PAdV-3 E1B-large sequence, integrated into the genome, Southern blotting analysis was performed on total DNA extracted from the cells. As a probe, the $^{32}$P-labeled DNA of E1B-large gene was used. This probe hybridized with the 1.9 kb-HindIII fragment of pIREShygE1BL, containing the gene for PAdV-3 E1BL (large) (FIG. 16B) that has been found in the genome of the VR1E1BL cell clones.

Figure 17:
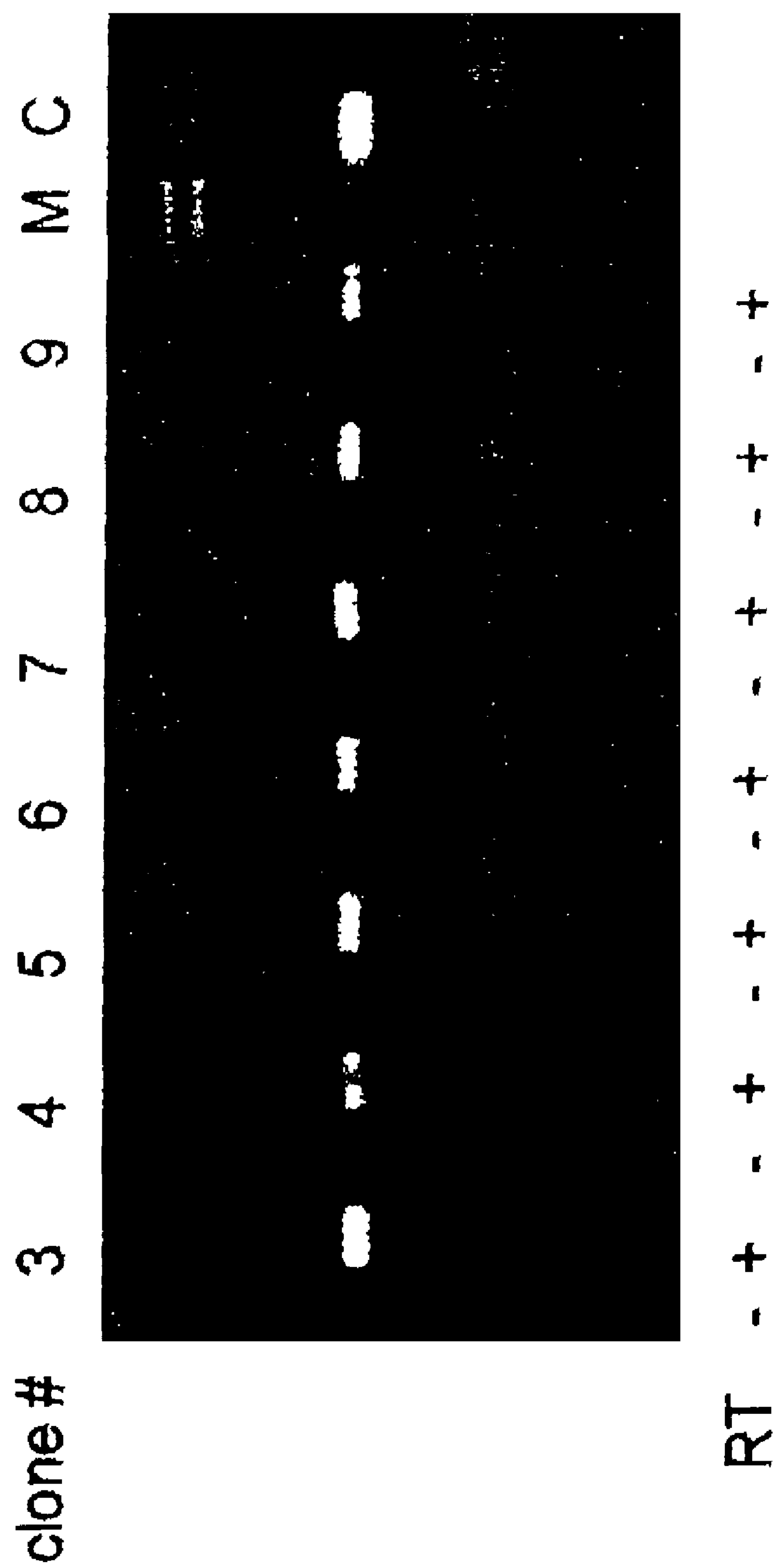
FIG. 17 shows Product of RT-PCR using DNase-treated RNA isolated from hygromycin-resistant cell clones (lane 3 to 9) and using PAdV-3 E1B-large specific primers. RT-PCR was run with (+) or without (−) reverse transcriptase. C− is a PCR on pIREShyE1BL DNA template.

To study the PAdV-3 E1B-large gene expression in the VR1BL cells, reverse transcriptase (RT) PCR was carried out using primers specific to the portion of PAdV-3 E1B-large gene. From the RT-PCR, a product of the expected size (317 bp) was obtained (FIG. 17). No PCR product was observed in "no RT" control, suggesting that this product came from mRNA template but not from DNA.

To confirm the expression of PAdV-3 E1BL protein, the VR1BL cell line was subjected to immmunofluorescence analysis, using rabbit polyclonal antisera against PAdV-3 E1B-huge protein. The VR1BL cells showed positive nuclear staining (FIGS. 18A-18B). At the same time, parent VIDO-R1 cells were negative.

Example 12

Construction of the E1-Deleted Mutants of PAdV-3

Taking advantage of homologous recombination in *E. coli* strain BJ5183, the plasmid pFPAV227 was constructed; containing full-length genome of PAdV-3 with the deletion of E1 (nt 524-3274) and a partial deletion of E3 (nt 28,112-28,709). Transfection of VR1BL cells with PacI digested pFPAV227 DNA produced cytopathic effect in 14 days.

Another plasmid called pFPAV219 contained the full-length genome of PAdV-3 with the same deletions in the E1 and E3 regions, but it had the insertion of 2320 bp DNA fragment, containing GFP-expressing cassette (human CMV promoter, bovine growth hormone poly(A) signal) in the E1 region. Transfection of VR1BL cells with PacI digested pFPAV219 DNA also produced cytopathic effect in 14 days.

The recombinant viruses named PAV219 and PAV227 were plaque-purified and expanded using VR1BL cell line. The viral DNA was extracted from the infected cells and analyzed by agarose gel electrophoresis after digestion with SpeI (FIG. 19). PAdV-3 has two SpeI sites that give 724 by DNA fragment after digestion. PAV227 genome has an addition SpeI site that has been introduced in place of E1 deletion. The SpeI-digestion of the PAV227 genome gives an additional 527 by DNA fragment. The genome of PAV219 has two SpeI sites in the GFP-expression cassette. The digestion with SpeI leads to appearing the 849 bp and 547 bp DNA fragments.

To detect GFP expression by PAV219, ST cells were infected with m.o.i. 1 $TCID_{50}$/cell and 100 $TCID_{50}$/cell. 24 h.p.i. (hours post infection) the cells were harvested and FACS analysis was performed. As seen in (FIG. 20), the infected cells were GFP-positive and the expression was virus dose-dependent.

Example 13

Infection of Human Cell Lines With PAV219

To determine if human cell lines could successfully be infected with recombinant PAdV-3 vector, the wide panel of different human cell lines was infected with PAV219 at m.o.i. 100 $TCID_{50}$/mo. 24 h.p.i. the cells were harvested and GFP expressing cells were analyzed by FACS. The result of this experiment is present in (FIG. 21).

Human embryo kidney 293 cell line is the best infectable cell line. PAV219 infects 293 cell line as well as porcine ST cells (an average 90% positive cells). PAV219 infects SAOS-2 osteosarcoma well, too (68%). HeLa and Hep2 carcinomas, U118-MG glioblastoma and MRC-5 lung fibroblasts could be infected with recombinant porcine virus (from 47% to 26% positive cells in these cell lines). The low infectable cell lines were A549 lung carcinoma and SK-N-MC neuroblastoma.

Pre-existing neutralizing antibodies against adenoviruses in the vast majority of the human population represent a major hurdle to the use of human adenovirus derived vectors for gene delivery. One of the ways to overcome this problem is a development of non-human viral vectors for human vaccination and gene therapy. PAV vectors disclosed herein can be used for human therapeutic and prophylactic purposes. Antibodies against HAdV-5 do not neutralize PAdV-3 in vitro and in vivo (Moffat et al., 2000, *Virology,* 272:159-167).

At present, adenovirus vectors are constructed by replacing the essential E1 region with a foreign gene. It is necessary to have E1 region deleted due to safety reasons. The proteins encoded by this region interfere with the processes of cell division and with the regulation of NF-kB and p53 (Russel, 2000, *J. of Gen. Virol.* 81:2573-2604). The E1-deleted viruses are replication-defective and therefore they must be propagated in a cell line that expresses E1 proteins.

VIDO-R1 cell line (porcine retina cells, transformed with HAdV-5 E1 (Reddy et al., 1999) can support the growth of E1A+E1B-small deleted PAdV-3 (Zhou and Tikoo, 2001, supra). The recombinant with insertional inactivation of the E1B-large could not be rescued using VIDO-R1 (Zhou and Tikoo, 2001, supra). It is possibly due to non-complementation of HAdV-5 55 kDa protein of the PAdV-3 E1B-large defect.

VIDO-R1 cells were transformed with the plasmid containing the gene for PAdV-3 E1B-large protein under control of human CMV promoter. The gene was followed by IRES of the encephalomyocarditis virus and hygromycin B phosphotransferase gene. This construct is expected to be very effective for stable transfection because the selective marker and gene of interest is translated from the same mRNA. Indeed, all analyzed hygromicin-resistant clones were positive for PAdV-3 E1B-large gene expression.

Using new VR1BL complementing cell line we rescued recombinant PAV227. This virus lacks the E1 region (nt 524-3274) and partially E3 (nt 28,112-28,709). This increases the safety of the vector and increases the expected packaging capacity of PAdV-3 vector up to 5 kb of foreign DNA.

The construction of PAV219, a GFP-expressing recombinant, further demonstrated the feasibility of using this vector system for foreign gene expression. The construction of this recombinant greatly facilitates the study of PAdV-3 infection of different cultured cells and animals.

PAV219 was used to screen a panel of human cell lines for the possibility of PAdV-3 infection. Human 293 cells were infected as well as swine cells. SAOS-2 osteosarcoma cells were infected very well with PAdV-3.

PAdV-3 did not infect A549 and Hep2 cells well that are well infectable with HAdV-5 (Horwitz, 1996). For HAdV-5, virus attachment to the cells is mediated by coxsackievirus and adenovirus receptor (CAR) (Bergelson et al., 1997, *Science* 275:1320-1323; Tomko et al., 1997, *P.N.A.S. USA,* 94:3352-3356). Without being bound by theory, the fact that PAdV-3 infects A459 and Hep2 cells poorly suggests that PAdV-3 uses a primary receptor that is distinct from CAR. If PAdV-3 is using a receptor distinct from CAR receptor, it is possible that some cells will be better infected by PAdV-3 than HAdV-5 and vice versa. Some of the members of Adenoviridae family use the primary receptor distinct from CAR (Xu and Both, 1998, *Virology,* 248:156-163; Stevenson et al., 1995, *J. Virol.* 69:2850-2857; Tan et al., 2001, *J. Gen. Virol.* 82: 1465-1472).

Example 14

Characterization of E4 Region

Materials and Methods

Cells and Viruses

The 6618 strain of PAV3 and all the mutant viruses were cultivated in ST cell line. Eagle's Minimum Essential Medium (MEM) with 2% fetal bovine serum (FBS) was used for growth of infected cell. Virus stocks were prepared in ST cells and viral DNA were extracted from the infected cells me the method of Hirt (1967). All the virus stocks were prepared and tittered using ST cell line.

Construction of Recombinant Plasmid

The recombinant plasmid vectors were constructed by standard procedures using restriction enzymes and other DNA-modifying enzymes as directed by the manufacturers. In order to create deletions in the PAV3 E4 region, plasmid pPAV200 containing the full-length PAV3 genome in pPOLYSYN was digested by BamHI and the 5050 bp right terminal fragment was gel-purified and self-ligated as plasmid pPAV400 which contains the whole E4 region of PAV3. A set of deletion vectors which contain deletions of orfs in E4 region of PAV3 were constructed using plasmid pPAV400 and PCR method. These deletion vectors were screened and determined using different restriction enzymes. Later, these deletion vectors were digested with restriction enzymes and the fragments with deletions were gel-purified. Homologous recombination was carried out in BJ 5183 cell line using the deletion fragments and linearized full-length genomic DNA. E4 modified full-length clones were screened and determined by the digestion with different restriction enzymes. The full-length clones with different deletions are shown in FIG. 22.

Transfection of Cells

Monolayers of ST cells grown in 60 mm dish were transfected with 5 or 7.5 ug of various PacI-digested recombinant full-length plasmid DNA using Lipofectin (Gibco BRL). Following Transfection, cells maintained in MEM containing 2% FBS at 37° C. for three to four weeks until cytopathic effects appeared. Cells showing 80% CPE were harvested and freeze-thawed three times and recombinant viruses were confirmed by restriction enzyme analysis.

Polymerase Chain Reaction

PCR was carried out to verify the deletion created in the E4 mutant viruses. ST cells were infected with the various mutant viruses and wild type PAV3, and viral DNA was extracted according to the method of Hirt (1967). PCR products were generated by using primers in the 5' and 3' flanking regions of the deletions. The 50 ul of PCR mix contained 0.2 pmol of each primer, 1× reaction buffer, 0.2 mM dNTPs, 1 U pfu polymerase, and the viral DNA template. The PCR procedure was designed with 35 cycles of denaturation at 94° C. for 30 seconds, annealing at 55° C. for 30 s, and 72° C. for 2 min. This was preceded by an initial denaturing step of 94° C. for 5 min and completed by a final extension step of 72° C. for 5 min. The PCR products were analyzed by electrophoresis in a 1% agarose gel and visualized with ethidium bromide. The results of PCR analysis are shown in FIG. 24.

Virus Growth Curve

ST cells were infected with wild-type or mutant viruses at 10000 of TCID50 in six-well plate. The infected cells were harvested at 12, 24, 36, 48 and 72 hours post infection, after three rounds of freezing-thawing, virus lysis was titrated by serial dilution infection of ST cells in 96-well plates and virus titers were expressed at $TCID_{50}$.

Example 15

Construction and Analysis of E4 Mutant Viruses

The E4 region encoded proteins of human adenoviruses show redundant properties. For the purpose of analysis of porcine adenovirus 3 E4 encoded proteins, a series of E4 mutant full-length plasmids have been constructed. Initially, each of the E4 orfs were deleted, separately, and then deletions of two neighbor orfs were conducted. All the full-length mutant plasmids were cut using PacI and the linearized plasmid DNAs were used for the transfection of the ST cell line. A series of mutant viruses containing E4 orf1, orf2, orf4, orf5, orf6, orf7, orf1&2, orf4&5, orf5&6, orf6&7 were rescued from the transfected cells eight to fifteen days later, however, we could not rescued viruses from the transfection with the full-length plasmids containing the deletion of orf3, orf2&3, orf3&4, even if we repeated the transfection several times. The results of transfection in ST cells are shown in Table 4.

TABLE 4

Results of the Transfections in ST Cells

| Full-length plasmids | Mutant viruses | CPE |
|---|---|---|
| pPAV200 | PAV200(WT) | Yes |
| pPAV200d1 | PAV401 | Yes |
| pPAV200d12 | PAV412 | Yes |
| pPAV200d2 | PAV402 | Yes |
| pPAV200d23 | PAV423 | No |
| pPAV200d3 | PAV403 | No |
| pPAV200d34 | PAV434 | No |
| pPAV200d4 | PAV404 | Yes |
| pPAV200d45 | PAV445 | Yes |
| pPAV200d5 | PAV405 | Yes |
| pPAV200d56 | PAV456 | Yes |
| pPAV200d6 | PAV406 | Yes |
| pPAV200d67 | PAV467 | Yes |
| pPAV200d7 | PAV407 | Yes |

The deletion size, location, inserted linkers, and the names of the modified full-length plasmids and the mutant viruses are summarized in Table 5.

To determine the presence of the deletion in the mutant viruses, both restriction enzyme digestion and PCR were carried out. First, the viral DNAs were isolated from mutant virus infected ST cells and digested with unique enzyme AvrII which is the inserted linker. Two bands could be observed in the mutant virus DNA samples and all the virus have the expected bands, however, only one band could be seen in the wild-type PAV3 DNA sample. The result of restriction enzyme analysis is shown in FIG. 23. Second, the specific deletions in the mutant viruses were confirmed by PCR analysis. Three sets of PCR primers from the flanking regions of the deletions were synthesized and mutant viral DNA were PCR amplified and the PCR products were visualized on 1% agarose gel. The shift of the size of PCR products from the mutant viral DNA were observed compared to the wild-type PAV3 genomic DNA and all of the mutant viral DNAs produced the expected smaller PCR bands. The results of the PCR analyses are summarized in FIG. 24.

In Vitro Analysis of PAV3 E4 Mutant Viruses

To analyze whether the single orf deletion or the combined deletions had a noticeable effect on the capacity of PAV3 to replicate in vitro, single step growth curve analysis of the mutant viruses was conducted in ST cell line. ST cells were infected with $10^4TCID^{50}$ of mutant viruses and the infected cells were harvested at 12, 24, 36, 48 and 72 h post-infection. Virus lysate from each sample was released by freeze-thawing three times and titrated on ST cell line by analysis of the $TCID^{50}$. Mutant virus with deletion of orf1, orf2, orf4, and orf1&2 grew comparable efficiencies compared to wild-type PAV3. However, the mutant viruses with deletion of orf 5, orf6, orf7, orf4&5, orf5&6, orf6&7 grew a little slower compared to PAV3.

Table 5: Characterization of E4 Mutant Viruses. The table summarizes the name of full-length plasmid with different deletions, the open-reading frames deleted, the deletion region, the deletion size, the linker inserted in the deletion region, the name of the mutant viruses and the transfection results. CPE means cytopathic effect.

TABLE 5

Characterization of E4 Mutant Viruses

| Full-length Plasmidic | Orfs Deleted | Deletion Size | Linker | Mutant Viruses | CPE |
|---|---|---|---|---|---|
| pPAV200d1 | ORF1 (33436–33636) | 201 | AvrII | PAV401 | Yes |
| pPAV200d12 | ORF1&2 (33044–33636) | 593 | AvrII | PAV412 | Yes |
| pPAV200d2 | ORF2 (33044–33404) | 361 | AvrII | PAV402 | Yes |
| pPAV200d23 | ORF2&3 (32737–33347) | 611 | SrfI | PAV423 | No |
| pPAV200d3 | ORF3 (32681–33036) | 356 | AvrII | PAV403 | No |
| pPAV200d34 | ORF3&4 (32264–33036) | 773 | AvrII | PAV434 | No |
| pPAV200d4 | ORF4 (32264–32666) | 403 | AvrII | PAV404 | Yes |
| pPAV200d45 | ORF4&5 (32103–32666) | 564 | AvrII | PAV445 | Yes |
| pPAV200d5 | ORF5 (32102–32248) | 147 | AvrII | PAV405 | Yes |
| pPAV200d56 | ORF5&6 (31834–32248) | 415 | AvrII | PAV456 | Yes |
| pPAV200d6 | ORF6 (31834–32053) | 220 | AvrII | PAV406 | Yes |
| pPAV200d67 | ORF6&7 (31303–32053) | 751 | AvrII | PAV467 | Yes |
| pPAV200d7 | ORF7 (31303–31814) | 512 | AvrII | PAV407 | Yes |
| pPAV200 | | No | No | PAV200 | Yes |

Deposit of Biological Materials

The following materials were deposited with the ATCC:

Porcine embryonic retinal cells transformed with HAV-5 E1 sequences: VIDO R1 cells were deposited at the ATCC and have ATCC accession number PTA 155.

The nucleotide sequences of the deposited materials are incorporated by reference herein, as well as the sequences of the polypeptides encoded thereby. In the event of any discrepancy between a sequence expressly disclosed herein and a deposited sequence, the deposited sequence is controlling.

While the foregoing invention has been described in some detail by way of illustration and example for purposes of clarity of understanding, it will be apparent to those skilled in the art that various changes and modifications may be practiced without departing from the spirit of the invention. Therefore the foregoing descriptions and examples should not be construed as limiting the scope of the invention.

What is claimed is:

1. A recombinant mammalian cell line that comprises a nucleic acid sequence encoding human adenovirus E1A functional protein operably linked to an expression control sequence, and wherein the cell stably expresses porcine adenovirus (PAV) $E1B^{large}$ functional protein, wherein the nucleic acid sequence encoding the PAV $E1B^{large}$ functional protein is operably linked to an expression control sequence and is integrated into the cell genome.

2. The recombinant mammalian cell line of claim 1, wherein said nucleic acid sequence encoding human E1A functional protein operably linked to an expression control sequence is integrated into the cell genome.

3. The recombinant mammalian cell line of claim 1, wherein said cell line is a porcine retinal cell line.

4. The recombinant mammalian cell line of claim 1 wherein said cell line is of porcine origin.

5. The recombinant mammalian cell line of claim 1 wherein said PAV is PAV3.

6. A method for producing a recombinant PAV that comprises introducing a PAV vector encoding the recombinant PAV into the cell line of claim 1; culturing the cell line under conditions whereby virus replication and packaging occurs; and optionally recovering virus from the infected cells; wherein the PAV vector does not contain deletions in regions essential for viral replication except within the E1 region, and wherein the PAV vector does not express functional $E1B^{large}$.

7. The method of claim 6 wherein the cell line is of porcine origin.

8. A method for producing a recombinant PAV, the method comprising:

(a) introducing, into the cell line of claim 1, a PAV vector encoding the recombinant PAV, wherein the vector comprises ITR sequences, PAV packaging sequences, and at least one heterologous nucleotide sequence, wherein said vector does not contain deletions in regions essential for viral replication except within the E1 region, and wherein the PAV vector does not express functional $E1B^{large}$:

(b) culturing the cell line under conditions whereby adenovirus virus replication and packaging occurs; and (c) optionally recovering the adenovirus from the infected cells.

9. The method of claim 8 wherein said recombinant PAV is recombinant PAV3.

10. The method of claim 8 wherein said heterologous nucleotide sequence encodes an antigen.

11. The method of claim 8 wherein said heterologous nucleotide sequence encodes a therapeutic protein.

12. The method of claim 8, wherein said vector comprises a deletion in the E3 region and/or a deletion in part or all of at least one non-essential open reading frame of the E4 region.

13. A recombinant mammalian cell line that comprises a nucleic acid sequence encoding human adenovirus E1A functional protein, and a nucleic acid sequence encoding PAV $E1B^{large}$ functional protein, wherein the nucleic acid sequence encoding the PAV $E1B^{large}$ functional protein is operably linked to an expression control sequence and is integrated into the cell genome.

* * * * *

SEQUENCE LISTING

```
<160> NUMBER OF SEQ ID NOS: 18

<210> SEQ ID NO 1
<211> LENGTH: 34094
<212> TYPE: DNA
<213> ORGANISM: Porcine Adenovirus Type 3

<400> SEQUENCE: 1

catcatcaat aatataccgc acacttttat tgcccctttt gtggcgtggt gattggcgga     60

gagggttggg ggcggcgggc ggtgattggt ggagaggggt gtgacgtagc gtgggaacgt    120

gacgtcgcgt gggaaaatga cgtgtgatga cgtcccgtgg gaacgggtca aagtccaagg    180

ggaaggggtg gagccctggg gcggtcctcc gcggggcggg gccgagcggc ggaaattccc    240

gcacaggtgg agagtaccgc gggattttgt gccctctgga ccggaccttc gccctccggt    300

gtggcacttc cgcaccacac gtccgcggcc cggtattccc cacctgacga cggtgacacc    360

actcacctga gcggggtgtc cttcgcgctg agaggtccgc ggcggccgcc cgagatgacg    420

tgtgtgggtg tattttttcc cctcagtgta tatagtccgc gcagcgcccg agagtcacta    480

ctcttgagtc cgaagggagt agagttttct ctcagcggaa cagaccctcg acatggcgaa    540

cagacttcac ctggactggg acggaaaccc cgaggtggtg ccggtgctgg aatgggaccc    600

ggtggatctg cgcgacccct ctccggggga tgagggcttc tgtgagccgt gctgggagag    660

tctggtcgat ggactgccgg acgagtggct ggacagtgtg gacgaggtgg aggtgattgt    720

gactgagggg ggtgagtcag aggacagtgg tgggagtgcc gctggtgact caggtggctc    780

tcagggggtc tttgagatgg accccccaga agagggggac agtaatgagg aggatatcag    840

cgcggtggct gcggaggtgc tgtctgaact ggctgatgtg gtgtttgagg acccacttgc    900
```

-continued

```
gccaccctct ccgtttgtgt tggactgccc cgaggtacct ggtgtgaact gccgctcttg    960
tgattaccat cgctttcact ccaaggaccc caatctgaag tgcagtctgt gctacatgag   1020
gatgcatgcc tttgctgtct atggtgagtg tttttggaca tttgtgggat tatgtggaaa   1080
aaaaggaaaa agtgcttgta agaaatctca tgtgctattt cccatttttt gtctttttag   1140
aagctgtttc tccagcacct cacaggtcgg gttccccggg acttggagac ctgccaggac   1200
gcaagaggaa gtactgctat gactcatgca gcgaacaacc tttggacctg tctatgaagc   1260
gcccccgcga ttaatcatta acctcaataa acagcatgtg atgatgactg attgtctgtg   1320
tctctgccta tatataccct tgtggtttgc agggaaggga tgtggtgact gagctattcc   1380
tcagcatcat catcgctctg ctttttttcta ctgcaggcta tttcttgcta gctcgctgtc   1440
ccttttcttt ttctgtgggc atggactatc aacttctggc caagcttact aacgtgaact   1500
accttaggaa ggtgatagta caggggtctc agaactgccc ttggtggaaa aagatttttt   1560
cggacaggtt tatcaaggta gtagcagagg ccaggaggca gtacgggcaa gagttgattg   1620
agatttttgt ggagggtgag aggggctttg gtcctgagtt cctgcgggaa gggggactgt   1680
acgaagaggc cgttctgaaa gagttggatt tcagcacctt gggacgcacc gtagctagtg   1740
tggctctggt ctgcttcatt tttgagaagc ttcagaagca cagcgggtgg actgacgagg   1800
gtattttaag tcttctggtg ccgccactat gttccctgct ggaggcgcga atgatggcgg   1860
agcaggtgcg gcaggggctg tgcatcatca ggatgccgag cgcggagcgg gagatgctgt   1920
tgcccagtgg gtcatccggc agtggcagcg gggccgggat gcgggaccag gtggtgccca   1980
agcgcccgcg ggagcaggaa gaggaggagg aggacgagga tgggatggaa gcgagcgggc   2040
gcaggctcga agggccggat ctggtttaga tcgccgccgg cccgggggag cgggtggaga   2100
ggggagcggg gaggaggcgg gggggtcttc catggttagc tatcagcagg tgctttctga   2160
gtatctggag agtcctctgg agatgcatga gcgctacagc tttgagcaga ttaggcccta   2220
tatgcttcag ccgggggatg atctggggga gatgatagcc cagcacgcca aggtggagtt   2280
gcagccgggc acggtgtacg agctgaggcg cccgatcacc atccgcagca tgtgttacat   2340
catcgggaac ggggccaaga tcaagattcg gggggaattac acggagtaca tcaacataga   2400
gccgcgtaac cacatgtgtt ccattgcggg catgtggtcg gtgactatca cggatgtggt   2460
tttgatcgg gagctaccgg cccggggtgg tctgatttta gccaacacgc acttcatcct   2520
gcacggctgc aacttcctgg gctttctggg ctcggtaata acggcgaacg ccgggggggt   2580
ggtgcgggga tgctactttt tcgcctgcta caaggcgctg gaccaccggg ggcggctgtg   2640
gctgacggtg aacgagaaca cgtttgaaaa gtgtgtgtac gcggtggtct ctgcggggcg   2700
ttgcaggatc aagtacaact cctccctgtc caccttctgc ttcttgcaca tgagctatac   2760
gggcaagata gtggggaaca gcatcatgag cccttacacg ttcagcgacg accccctacgt   2820
ggacctggtg tgctgccaga gcgggatggt gatgcccctg agcacggtgc acatcgctcc   2880
ctcgtctcgc ctgccctacc ctgagttccg caagaatgtg ctcctccgca gcaccatgtt   2940
tgtgggcggc cgcctgggca gcttcagccc cagccgctgc tcctacagct acagctccct   3000
ggtggtggac gagcagtcct accggggtct gagtgtgacc tgctgcttcg atcagacctg   3060
tgagatgtac aagctgctgc agtgtacgga ggcggacgag atggagacgg atacctctca   3120
gcagtacgcc tgcctgtgcg gggacaatca cccctggccg caggtgcggc agatgaaagt   3180
gacagacgcg ctgcgggccc cccggtccct ggtgagctgc aactgggggg agttcagcga   3240
```

-continued

```
tgacgatgac tgaggatgag tcaccccctc ccctcctctt gcaggtacgt ggccccgccc   3300
agtgggatgg gctttggatg ggggaggggt gttccctata aaagggggat gggggtggag   3360
gcatgcagcc ccacggggaa gcttgtgtgg aggatgtctt ccgagggtga gatccggacc   3420
tgcttcattt cagctcgtct tcccagctgg gccggcgtgc gtcagggagt ggccgggacg   3480
aatgtgaacg gcggagtggt gggcgcccct gcccagagcg gggtgctggc ctactcccgc   3540
ttcgttcagc agcaacagca gcagccgggg acggcggcga cggggtctgt gttccgggcg   3600
gtgtttccat cggtggatct gagcgcggag gtgggcatga tgcggcaggc gctggcggag   3660
ctgcggcagc agctgcagga gctgcgggag gtggtggaga tacagctgcg ggccacggcc   3720
tcggaggcgg ccgaggagga agaggaggag gagattgtgg tggacgagga ggtggcgccc   3780
ggcgctggag cgaacaccat ggaagaggag gaggatgaga tggtcctgac gatgactgtg   3840
gtgggggacc ctgagcctgc tggagtggaa gcccagccgc caccaccacc caccccggag   3900
agcgaccctg cggtgcctgc tactaccact accccgaagc ggctcagcta cggcgcgagc   3960
aagaggagcg gtccatgcgc ggaggacaac tgacgcggac tgtgggggga agaaggggga   4020
ggaggaaaga agaccatgga gacgggtgtt tgtctttttc cagcccaact ttattgagaa   4080
taataataaa gcttatggat gtttggaacg ataatagcgt gtccagcgtt ctctgtcttg   4140
cagggtcttg tgtatcttct cgaggcaccg gtagacctgg tgttggacgt tgaaatacat   4200
gggcatgact ccctcggcgg ggtgcaggta aagccactgg agggctgggt gcggggggca   4260
ggtgcagtag atgatccagt cataggcgtt ctggttgcgg tggtggttga aaatgtcctt   4320
gaggagcagg ctgatggcgg tgggcagacc cttggtgtag gcattgatga accggttgac   4380
ctgggcgggc tgcatgaggg gggacatgat gtggtacttg gcctggatct tgaggttgga   4440
gatgttgccg ctctggtcgc ggcgggggtt catgttgtgg aggacgacga ggacggcgta   4500
gccggtgcag cgggggaagc gggcgtgcag cttggagggg aaggcgtgga agaacttggc   4560
gacccccttg tgtccgccga ggtcctccat gcactcgtcg aggacgatgg cgatgggtcc   4620
gcgggcggcg gcgcgggcga agacgttgcg tgagtcagtg acatcatagt tgtgctcctg   4680
catgaggtcc tggtagctca tgcggacaaa gtctggcatg agggtggcgg tctgggggat   4740
tagggtgtgg tccggaccgc tgcggtagtt gccctcgcag atctgggtct cccaggcgac   4800
tacctcctgc ggggggatca tgtccacctg cggggtgatg aagaaaacag tctccggcgg   4860
gggggagagg agttgggagg agatgaggtt gcggagcagc tgggacttgc cggagccggt   4920
gggaccgtag atgacagcga tgactggctg gacctggtag ttgagggagc ggcaggtgcc   4980
agccggggtg aggaagggca tgcaggcgtt gagggtgtcg cgcaggttgc ggttctcttg   5040
gacgaggtcc tgcaggaggt gtcggcctcc cagggagagg aggtgggaga gggaggcgaa   5100
ggccttgagg ggcttgaggc cctcggcgta gggcatgtcc tgcagggcct ggtggagcac   5160
gcgcatgcgc tcccagagct cggttacatg tcccacggta tcgtcctcca gcaggtctgg   5220
ttgtttctcg ggttggggtt gctgcgtgag tacggaacga ggcggtgggc gtcgagcggg   5280
tggagggtcc ggtccttcca gggccggagg gcccgcgtga gggtggtctc ggtgacggtg   5340
aagggggcgg tctggggctg ctcggtggcc agggtcctct tgaggctgag gcggctggtg   5400
ctgaaggtgg cgcttccgag ctgcgcgtcg ttcaggtagc actggcggag gaggtcatag   5460
gagaggtgtt gggtggcatg gcccttggcg cggagcttgc cggggccgcg gtgcccgcaa   5520
gcatcgcaaa cggtgtcgcg cagggcgtag agcttggggg cgagcaggac cgtctcggag   5580
ctgtgggcgt cgctgcggca gcgctcgcac tggtctcgc actcgaccag ccaggtgagc   5640
```

-continued

```
tgggggttct ggggatcgaa gacgaggggg cccccgttcc gcttgaggcg gtgtttacct   5700
ttggtctcca tgagctcgcg tccggcgcgg gtgaggaaga ggctgtcggt gtccccgtag   5760
acggagcgca ggggccggtc ggcgatgggg gtgccgcggt cgtcggcgta gaggatgagg   5820
gcccactcgg agatgaaggc acgcgcccag gcgaggacga agctggcgac ctgcgagggg   5880
tagcggtcgt tgggcactaa tggcgaggcc tgctcgagcg tgtggagaca gaggtcctcg   5940
tcgtccgcgt ccaggaagtg gattggtcgc cagtggtagt ccacgtgacc ggcttgcggg   6000
tcggggggta taaaaggcgc gggccggggt gcgtggccgt cagttgcttc gcaggcctcg   6060
tcaccggagt ccgcgtctcc ggcgtctcgc gctgcggctg catctgtggt cccggagtct   6120
tcaggtgggt acgctacgac aaagtccggg gtgacctcag cgctgaggtt gtctgtttct   6180
atgaaggcgg aggagcggac ggagaggtcg ccgcgggcga tggcttcggt ggtgcgggcg   6240
tccatctggc tggcgaagac caccttctta ttgtcgaggc gtgtggcgaa actgccgtag   6300
agggcgttgg agagaagctt ggcgatgctg cggagcgttt ggtttctgtc ccggtcggcc   6360
ttttccttgg cagcgatgtt gagctgcacg tagtctcggg cgaggcagcg ccactcgggg   6420
aagatgctgt tgcgctcgtc cggcaggagg cgcacggccc agccacggtt gtggagggtg   6480
accacgtcca cggaggtggc tacctcgccg cggaggggct cgttggtcca gcagaggcgg   6540
ccgcccttgc gggagcagta ggggggcagg acgtccagct ggtcctcgtc ggggggggtcg   6600
gcgtcgatgg tgaagagggc gggcaggagg tcggggtcga agtagctgag ggctcgggg    6660
ccgtcgaggc ggtcctgcca gcggcgggcg gccagggcgc ggtcgaaggg gttgaggggt   6720
tggccggcgg ggaaggggtg ggtgagggcg ctggcataca tgccgcagat gtcatagacg   6780
tagaggggct cccgcaggag gccgatgaag ttggggtagc agcggccgcc gcgcaggctc   6840
ttcgcggacg tagtcataca gctcgtggga gggcgcgagg aggttcggcc gaggtgcggc   6900
gcctggggcc ggctggcgcg gtagaggagc tgcttgaaga tggcgtggga gttggagctg   6960
atggtgggcc tctggaagac attgaaggcg gcgtggggaa ggccggcctg cgtgtggacg   7020
aaggcgcggt aggactcttg cagcttgcgg accagacggg cggtgacgac gacgtcctgg   7080
gcgcagtagc gcagggtggc ctggacgatg tcgtaagcgt ccccctggct ctccttcttc   7140
cacaggtcct tgttgaggag gtactcctga tcgctgtccc agtacttggc gtgtgggaag   7200
ccgtcctgat cgcgtaagta gtcccccgtg cggtagaact cgttcacggc atcgtagggg   7260
cagtgtccct tgtccacggc cagctcgtag gccgcggcgg ccttgcggag gctggtgtgc   7320
gtgagggcga aggtgtcccg gaccatgaac ttgacgtact ggtgctgggg gtcctcgggg   7380
gccatgacgc cctcctccca gtccgcgtag tcgcggcgcg ggcggaaggc ggggttgggc   7440
aggttgaagc tgatgtcatt gaagaggatg cggccgttgc gcggcatgaa ggtgcgggtg   7500
accaggaagg aggggggcac ctcgcggcgg tgggcgagca cctgcgcggc caggacgatc   7560
tcatcgaagc ccgagatgtt gtggcccacg atgtagacct ccaggaagag gggcggcccg   7620
cgcaggcggc ggcgccgcag ctgggcatag gccagggggt cctcggggtc gtccggcagg   7680
ccggggcccc gctcctgcgc cagctcggcg aggtctgggt tgtgggccag caggtgctgc   7740
cagagggtgt cggtgaggcg ggcctgcagg gcgtgccgca gggccttgaa ggcgcggccg   7800
atggcgcgct tctgcgggca gagcatgtag aaggtgtggg ctcgggtctc cagcgctgca   7860
ggcgggctct ggacggccac cacctgcagc gcggcgtcca gcagctcctc gtcccccgag   7920
aggtggaaga ccagcaggaa gggcacgagc tgctttccga agcggccgtg ccaggtgtag   7980
```

-continued

```
gtctccaggt cataggtgag gaagaggcgg cgggtgccct cgggggagcc gatggggcgg   8040
aaggcgatgg tctgccacca gtcggccgtc tggcgctgaa cgtggtggaa gtagaagtcc   8100
cggcggcgca cggagcaggt gtgggcggtc tggaagatgc ggccgcagtg ctcgcacttc   8160
tgggcctcct ggatgctctt gatgaggtgg cagcggccct gggtgaagag caggcggagg   8220
gggaagggga ggcggggcgg cgggccctcg ggcggggggt cccagcgcac gtggtgcagg   8280
tggtgttgct ggcgggtgac cacctggacg aaggtgggcc cggcggcgcg ggccagctcc   8340
accgcggtct ggggggtagc ctgcaggagg tcggggggcg ggcgcaggag gtgcagctgg   8400
aagaggttgg ccagggcgct gtcccagtgg cggtggtagg tgatgctcca gctctccccg   8460
tcctgggtgg tgccctggag gcggagggtg gcgcggcgct cgagcaggag cccccgcgtg   8520
ccggcctccg cggcctcggc ggcggcggcc ggtctcaggc gggcagctgg gccaggggca   8580
cgggcgcgtt gagctcgggc agcgggaggt ggtcgcggcg cagacgcgag gcgtgggcga   8640
tgacgcggcg gttgatgttc tggatctgcg ggttcccgga gaagaccacg ggcccggtga   8700
ctcggaacct gaaagagagt tccacggaat caatgtcggc atcgtgggtg gccacctggc   8760
gcaggatctc ggacacgtcc ccgctgtttt cgcggtaggc gatgtcctgc atgaactgct   8820
cgagctcgtc ctcgtccagg tccccgtggc cggcgcgctc cacggtggcg gccaggtcga   8880
cggtgatgcg gttcatgatg gccaccaggg cgttctctcc gttctcgttc cacacgcgac   8940
tgtagaccag ctggccgtcg gcgtcccgcg cgcgcatgac tacctgggcc aggttgagcg   9000
ccaccaggcg gttgaagggc gcctgcaggc gcagggcgtg gtgcaggtag ttgagggtgg   9060
tggcgatgtg ctcgcagagg aagaagttta tgacccagcg gcgcagggtc agctcgttga   9120
tgtcgcccag gtcctcgagg cgctgcatga cccggtagaa ctcgggggcg aagcgaaaaa   9180
actcgtgctg gcgggccgag accgtgagct cctcttccag ggcggcgatg gcctcggcca   9240
ccgcctgccg cacctcctcc tctaaggagg gcgggggcgt gctgggtccg gccaccgccg   9300
cctcttcttc ctcttctccc tccaggggtg gcatctcctc gtcttcttct tctgctgctg   9360
ctgcctccgc ggggacgggg ggcgcaggcc ggggacggcg ccggcgcaag ggcagccggt   9420
ccacgaagcg ctcgatgacc tcgccccgca tgcggcgcat ggtctcggtg acggcgcggc   9480
cgccctcccg gggccgcagc tcgaaggcgc ccccgcgcag cgcggtgccg ctgcagaggg   9540
gcaggctgag cgcactgatg atgcagcgtg tcaactctct cgtaggtacc tcctgctgtt   9600
gcagcgcttc ggcaaactcg cgcacctgct cttcggaccc ggcgaagcgt tcgacgaagg   9660
cgtctagcca gcaacagtcg caaggtaagt tgagcgcggt gtgcgtcggg agccggaggt   9720
gccggctgac gaggaagtga aagtaggccg tcttgagctg ccggatggcg cgcaggaggg   9780
tgaggtcttt gcggccggcg cgctgcaggc ggatgcggtc ggccatgccc caggcctcct   9840
gctggcagcg gccgatgtcc ttgagctgct cctgcagcag atgtgccacg ggcacgtccc   9900
ggtcggcgtc caggtgggtg cgaccgtagc cccgcagggg gcgcagcagc gccaggtcgg   9960
ccaccacgcg ctcggccagg atggcctgct gcatgcgctg cagggagtct gagaagtcat  10020
ccaggtccag gaaccggtgg taggcgcccg tgttgatggt gtaggagcag ttgcccagca  10080
cggaccagtt gaccacctgg tagtggggct ggatgacctc ggtgtagcgc agtcgactgt  10140
aggcgcgcgt gtcaaagatg taatcgttgc agaggcgcag caggtgctgg tagcccacga  10200
gcaggtgggg cggagggtag aggtagaggg gccagtgttc cgtggccggt tggcgggggg  10260
agaggttcat gagcatgagg cggtggtagc ggtagatgaa gcgggacatc caggcgatgc  10320
cgacggcgga gacggaggcg cgggtccact ggtgggcgcg gttccaaatg ttgcgcaccg  10380
```

-continued

```
ggcggaagag ctccacggtg taaatggatt gccccgtgag gcgggcgcag tcgagggcgc  10440
tctgtcaaaa agaaccgggt gtggttggtt ggtgtgtggt agcgatctat ctttctttgt  10500
gatcttggta gtgaagcctg ccaggctcca gcagggggcg tccgccgtct ttccttcctt  10560
ccctatctgg aggtgtgtct ctgttctctt ttttatttca tgtagccatg catcccgttc  10620
tgcggcagat gaagccgccg gccggcgccc tgggcgcgga gggggcgacg cgctctcggt  10680
cgccctcgcc gtcgctgacg cggccgcgcg aggaggggga gggcctggcg cggctgtcgg  10740
gcgcggcggc ccccgagcgg cacccacggg tgcagctcaa gcgagaggcc atggaggcct  10800
atgtgccgag gcagaatgcg ttccgcgagc gaccggggga ggagggggag gagatgaggg  10860
acctgcggtt ccgcgcgggg cgggagatgc agctggaccg ggagcgagtg ctccagcccg  10920
aggactttga ggggcgcgtg gaggaggcgg ggggagtgag cgcggcgcgg gcccacatga  10980
gcgcggccag cctggcccag gcctacgagc agacggtacg cgaggaggtc aacttccaaa  11040
agaccttcaa caacaacgtg cgcaccctgg tgagccggga cgaggtgacc atgggactga  11100
tgcacctgtg ggactttgtg gaggccttcc tgcagcaccc ccggtcccgc gcgctgaccg  11160
cgcagctgct gctgatcgcg cagcactgcc gggacgaggg catggtgaag gaggcgctgc  11220
tgagcctggg cgcgcccgag agccgctggc tggtggacct ggtgaacctg ctccagacca  11280
ttgtggtgca ggagcggtcc atgagcctga gcgagaaggt ggcggccatc aactactcgg  11340
tggcgaccct ggccaagcac tacgcgcgca agatctccac cttctacatg cgcgcggtgg  11400
tgaagctgct ggtgctggcc gacaacctgg gcatgtaccg caacaagcgg ctggagcgcg  11460
tggtcagcac ctcgcggcgg cgcgagctca atgacaagga agctcatgtt tggcctccgc  11520
cgggcgctgg ccggggaggg cgaggaggac ctggaggagg aggaggacct ggaggaggcg  11580
gaggaggagg agctggaaag aggaggagtt cggtccccgg ggaccgcggc gcgtgaggtg  11640
gcagtccccg ctgactgcga gcgatgaggg tgatgtgtac tgatggcaac catccccctt  11700
tttaacaaca acagcagcat ggcggcgagc tctgaagctg ggcggcggc ggcgggggtg  11760
agcgcggcct ccctggcgcc cgagcgggcg acgcggatgc aggcgctgcc ctccctggac  11820
gagccttggg agcaggctct gcggcgcatc atggcgctga cggccgacgg gtctcggcgc  11880
ttcgcgagcc agcccctggc caaccgcatc ggggccatcc tggaggcggt ggtgcctccg  11940
cgcacgaacc cgacgcacga gaaggtgctg accgtggtga acgcgctgct ggagacctcg  12000
gccatccgcc cggacgaggc cggcatggtg tacgatgcgc tgctggagcg ggtctcccgc  12060
tacaacagcg gcaacgtgca gaccaacctg gaccggctgt cccaggacgt gcggcaggtg  12120
atcgcccagc gcgagcgctc gagcgccaac aacctgggca gcctggccgc gctgaatgcc  12180
ttcatcgcct cgctgcccgc aacggtggag cggggccagg agagctacct ggggttcctc  12240
agcgcgctgc ggctgctggt gagcgaggtg ccgcagacgg aggtgttccg ctcggggccg  12300
cacaccttcc tgcaggcggc gcggaacggt tccaagacgg tgaacctcaa ccaggccatg  12360
gagaacctgc ggcccctgtg gggctgcag gcccccgctg gggagcgcgg gcacgtgtcc  12420
tccctgctga cgcccaacac ccggctgctg ctgctcctgg tggctccctt cgcggaggag  12480
atgaacgtca gccggagctc ctacattggg cacctgctga cactctaccg cgagacgctg  12540
gccaacttgc atgtggacga gcgcacgtac caggagatca ccagcgtcag ccgggcgttg  12600
ggcgacgagg acgacgcggc gcggctgcag gccaccctca acttcttcct gaccaaccgg  12660
cagcggcggc tgccggcggc gtatgccctg accgccgagg aggagcgcat cctgcgctac  12720
```

-continued

```
gtgcagcagg ccgtgagcct gtacctgatg caggacgggg cgacggccac gggcgccctg  12780
gacgaggcca gccgcaacct ggagcccagc ttctacgcgg cgcaccggga cttcatcaac  12840
cgcctgatgg actacttcca tcgcgcggcc gcggtggcgc ccaactactt tatgaatgcc  12900
gtcctgaacc cccgctggct gccctcggag ggcttcttca ccggcgtgta tgacttcccg  12960
gagcaggacg agggggagga gcggccctgg gacgcctttg acagcgacga ggagggccgc  13020
ctcatgctgc ggtccgcagc ctcctcagag ccctcctcct ccttcacccc cctgcccctg  13080
accgaggagc cgccctcgcg gccctccacc ccggccctct cgcgcgtccc gtcccgggca  13140
tcctccctgc tctctctggc ctctctggga aagcgggagg gaggggactc gctcgcctac  13200
tcgccggcca cgcccaccta tggctctcgc tggggctcgc gccgctccag cctggccagc  13260
ggcgccgaca gcctggagtg ggacgcgctg ctggcccctc ccaaggatgt gaacgagcac  13320
ccaggcgccg ccgccggccg ccgccgccgc gcctcccgct cctccctgga ggaggacatc  13380
gacgccatca gcagccggct gttcacctgg cgcacgcgcg cccaggagat gggcctgccc  13440
gtggccagct tctcccgccg ccaccagccg cgccccgggg ccctcgaaga cgacgaggag  13500
gaggaagact ggcgccagga ccggttcttt cgcttcgaag cgcccgagga aaaccccttc  13560
cgccacatcg cccccaaggg gctgtaatgc aaaaaagcaa aataaaaaac ccctcccggt  13620
ccaactcacc acggccatgg ttgtccttgt gtgcccgtca gatgaggagg atgatgccag  13680
cagcgccgcc gcagggagcg tcgcctccgc cgtcctacga gagtgtggtg ggtcttcgc  13740
tcacggagcc tctttatgtg ccgccgcggt acctgggccc caccgagggg cggaacagca  13800
tccgttattc acagctcccg ccgctctacg ataccacaaa gatctatctg atcgataaca  13860
agtcggcgga tatcgccagt ctgaactacc aaaacaacca cagtgacttt ctcaccagcg  13920
tggtgcagaa cagcgacttc acgcccatgg aggcgagcac gcagaccatc aacctggatg  13980
agcgctcgcg ctggggcggg gagtttaaga gcattctgac caccaacatc cccaacgtga  14040
cccagtacat gttcagcaac agcttccggg tgcgcctgat gagcgcgcgc gataaagaga  14100
caaatgcccc cacctacgag tggttcaccc tgaccctgcc cgagggcaac ttctcggaca  14160
tcgcggtcat cgacctgatg aacaacgcga tcgtggagaa ctacctggcg gtggggcggc  14220
agcagggggt caaggaggag gacatcgggg tgaagatcga cacgcgcaac ttccgcctgg  14280
gctatgaccc ggagaccaag ctggtcatgc ccggcagcta caccaacatg gcctttcacc  14340
ccgacgtggt gctggcaccg ggctgcgcca tcgacttcac cttctcccgc ctaaacaacc  14400
tgctgggcat ccgcaagcgc taccccctacc aggagggctt catgctgacc tacgaggacc  14460
tggcgggggg caacatcccc gcgctgctgg acctcaccac ctatgatcag gagaactcca  14520
gcaccatcaa gcccctgaag caggacagca agggtcgcag ctaccacgtg ggcgaggacc  14580
ccgaggcggg ggacaccttc acctactacc gcagctggta cctggcctac aactacgggg  14640
acccggccac gggcaccgcc tcccagacgc tgctggtctc ccggacgta acctgcggag  14700
tggagcaggt ctactggagc ctgccggacc tgatgcagga cccggtgacc ttccggccca  14760
gccagacgcc gagcaactac ccggtggtag ccacggagct actgccgctg cgctcccggg  14820
ccttctacaa cacccaggcc gtgtactccc agctcctgca gcaggccacc aacaacaccc  14880
tggtctttaa ccgcttcccg gagaaccaga tcctcctgcg cccgccagag tccaccatca  14940
cctccatcag cgagaacgtg ccctcgctga cggaccacgg cacgctgccg ctgcgtaaca  15000
gcatccccgg ggtgcagcgg gtaaccgtca ccgacgcgcg gcgccgcgtg tgtccctatg  15060
tgtacaagag tctcggggtg gtgaccccga gggtgctcag cagccgaacc ttctaaccga  15120
```

-continued

```
cagccctacc cgtcacaggg gagacagaga aaagacagcc agccccgcca tggccatcct  15180
cgtctcgccc agcaacaact ttggctgggg actgggcctg cgctccatgt acgggggcgc  15240
ccgccgcctg tccccggatc accccgtgat cgtccgacgc cactaccggg ccaactgggc  15300
cagtctgaag ggacgcgtgg cccccagcac catagcgaca acggatgacc ctgtggccga  15360
cgtggtcaac gcgatcgccg gcgccacccg ccgccggcgc cgccatcgtc gacgtcggag  15420
ggccgcgcgc gtctcctccg tggccgtcac cggggacccg gtggccgatg tggtcaacgc  15480
ggtggaggcg gtagcccggc gccgccgcgc gcggcgccgt tcttcgcgca tgcagaccac  15540
gggggacccc gtggcggatg tggtggcggc ggtggaagcg gtggcgcgcc ggaggcggag  15600
cacccggcgg cggcgcaggc gctccgcgcc ggccatcctg gggtgcgcc gcagccgccg  15660
cctccgcaaa cgcacctcgt cctgagattt ttgtgttttg ttttttctgc ctcccgtggg  15720
tgaacaagtc catccatcca tccaacatcc gtggctgctg tgtctttgtc ttttctttgc  15780
gttgcgcccc agttgagccg gcaccgacgc gctcggccat ggccatctcg cgccgcgtga  15840
aaaaggagct gctgcaggcg ttggcgcccg aggtgtacgg ggcgcctaag aaggaggaga  15900
aggacgtcaa agaggagtcc aaagctgacc ttaaaccgct gaagaagcgg cgcaaggcca  15960
agcgggggtt gagcgacagc gacgaggtgc tggtgctggg cacgcgcccc aggcgccgct  16020
ggacggggcg gcgcgtgcgc gcccacctac cgcccggtgc cagcctcgcc tacgtcccgg  16080
gtcttcggag gtcgagcgcc accaagcgct ctgcggacga gttgtatgcg gacacggaca  16140
tcctgcagca ggcgtcccag cgcctgaacg aatttgctta tggcaagaga gcccggcggc  16200
agcggcgggc ccgcccctcg ccgacccccg cgtcccgcgg ccggaccacc aagcgctctt  16260
atgacgaggt cgtggcagac agtgacatcc tgcagcaact tggatccggg gaccgctcca  16320
atgagttctc ctatggcaag cggtcgctgc tgggggagtc aggagacacc gtcccggctg  16380
tggccgtccc gctggaggaa ggcaggaacc acacacccag cctgcagccg ctcaccgagc  16440
ccatgcccct ggtgtcccct cgcacggccg tcaagcgccg ggcgcccgcc gacgagccca  16500
ccgcctcact ggtccccacc gtgcaggtcc tggcccccaa gcgtcgtctg caggaggtgg  16560
tggtggagcc gcccgctcca gcacccacgc cgcccctagc cccgcggcgg tccagccggc  16620
gcatcattct ggctccgcgc cgggcgggcc ggccccaggc cgtcgtggcg ccgcagctca  16680
gcgcggccgc ggcgctggag cgggcggcgg ccgccgtgcc cctgccaccg gacacggagg  16740
acgacctggt ggagatggca gaggctgtcg ccgcgcccga ggtgctgccc agcctccccg  16800
tctccatcat gccgcccacc gccacggagg tggccctgcc cgtacagacc ccactgccgc  16860
ccgtggcggt ggccaagagc tccctgaccc ccggcctccg cgcgctgatg ggcaccgagc  16920
gggtgccggt tccagtcctg gaggcgcccc tggtggccat gcccgtgctc cgggccacca  16980
ccgcccgtgc cgagcccccg cgccgcgtgc cccgcagggc cgtgcgggac atcccggcca  17040
ggcagccccg cacggtatcc ctgcccgtgc tcacggagcc cggcccggcc accgcggtcg  17100
cctccgtgcg cgcggcagcc caagtcctgc aggcgccccc cgcccgaccg gccaccgtct  17160
ccgtgggggt gggcaccgag ccggtggtgc agtccatcac ggtcaagcgg tcaaagcgcc  17220
tgaccaagca ccatcggggt gcagaccatc gacgtcaccg tgcccaccgt ccgcactgtc  17280
agcgtgggca ccaacacgcc ccggctgagg agcgcctcgg tgggcgtcca gaccgctccc  17340
gagacccgct cccagggggt gcaggtggct ttccaaccag cgtgctagcc caccgcacac  17400
ccaggcaggt gcggctgacg gcggtggtgc cccccacccc gcgcgccccg gtggttccgg  17460
```

-continued

```
tggcccggcg cccgcggcgg ttccggtgcc tcccccagcc cctccagccc cgcgcgcgcc  17520
gcgtgcgcct cgcgccccca gagcgcctcg gcgtcgccgc cgtaccccgg tggcggtggc  17580
agcgccgccc gcccgcagcg gcggtccccc gccctcggct gccgaggcgg cccatcgtgc  17640
tgcccggggt gcgctatcat cccagtcagg ccatggctcc caccgcccaa cgcgtcatct  17700
ggcgttgatt tatttttgga gacctgactg tgttgtgttc cttaaatttt ttatcctcct  17760
cctcctctgc tgaagccaga cgatgctgac ctaccggttg cggctgcccg tgcggatgcg  17820
gagaccgaga ctccgcggtg ggttccgcgt ggcgcctcgg cgcagcggcg gcaggcggcg  17880
gtaccgccgg gggccgatga ggggtggcat cctgccggcg ctggtgccca tcatcgcggc  17940
atccatctgg gccatccccg gcatcgcctc ggtggcgatg agtgctagac aacgcaatta  18000
acggcgctgc tgtgtatgtg tgtcttccat gtgccttcct tccttcgttc ccaacggaac  18060
agcagcaccg tctccatgga ggacctaagc ttttccgcgt tggctccacg ctttggcacg  18120
cggccggtca tgggcacttg gagcgaaatc ggcacgagtc agatgaacgg cggcgcgctc  18180
agctggagca atatctggag cgggctgaag agctttggta gttctctggc ctccacggcc  18240
aacaaggcct ggaacagcgg gacggtgacg agcgtgcgca acaagttgaa ggatgccgac  18300
gtgcagggga agataggtga ggtcattgcc tccggggtcc acggtgccct ggacgtggcc  18360
aaccaggccg tctcccacgc cgtggaccgc cggtgcaaca gcagcagctg cggcagcagc  18420
agctcctccg ccagcagcag caacagatgg gcctcgtgga accctcctat gagatggaga  18480
cagacgagct gcctcctccc cccgaggacc tcttgcctcc tcctcctcct ccgccgcctg  18540
cctcggccac tcccgcgcgc caatcccgcg ggacgtcccg ccaagcgccc gccgccgccc  18600
aggagatcat catccgctcc gacgagcccc ctccctatga agagctgtat cccgacaagg  18660
ccgggatccc cgccaccttg gagctgcgtc ccgagaccaa actgcccgcc gtggcccaca  18720
ataagatgcg ccccccgccg ccgctcacca ccaccacctc ctccgctgcc gccgccgccc  18780
ccgccccggc ccccgcggct cctgtgcgtc ggcgtccggc cgcggctccg gccgcggctc  18840
cggcgagttc caaaggcccc ccaggtgggg gtccgcgcgc gcgggtggca aaacaaactc  18900
aacaccattg tgggactggg tgtccgcaca tgcaagcgcc gtcgttgtta ctgagagaga  18960
cagcatggag aaacaacaat gtctggattc aaataaagac acgcctattc ttccacggtg  19020
ctccgcgctg tgttattttc aacgggctgt ttccttttgc atctctgtgc catcgcgcca  19080
cggggaattc cgcaggatgg cgacgccgtc gatgatgccg cagtggtcct atatgcacat  19140
ctccgggcag gacgcgtccg agtacctgtc tcccgggctg gtgcagttct cccaggcgac  19200
ggagacctac tttaacctga acaacaagtt taggaacccc accgtcgcgc ccacccacga  19260
tgtgacgacg gagcgctcgc agcggctgca gctgcgcttc gtccccgtgg acaaggagga  19320
cactcagtac acatacaaga cccgcttcca gctggcggtg ggcgacaacc gcgtgttgga  19380
catggcgagc accttctttg acatccgggg aacgctggac cggggaccct ccttcaaacc  19440
gtactcgggc accgcgtaca acatcatggc tcccaagagc gctcccaaca actgtcaata  19500
tctagaccct aaaggtgaaa ctgaggctgg caaagttaat accattgctc aagcaagttt  19560
tgtgggtcct attgatgaaa ccacgggaga cattaaaatt acagaagaag aagacgaaga  19620
gaccaccatc gatcctttgt atgagcccca accccagctt ggtccaagct cgtggtcaga  19680
caatatacct tctgcgacta gcggagctgg aagagttctc aaacagacca caccgcgtca  19740
accttgttac ggttcttatg cctctccgac aaatattcac ggtgggcaaa cgaaggatga  19800
caaggttaca ccattgtact ttacaaacaa tcccgccacc gaagccgaag cactcgaaga  19860
```

-continued

```
aaatggatta aagccaaatg tcaccctata ctcagaggat gttgacctaa aagcaccaga  19920
tactcatctg gtctatgctg tgaatcaaac ccaggaattc gctcaatatg gacttggaca  19980
acaggccgct ccaaacaggg ccaattacat cggcttcagg gacaacttta tcgggctgtt  20040
gtactacaac agcaatggca accagggcat gctagccggt caggcctctc agctcaacgc  20100
ggtggtcgac ctgcaggaca ggaatcaccg aactagctac cagctcttcc tcgatagcct  20160
ctatgacagg tcgaggtact ttagcctgtg gaaccaggcc atcgattctt atgacaagga  20220
tgtgcgtgtg ctggaaaaca atggcgtgga ggacgagatg cccaactttt gctttcccat  20280
cggcgccatc gagaccaaca tgacatttac acagctcaaa aagagtgaga atggtggctc  20340
aagagccaca acctggacaa aggagaatgg ggatgatggc ggaaacggag cggagcacta  20400
cctgggcatc ggcaacctca acgccatgga gatcaatctc acggccaacc tctggcgcag  20460
cttcctctac agcaacgtgg cgctgtacct gcctgacaag tacaagtttt ccccgcccaa  20520
cgtccccatc gaccccaaca cgcactccta tgactacatc aacaagcgcc tgcccctcaa  20580
caacctcatt gatacctttg tcaacatcgg ggcgcgctgg tccccggatg tcatggacaa  20640
cgtcaacccc ttcaaccacc accgcaacta cggcctgcgc taccgctccc agctcctggg  20700
caacggccgc tactgcaagt tccacatcca ggtgccgcaa aagttctttg ccctcaagag  20760
cctgctgctc ctgccggggg cgacctacac ctacgagtgg tccttccgca aggacgtcaa  20820
catgatcctc cagtccacgc tgggcaacga cctccgcgcg gacggggcca aaatcaacat  20880
cgagagcgtc aacctctacg ccagcttctt tcccatggcc cacaacaccg cctccaccct  20940
ggaggccatg ctgcgcaacg acaccaacaa ccaaaccttt attgacttcc tctcctccgc  21000
caacatgctc taccccatcc cggccaacgt caccaacctg cccatctcca ttcccagccg  21060
caactgggcc gccttccgcg gctggagctt cacgcggctg aagcacaacg agacccccgc  21120
cctgggctcg cccttcgacc cctactttac ctactcgggc tccatcccct acctggacgg  21180
gaccttctac ctgggccaca ccttccgccg catcagcatc cagttcgact cctccgtggc  21240
ctggccgggc aatgaccgcc tgctcactcc caacgagttc gaggtcaagc gcaccgtgga  21300
cggggagggc tacacggtgg cccagaccaa catgaccaaa gactggttcc tggtgcagat  21360
gctcgcccac tacaacatcg gctaccaggg ataccacctg ccagagggct accgcgaccg  21420
cacctactcc ttcctgcgca actttgagcc catgtgccgc caggtgcccg actacgccaa  21480
ccacaaagat gagtacctgg aggtgcccac caccaaccag ttcaacagca gcggctttgt  21540
atccgcggcc ttcaccgccg gcatgcgcga ggggcaccca taccccgcca actggcccta  21600
cccgctcatc ggcgaagacg ccgtgcagac cgtgacccag cgcaagttcc tctgcgaccg  21660
cacgctctgg cgcatcccct tctcctccaa cttcatgtcc atgggcaccc tcaccgacct  21720
gggccagaac ctcctctacg ccaactcggc ccacgccctc gacatgacct tcgaggtcga  21780
cgccatggat gaacccaccc tcttgtatgt tctgttcgag gtctttgacg tctgcggcgt  21840
gcaccagccg caccgaggcg tcatcgaggc cgtctacctg cgcacgccct tctccgccgg  21900
gaacgccacc acctaaggcg gagccgcgca ggcatgggca gcaccgagga cgagctccga  21960
gccatggcgc gcgacctcca gctgccccgc ttcctgggca cctttgacaa gtccttcccg  22020
ggcttcttgc aagagtccca gcgctgctgc gccatcgtca acacggccgc ccgccacacc  22080
ggaggccgcc actggctggc cgtcgcctgg gagcccgcct cgcgcacctt ctacttcttt  22140
gaccccttcg gcttctccga ccgggagctc gcccaggtct atgactttga gtaccagcgc  22200
```

-continued

```
ctgctgcgca agagcgccat ccagagcacc ccggaccgct gcctcacgct cgtcaagagc  22260
acccagagcg tgcagggacc gcacagcgcc gcctgcggac tcttctgcct cctcttcctc  22320
gccgcctttg cccgctaccc cgacagcccc atggcctaca atcccgtcat ggacctggtg  22380
gagggcgtgg acaacgagcg gctcttcgac gccgacgtcc agcccatctt ccgcgccaac  22440
caggaggcct gctacgcgtt cctcgctcgc cactccgcct acttccgcgc ccaccgccac  22500
gccatcatgg aacagacaca cctgcacaaa gcgctcgata tgcaataaag gctttttatt  22560
gtaagtcaaa aaggcctctt ttatcctccg tcgcctgggg gtgtatgtag atggggggac  22620
taggtgaacc cggacccgcc gtcggctccc ctccatcccc tcttctctca aaacaggctc  22680
tcatcgtcgt cctccgttcc cacggggaag atggtgttct gcacctggaa ctggggcccc  22740
cacttgaact cgggcaccgt cagtggaggc cgcgtctgca tcagggcggc ccacatctgt  22800
ttggtcagct gcagggccag catcacatcg gggcgctga tcttgaaatc acaattcttc  22860
tgggggttgc cgcgcgaccc gcggtacacc gggttgtagc actggaacac cagcaccgcg  22920
gggtgggtca cgctggccag aatcttgggg tcttccacca gctgggggtt cagcgccgcc  22980
gacccgctca gcgcgaaggg ggtgatcttg caggtctgcc ggcccagcag gggcacctgg  23040
cggcagcccc agccgcagtc gcacaccagc ggcatcagca ggtgcgtctc cgcgttgccc  23100
atccgggggt agcaggcctt ctggaaagcc ttgagctgct cgaaggcctg ctgcgccttg  23160
gagccctccg agtagaagag gccgcaggac cgcgccgaga aggtgttggg ggccgacccc  23220
acgtcgtggc tgcaacacat ggccccgtcg ttgcgcagct gcaccacgtt gcggccccag  23280
cggttggtgg tgatcttggc gcgctcgggg gtctcgcgca gggcgcgctg cccgttctcg  23340
ctgttgagat ccatctccac cagctgctcc ttgttgatca tgggcagccc gtgcaggcag  23400
tgcagcccct ccgagccgct gcggtgctgc cagatcacgc acccgcaggg gttccactcg  23460
ggcgtcttca gacccgccgc cttcaccaca aagtccagca ggaagcgggc catcactgtc  23520
agcaggctct tttgcgtgct gaaggtcagc tggcagctga tcttgcgctc gttcagccag  23580
gcttgggccc cgcgccggaa gcactccagg gtgctgccgt ccggcagcag cgtcaggccc  23640
ttgacatcca ccttcagggg gaccagcatc tgcacagcca gatccatggc ccgctgccac  23700
ttctgctcct gagcatccag ctgcagcagc ggccgggcca ccgccgggct cggggtcacc  23760
gggcgcgggg ggcgggcccc ctcctcttcc tccccatctt cgcccttcct cctcgcgggc  23820
cgcgccgtcg ccgctgccgt ctcttcagcc tcgtcctcct cctcctcgct gaccaggggc  23880
ttggcacgcg cgcgcttccg ccgctcctgc acgggcggag aggccgcgcg cttgcggcct  23940
cccccgcgcc ggctggggt cgcgacagga gcgtcgtcca caatcagcac cccctcttcc  24000
ccgctgtcat agtcagacac gtccgaatag cggcgactca ttttgcttcc cctagatgga  24060
agaccagcac agcgcagcca gtgagctggg gtcctccgcg gccccgaccc ttccgccgcc  24120
accaccgccg ccacctccgc ccacgtcacc gccaccttca ctgcagcagc ggcagcagga  24180
gcccaccgaa accgatgacg cggaggacac ctgctcctcg tcctcctcgt cctccgcctc  24240
cagcgagtgc ttcgtctcgc cgctggaaga cacgagctcc gaggactcgg cggacacggt  24300
gctcccctcc gagccccgcc gggacgagga ggagcaggag gaggactcgc ccgaccgcta  24360
catggacgcg gacgtgctgc agcgccacct gctgcgccag agtaccatcc tgcgccaggt  24420
cctgcaggag gccgcccccg gcgcagccgc ggaggccgcc gaggcgccct cggtggcgga  24480
gctcagccgc cgcctggaag cggccctctt ctcccccgcc acgccgccgc ggcgccagga  24540
gaacggaacc tgcgccccgg acccccgcct caacttctac ccggtcttca tgctgcccga  24600
```

-continued

```
ggccctggcc acctacctcc tcttcttcca caaccaaaag atccccgtca gctgccgcgc  24660
caaccgccca cgagccgacg cgcactggcg gctgcccagt gggacccccct tacctgacta  24720
tccaaccacc gacgaggttt acaagatctt tgagggcctg ggggacgagg agccggcctg  24780
cgccaaccag gacctgaaag agcgcgacag cgtgttagtc gagctcaagc tggacaaccc  24840
ccgcctggcg gtggtcaagc agtgcatcgc cgtcacccac ttcgcctacc cggccctggc  24900
gctgccaccc aaggtcatga gcacgctcat gcagaccctg ctggtgcgcc gcgcgagccc  24960
actccccgac gagggcgaga cgcccctcga ggacctcctg gtggtcagcg acgagcagct  25020
ggcccgctgg atgcacacct cggaccccaa ggtcctggag gagcggcgca agaccgtcac  25080
cgccgcctgc atggtcacgg tgcagctcca ctgcatgcac accttcctca cctcccgcga  25140
gatggtgcgc cgcctcggag agtgcctcca ctacatgttc cgccagggct acgtcaagct  25200
agctagcaag atcgccaata tggaactctc taacctggtc tcctacttgg gcatgctgca  25260
cgaaaacagg ctcggtcagc acgtgctcca ccacaccctc aagcatgagg cgagacgcga  25320
ctacgtccgg gacaccattt acctatacct ggtctatacc tggcagaccg ccatgggggt  25380
ctggcagcag tgcctcgagg accgaaacct gcgcgccctg gaaacgtctc tggctcgcgc  25440
tcgccagagc ctgtggacgg gctttgatga gcgcactatc gcgcaggacc tcgccgcgtt  25500
ccttttcccc accaagctcg tagagaccct gcagcgctcg ctccccgact ttgccagcca  25560
gagcatgatg catgccttcc gctccttcgt cctcgagcgc tccggcatcc tgcccgccgt  25620
ctgcaacgcg ctcccctctg actttgtgcc caccgtctac cgcgagtgcc cgccgcccct  25680
ctgggctcac tgctacctcc tgcgcctcgc caacttcctc atgtaccact gcgacctcgc  25740
cgaggacacc tccggcgagg gcctctttga gtgctactgc cgctgcaacc tctgcgcacc  25800
gcaccgctgc ctcgccacca acaccgccct cctcaacgag gtgcaagcca tcaacacctt  25860
tgagctccag cggcccccca agcccgacgg caccctgcca ccgcccttca agctgacccc  25920
cggtctctgg acctccgcct tcctccgcca ctttgtctcc gaggactacc actcggaccg  25980
catcctcttc tacgaggacg tgtcccgccc ccccagggtg gagccctccg cctgcgtcat  26040
cacgcactcg gccattctcg cgcaattgca tgacatcaaa aaggccaggg aagagttttt  26100
gctgaccaaa ggccacggcg tctacctaga cccccacacc ggagaggagc tcaacaccgc  26160
cgccccgtcc accgcccacc atgccgcccc tccggaggaa gcccatccgc agcagcacca  26220
gcaccagcag cagccgagcc accgccgccg ccaccaccgc tccagctacg cagaccgtgt  26280
ccgaagcgag ctccacgcct acggcggtgc gaccggttcc tcccgcgacc ctgtctctgg  26340
cggatgctct gccagaggaa cccactcccg cgatgctgct cgaagaagag gctctcagca  26400
gcgagaccag cggcagctcc gaaggcagtt tgctcagtac cctcgaggaa ctggaggagg  26460
aggaggaacc ggtcacaccg acgaggccat ccaagccctc ctacaccaac agcagcagca  26520
gcaagagcat cagccagcgc aggaactccg tcgtccccag cgaggctcgt agatggaatc  26580
agacatccat ccaccggagt agccagccag gtaggacacc tccgccctcg gcccgccgac  26640
gctcctggcg ccgctaccgc cacgacatcc tctcggccct ggagtactgc gccggagacg  26700
gagcctgcgt gcgccggtac ctactctacc accacaacat caacatccct tccaagatca  26760
tccgttacta caaatcctct tcccgttcca gcgatctcca ggaaggccgc agcagcggcg  26820
gcagcagaac cagcccacgt cagccagctg agagctaaga tcttccccac gctgtacgcc  26880
atcttccagc agagccgcgg cggccaggac gccctcaaaa tcaggaaccg caccctgcgc  26940
```

-continued

```
tccctcacca agagctgtct gtatcaccgc gaggaggcca agctggaacg cacgctctcg  27000
gacgcagaag ctctcttcga gaagtactgc gctcggcagc ggcagacccg ccggtattta  27060
aggagcggac cctgcgtgcg gacacaccat gagcaaacaa atccccaccc cgtacatgtg  27120
gtcttatcag ccacaatctg ggcgtgccgc cggtgcctcc gtcgattact ccacccgcat  27180
gaattggctc agtgccgggc cttccatgat tggccaggtc aatgacatcc gacacaccag  27240
gaaccagatt ctcattcgcc aggcccttat caccgagacg ccacgccccg tccaaaatcc  27300
cccgtcctgg cccgccagcc tgttgcctca gatgacgcaa ccgcccaccc acctgcacct  27360
gccgcgtaac gaaattttgg aaggcagact gactgacgcc ggcatgcaat tagccggggg  27420
cggagccctc gcacccagag acttatatgc cctgaccctc cgcggcagag gcatccagct  27480
caacgaggac ctacccctct cggcgagcac tctccggccg gacggcatct tccagctcgg  27540
aggcggaggc cgctcctcct tcaaccccac cgacgcctac ctgacgctgc agaactccag  27600
ctcccttccc cgcagcggcg gcatcggcag cgagcaattt gtccgcgagt tcgtgcccac  27660
ggtctacatc aaccccttct ccggaccgcc cgggacctac cccgaccagt tcatcgccaa  27720
ctacaacatc ctaacggact ctgtagcagg ctatgactga cggtccccag ggtcagcagc  27780
ggctgcggga gctcctcgac cagcaccgcc gccagtgccc taaccgctgc tgcttcgcca  27840
gggaagggat tcacccggag tacttttgca tcacccgcga gcactttgag gccgagtgca  27900
tccccgactc tctgcaagaa ggccacggtc tgcgcttcag cctccccacg cgctacagcg  27960
accgccgcca ccgcgatgga gaccgcacca tcctcacttc gtactactgc ggccctgctt  28020
ctttcaaagt tcgctgtctc tgcggccatc ctgctcctca ccctcttctt ctcgaccttc  28080
tgtgtgagct gtacaaccgc tcgtagcgtc agcccctaca cctcccctcg cgtccaattt  28140
ctgtccgaca tagaaccaga ctctgactct tactcgggct ctggctctgg ggacgatgaa  28200
gattatgaat atgagctggc taccaacaca ccgaacgaag acattctagg cagcatagtc  28260
atcaacaacc agatcgggcc caagaccctg gccctgggat acttttatgc cgccatgcag  28320
tttgtcttct ttgccatcat catcatcgtc ctcatcctct actaccgccg ctacgtgctg  28380
gccaccgccc tcatcgtgca gcgccagatg tggtcctccg aggccgtcct gcggaaaacc  28440
ttctcggcca ccgttgtggt tactccccca aaacaagtca ccccctgcaa ctgctcctgc  28500
cgcttcgagg agatggtgtt ctactacacc acctccgtct tcatgccctg gtgggcctca  28560
tcctcctgct caccgccatg gtccgcctgg ccaactggat agtggatcag atgcccagca  28620
ggaaccgcgc cccgccgctg ccaccgcccc tcacctatgt gggaccctgc gccgaggacc  28680
acatctacga tgagccaacc gtagggcaat acgtacagat gaagtagctc cccctctttc  28740
ccattccccc atttttctct attcaataaa gttgcttacc tgagttcatc cacactcggt  28800
ctgccagtgc agtctatcca tgcgccgttt tccatactca catagcgcag ccgcgcacgc  28860
ctcgccaggt gacgaaactg tcgaaatgta acatttcgcg cttctgtcag cagcaccccg  28920
ttatagacca gttccaccat gggaccgaag aagcagaagc gcgagctacc cgaggacttc  28980
gatccagtct accccctatga cgtcccgcag ctgcagatca atccaccctt cgtcagcggg  29040
gacggattca accaatccgt ggacggggtg ctgtccctgc acatcgcacc gcccctcgtt  29100
tttgacaaca ccagggccct caccctggcc ttcgggggag gtctacagct ctcgggcaag  29160
cagctcgtcg ttgccaccga gggctcgggg ctaaccacca acccggatgg caagctggtt  29220
ctcaaagtca agtcccccat caccctgacc gccgagggca tctccctgtc cctgggtccc  29280
ggtctttcta actcagagac cggcctcagt ctgcaagtca cagctcccct gcagttccag  29340
```

-continued

```
ggcaacgccc tcactcttcc cctcgccgcc ggtctccaaa acaccgatgg tggaatgggt  29400
gtcaaactgg ggagcggtct caccacggac aacagtcagg cggtgaccgt tcaggtggga  29460
aatggacttc agctgaacgg cgaaggacaa ctcaccgtcc ccgccacggc ccctttagtc  29520
tcagggagcg caggcatctc tttcaactac tccagcaatg acttcgtctt agacaatgac  29580
agtctcagtt tgaggccaaa ggccatctct gtcacccctc cgctgcagtc cacagaggac  29640
acaatctccc tgaattattc taacgacttt tctgtggaca atggcgccct caccttggct  29700
ccaactttca aaccctacac gctgtggact ggcgcctcac ccacagcaaa tgtcattcta  29760
acaaacacca ccactcccaa cggcaccttt ttcctatgcc tgacacgtgt gggtgggtta  29820
gttttgggtt cctttgccct gaaatcatcc atcgacctta ctagtatgac caaaaaggtc  29880
aattttattt ttgatggggc aggtcggctt cagtcagact ccacttataa agggagattt  29940
ggatttagat ccaacgacag cgtaattgaa cccacagccg caggactcag tccagcctgg  30000
ttaatgccaa gcacctttat ttatccacgc aacacctccg gttcttccct aacatcattt  30060
gtatacatta atcagacata tgtgcatgtg gacatcaagg taaacacact ctctacaaac  30120
ggatatagcc tagaatttaa ctttcaaaac atgagcttct ccgccccctt ctccacctcc  30180
tacgggacct tctgctacgt gccccgaagg acaactcacc gtccccgcca cggccccttt  30240
agtctcaggg agcgcaggca tctctttcaa ctactccagc aatgacttcg tcttagacaa  30300
tgacagtctc agtttgaggc caaaggccat ctctgtcacc cctccgctgc agtccacaga  30360
ggacacaatc tccctgaatt attctaacga cttttctgtg gacaatggcg ccctcacctt  30420
ggctccaact ttcaaaccct acacgctgtg gactggcgcc tcacccacag caaatgtcat  30480
tctaacaaac accaccactc ccaacggcac ctttttccta tgcctgacac gtgtgggtgg  30540
gttagttttg ggttcctttg ccctgaaatc atccatcgac cttactagta tgaccaaaaa  30600
ggtcaatttt atttttgatg gggcaggtcg gcttcagtca gactccactt ataaagggag  30660
atttggattt agatccaacg acagcgtaat tgaacccaca gccgcaggac tcagtccagc  30720
ctggttaatg ccaagcacct ttatttatcc acgcaacacc tccggttctt ccctaacatc  30780
atttgtatac attaatcaga catatgtgca tgtggacatc aaggtaaaca cactctctac  30840
aaacggatat agcctagaat ttaactttca aaacatgagc ttctccgccc ccttctccac  30900
ctcctacggg accttctgct acgtgcccca gagtgcctag agaaccctgg ccgtcagccg  30960
gcctccccct tcccaggcca cccggtacac cacccgctcc atgtttctgt atgtgttctc  31020
ctcccgccgc ttgtgcagca ccacctcccg ctgctcgagc tgaggatccg tgatggacac  31080
aaagccagga agacacatcc tcagctccgt gggggcgtcc aacaactgtt tatgtaaagg  31140
aaaataaaga ctcagagaaa atccaagttc atatgatttt tcttttattg attgggggaa  31200
ttgattcagg tggggtgtgc ataatcacaa aaatcacatc agcaggtaca cacctgagac  31260
atcagacagg ggtaaggaca gcgcctcagc ttctggaaca gacatcagaa atatttaatc  31320
tgctggtagc taacactcct tcccaacacc atacactcct ggagggccct ctgcctctcc  31380
tcctcccgct ccgcgtccct ctgccgggac caccactccc cctccgtgaa ctgctgcttc  31440
ctcccccgcc gctgcgcccc gatggcctcc gccgccagct tcagccagtg ccgcaagcgc  31500
tgggcgcagc gccgagccac cggctcgctc agctcgtggc agcgccggca caccagcact  31560
atgtaattgg catagtcccc gtcacagtag atgacctccc cccagtggaa catgcgcaac  31620
agcttcagat cacagtcata catgatcttt atgtacatca ggtgggcgcc tcgaaacatc  31680
```

-continued

```
acactgccca cgtacatcac gcgactcacg ctgggcaggt tcaccgcctc cctgaaccac  31740
cagaagatgc gattgtactc gcagccccgg atgatctcgc gcatcaggga gcgcatcacc  31800
acctgccccg cgcggcactc cagactggac cttttcagac agtggcaatg aaagttccac  31860
agcgtcgcgc ccgcacagcg tctccgggct gaaacatatc tgctccagct ccaaccccc   31920
acacaggctg tactgcagga aaatccattc ttgatgggaa aggatgtagc gccaggggac  31980
cacaatctcc aaacagggaa caaaacatac cgcggcccgg ctgttgcgca cggcccccac  32040
cggatgcaac gtgctcacgg agcagatacg ggtgggacag cggcccacgt ctcatagcaa  32100
gtcaagtccg gaagtggcac ggggttcgcc accactgcta ctgctgccgc tgcgccacca  32160
gctccatcgg ctcctccatc ctcctcctgt tccatcggct gaggtgctgc ctcctcctcc  32220
tcctgccgct gctccatcat gctcgtctgc ggtcatcagg agtcaaaaaa ttcattggcc  32280
accgcacgca gagagaacat ggagcgcagg ggcccaggtg cccggcccgt gcgctcgctc  32340
aactccccca gcaggtactc atagagatgc tcctccaaat ccaccgcaaa ccaggcatgc  32400
agaaactctt ccgttcgagg accgcccacg gtaaagacat agccctcccg caccttcacc  32460
gctgccagct gcacgcgctc atgtcgctgg gagtacaccc ggacccgggc ctggatgtac  32520
tccagcacct gatcgctcag acacctcaca gagatgccag cctgagccag cttctcatag  32580
agaggtggct gaatcttgag cttgaagcag cgagcggcta ggcactcccc gccccccttgg 32640
aacagggcgg ccgggtcagc catggacttc ctctacatcc ggggtcctgg ccacctcaca  32700
aactatctgg ccaatcgcct gaccacgggt caccaggtaa ggatgatgtc cgttgttgcg  32760
aatgagaatg ctcagaggtg actcggtagc gttatcaatc acgtccccaa aggtccaaag  32820
gtcccagtta gaagtcaggt gcttcagacc gcagacacgc ccatagcaac cagtgggaaa  32880
agccagcaag agatccgtgg gcacatgcac cgaagctccc gcaggaatct ccacccactc  32940
cgaggcgtag accgtgtaag ctacacaccc cgcctcccga gtgggagcag aagcattctc  33000
gctcagccga aagaacttca gggtggcctg catatcctct tttactcact tgttagcagc  33060
tccacacaga ccagggttgt gttggcggga ataggcagca ggggtacgtc cccagtgagg  33120
gacacctgga tggggggcag aggattgatg ccaggaagca gcaggtactg ggaaacagag  33180
accagatccc tcctctgaaa aatctcgctc agtcggacaa acacagcaaa cccagtgggc  33240
acgtagacta gcacattaaa aaggatcacg ctgggctgtt ctgacgtcag caccagatgt  33300
cgggacgtgc gcagatgaat gcggttctga tgaattaccg gaggcctctc acccgcagcc  33360
aacagcagac cgggctgctg atgcggtccc gcagacatat atgagttcaa tgtgtgtctt  33420
ttttctaaac gtctagtgag tgtgctcgtc ctgctcctgc caatcaaaat ccgggcacca  33480
gggctggtgg ttggacccga tgaagaagcg aggagaggcg gcctcctgag tgtgaagagt  33540
gtcccgatcc tgccacgcga ggtaggcgaa gtacagatag agcacggcga gaacagtcag  33600
caccgcggcc agcagcagtc ggtcgtgggc catgagaggg ggctgatggg aagatggccg  33660
gtgactcctc tcgccccgct ttcggtttct cctcgtctcg ctctcagtgt ctctctctgt  33720
gtcagcgccg agacgagtgt gagcgaacac cgcgagcggg ccggtgatat acccacagcg  33780
gatgtggcca cgcctgcggt cggttaatca gtaccccatc gtccgatcgg aattccccccg 33840
cctccgcgtt aacgattaac ccgcccagaa gtcccgggaa ttcccgccag ccggctccgc  33900
cgcgacctgc gactttgacc ccgcccctcg gactttgacc gttcccacgc cacgtcattt  33960
tcccacgcga cgtcacgttc ccacgctacg tcacacccct ctccaccaat caccgcccgc  34020
cgcccccaac cctctccgcc aatcaccacg ccacaaaagg ggcaataaaa gtgtgcggta  34080
```

```
tattattgat gatg                                                    34094


<210> SEQ ID NO 2
<211> LENGTH: 44
<212> TYPE: DNA
<213> ORGANISM: Porcine Adenovirus Type 3

<400> SEQUENCE: 2

gcggatcctt aattaacatc atcaataata taccgcacac tttt                      44


<210> SEQ ID NO 3
<211> LENGTH: 32
<212> TYPE: DNA
<213> ORGANISM: Porcine Adenovirus Type 3

<400> SEQUENCE: 3

cacctgcaga tacacccaca cacgtcatct cg                                  32


<210> SEQ ID NO 4
<211> LENGTH: 32
<212> TYPE: DNA
<213> ORGANISM: Porcine Adenovirus Type 3

<400> SEQUENCE: 4

cacctgcagc ctcctgagtg tgaagagtgt cc                                  32


<210> SEQ ID NO 5
<211> LENGTH: 20
<212> TYPE: DNA
<213> ORGANISM: Porcine Adenovirus Type 3

<400> SEQUENCE: 5

gactgacgcc ggcatgcaat                                                20


<210> SEQ ID NO 6
<211> LENGTH: 27
<212> TYPE: DNA
<213> ORGANISM: Porcine Adenovirus Type 3

<400> SEQUENCE: 6

cggatcctga cgctacgagc ggttgta                                        27


<210> SEQ ID NO 7
<211> LENGTH: 27
<212> TYPE: DNA
<213> ORGANISM: Porcine Adenovirus Type 3

<400> SEQUENCE: 7

cggatccata cgtacagatg aagtagc                                        27


<210> SEQ ID NO 8
<211> LENGTH: 20
<212> TYPE: DNA
<213> ORGANISM: Porcine Adenovirus Type 3

<400> SEQUENCE: 8

tctgactgaa gccgacctgc                                                20


<210> SEQ ID NO 9
<211> LENGTH: 18
<212> TYPE: DNA
<213> ORGANISM: Porcine Adenovirus Type 3
```

<400> SEQUENCE: 9
ataggcgtat cacgaggc 18

<210> SEQ ID NO 10
<211> LENGTH: 30
<212> TYPE: DNA
<213> ORGANISM: Porcine Adenovirus Type 3

<400> SEQUENCE: 10
ctggactagt ctgttccgct gagagaaaac 30

<210> SEQ ID NO 11
<211> LENGTH: 28
<212> TYPE: DNA
<213> ORGANISM: Porcine Adenovirus Type 3

<400> SEQUENCE: 11
gtggactagt ctcatgcagc gaacaacc 28

<210> SEQ ID NO 12
<211> LENGTH: 20
<212> TYPE: DNA
<213> ORGANISM: Porcine Adenovirus Type 3

<400> SEQUENCE: 12
gtactatcac cttcctaagg 20

<210> SEQ ID NO 13
<211> LENGTH: 20
<212> TYPE: DNA
<213> ORGANISM: Porcine Adenovirus Type 3

<400> SEQUENCE: 13
acagtaatga ggaggatatc 20

<210> SEQ ID NO 14
<211> LENGTH: 29
<212> TYPE: DNA
<213> ORGANISM: Porcine Adenovirus Type 3

<400> SEQUENCE: 14
taggactagt cccacagaaa aagaaaagg 29

<210> SEQ ID NO 15
<211> LENGTH: 28
<212> TYPE: DNA
<213> ORGANISM: Porcine Adenovirus Type 3

<400> SEQUENCE: 15
atggactagt cttctggtgc cgccacta 28

<210> SEQ ID NO 16
<211> LENGTH: 19
<212> TYPE: DNA
<213> ORGANISM: Porcine Adenovirus Type 3

<400> SEQUENCE: 16
cctaatctgc tcaaagctg 19

<210> SEQ ID NO 17
<211> LENGTH: 24
<212> TYPE: DNA
<213> ORGANISM: Porcine Adenovirus Type 3

-continued

<400> SEQUENCE: 17
cgggatccgg ccgctgctgc agct 24

<210> SEQ ID NO 18
<211> LENGTH: 25
<212> TYPE: DNA
<213> ORGANISM: Porcine Adenovirus Type 3

<400> SEQUENCE: 18
gcgtcgactc aaaacaggct ctcat 25